US008968995B2

(12) United States Patent
Cheng

(10) Patent No.: US 8,968,995 B2
(45) Date of Patent: *Mar. 3, 2015

(54) DETECTION, SCREENING, AND DIAGNOSIS OF HPV-ASSOCIATED CANCERS

(75) Inventor: Shuling Cheng, Fremont, CA (US)

(73) Assignee: OncoHealth Corp., Mountain View, CA (US)

( * ) Notice: Subject to any disclaimer, the term of this patent is extended or adjusted under 35 U.S.C. 154(b) by 554 days.

This patent is subject to a terminal disclaimer.

(21) Appl. No.: 12/590,747

(22) Filed: Nov. 12, 2009

(65) Prior Publication Data

US 2010/0120019 A1 May 13, 2010

Related U.S. Application Data

(60) Provisional application No. 61/199,013, filed on Nov. 12, 2008, provisional application No. 61/215,589, filed on May 7, 2009.

(51) Int. Cl.
*C12Q 1/70* (2006.01)
*G01N 33/53* (2006.01)
*G01N 33/574* (2006.01)
*G01N 33/569* (2006.01)

(52) U.S. Cl.
CPC .......... *G01N 33/57484* (2013.01); *C12Q 1/708* (2013.01); *G01N 33/56983* (2013.01); *G01N 2333/025* (2013.01)
USPC ................................ 435/5; 435/7.1; 435/7.23

(58) Field of Classification Search
None
See application file for complete search history.

(56) References Cited

U.S. PATENT DOCUMENTS

| | | | |
|---|---|---|---|
| 3,633,999 A | 1/1972 | Buckles | |
| 4,511,220 A | 4/1985 | Scully | |
| 4,619,508 A | 10/1986 | Shibuya et al. | |
| 4,744,615 A | 5/1988 | Fan et al. | |
| 4,851,978 A | 7/1989 | Ichihara | |
| 5,045,447 A | 9/1991 | Minson | |
| 5,057,411 A | 10/1991 | Lancaster et al. | |
| 5,061,025 A | 10/1991 | Debesis | |
| 5,109,465 A | 4/1992 | Klopotek | |
| 5,183,755 A | 2/1993 | Ohmoto et al. | |
| 5,224,200 A | 6/1993 | Rasmussen et al. | |
| 5,233,460 A | 8/1993 | Partlo et al. | |
| 5,307,207 A | 4/1994 | Ichihara | |
| 5,315,427 A | 5/1994 | Rauch et al. | |
| 5,328,785 A | 7/1994 | Smith et al. | |
| 5,357,365 A | 10/1994 | Ipposhi et al. | |
| 5,401,627 A | 3/1995 | Dillner et al. | |
| 5,415,995 A | 5/1995 | Schoolnik et al. | |
| 5,453,814 A | 9/1995 | Aiyer | |
| 5,561,081 A | 10/1996 | Takenouchi et al. | |
| 5,591,574 A | 1/1997 | Orth et al. | |
| 5,610,733 A | 3/1997 | Feldman et al. | |
| 5,621,529 A | 4/1997 | Gordon et al. | |
| 5,629,161 A | 5/1997 | Muller et al. | |
| 5,662,410 A | 9/1997 | Suganuma | |
| 5,665,535 A | 9/1997 | Orth et al. | |
| 5,679,509 A | 10/1997 | Wheeler et al. | |
| 5,695,770 A | 12/1997 | Raychaudhuri et al. | |
| 5,699,191 A | 12/1997 | Fork | |
| 5,754,278 A | 5/1998 | Kurtz | |
| 5,876,723 A | 3/1999 | Cole et al. | |
| 5,888,888 A | 3/1999 | Talwar et al. | |
| 5,914,389 A | 6/1999 | Huibregtse et al. | |
| 6,013,262 A | 1/2000 | Frazer et al. | |
| 6,228,578 B1 | 5/2001 | Impraim et al. | |
| 6,329,167 B1 | 12/2001 | Patterson et al. | |
| 6,355,424 B1 | 3/2002 | Lorincz et al. | |
| 6,420,106 B1 | 7/2002 | Gyllensten et al. | |
| 6,489,105 B1 | 12/2002 | Matlashewski et al. | |
| 6,524,825 B1 | 2/2003 | Mizzen et al. | |
| 6,528,278 B2 | 3/2003 | Patterson et al. | |
| 6,709,832 B1 | 3/2004 | Von Knebel Doeberitz et al. | |
| 6,743,593 B2 | 6/2004 | Hu | |
| 6,827,933 B2 | 12/2004 | Orth et al. | |
| 6,884,786 B1 | 4/2005 | Kieny et al. | |
| 6,890,514 B2 | 5/2005 | Mathur et al. | |
| 6,900,035 B2 | 5/2005 | Mizzen et al. | |

(Continued)

FOREIGN PATENT DOCUMENTS

| | | |
|---|---|---|
| CN | 1675550 | 9/2005 |
| CN | 03825051.9 | 11/2005 |
| EP | 0256321 | 2/1988 |
| GB | 2379220 | 5/2003 |
| JP | 2002296274 | 10/2002 |
| JP | 2007503208 | 2/2007 |
| JP | 2007537705 | 12/2007 |
| TW | 95142312 | 11/2006 |
| TW | 100100781 | 1/2010 |
| TW | 201012932 | 4/2010 |

(Continued)

OTHER PUBLICATIONS http://www.biology-online.org/dictionary/Native_protein—available on-line 2010.*

(Continued)

*Primary Examiner* — Shanon A Foley
(74) *Attorney, Agent, or Firm* — Yi-Shan Yang; Fenwick & West LLP

(57) ABSTRACT

Embodiments of the invention provide methods, polyclonal antibodies, monoclonal antibodies, assays, and kits for detecting HPV infection, including infection by various HPV genotypes, early and/or late HPV-associated or HPV-specific proteins or antibodies. Mononoclonal antibodies are used to detect oncogenic high risk and low risk HPV types in a single assay, which is not limited to assay type or format. Useful tools for specific detection of various HPV associated cancers are provided. HPV associated cancer biomarkers are identified and can be used in a screening method for early stage precancerous lesions as well as late stage cancer progression.

5 Claims, 28 Drawing Sheets

(56) References Cited

U.S. PATENT DOCUMENTS

| | | | |
|---|---|---|---|
| 6,933,123 | B2 | 8/2005 | Hu et al. |
| 6,939,687 | B2 | 9/2005 | Patterson et al. |
| 7,001,995 | B1 | 2/2006 | Neeper et al. |
| 7,078,061 | B2 | 7/2006 | Debad et al. |
| 7,157,233 | B2 | 1/2007 | Fischer et al. |
| 7,361,460 | B2 | 4/2008 | Williams et al. |
| 7,399,467 | B2 * | 7/2008 | Lu et al. ............ 424/130.1 |
| 7,455,973 | B2 | 11/2008 | Fischer et al. |
| 7,501,261 | B2 | 3/2009 | Meijer et al. |
| 7,510,838 | B2 | 3/2009 | Fischer et al. |
| 7,732,166 | B2 * | 6/2010 | Cheng ............ 435/69.1 |
| 7,838,215 | B2 | 11/2010 | Gombrich et al. |
| 7,888,032 | B2 | 2/2011 | Patterson et al. |
| 8,278,056 | B2 * | 10/2012 | Cheng ............ 435/7.1 |
| 2001/0034021 | A1 | 10/2001 | Muller et al. |
| 2003/0044870 | A1 | 3/2003 | Sehr et al. |
| 2003/0190602 | A1 | 10/2003 | Pressman et al. |
| 2004/0018487 | A1 | 1/2004 | Lu et al. |
| 2004/0170644 | A1 | 9/2004 | Mailere et al. |
| 2004/0175695 | A1 | 9/2004 | Debad et al. |
| 2004/0260157 | A1 | 12/2004 | Montes et al. |
| 2005/0037017 | A1 | 2/2005 | Mizzen et al. |
| 2005/0037342 | A1 | 2/2005 | Mathur et al. |
| 2005/0042600 | A1 | 2/2005 | Hu |
| 2005/0142541 | A1 | 6/2005 | Lu et al. |
| 2005/0147621 | A1 | 7/2005 | Higgins et al. |
| 2005/0159386 | A1 | 7/2005 | Kieny et al. |
| 2005/0255460 | A1 | 11/2005 | Lu et al. |
| 2005/0255468 | A1 | 11/2005 | Ridder et al. |
| 2005/0260566 | A1 | 11/2005 | Fischer et al. |
| 2006/0002929 | A1 | 1/2006 | Khare et al. |
| 2006/0029943 | A1 | 2/2006 | Hermonat et al. |
| 2006/0039919 | A1 | 2/2006 | Chang et al. |
| 2006/0121516 | A1 | 6/2006 | Norman et al. |
| 2006/0147906 | A1 | 7/2006 | Zwerschke et al. |
| 2006/0153864 | A1 | 7/2006 | Gissmann et al. |
| 2006/0154238 | A1 | 7/2006 | Hu et al. |
| 2006/0160069 | A1 | 7/2006 | Chau et al. |
| 2006/0172285 | A1 | 8/2006 | Patterson |
| 2006/0257849 | A1 | 11/2006 | Zauderer |
| 2006/0269967 | A1 | 11/2006 | Chen et al. |
| 2006/0286595 | A1 | 12/2006 | Fischer et al. |
| 2007/0048833 | A1 | 3/2007 | Sprecher et al. |
| 2007/0065810 | A1 | 3/2007 | Schlegel et al. |
| 2007/0099199 | A1 | 5/2007 | Lu et al. |
| 2007/0117167 | A1 | 5/2007 | Malinowski et al. |
| 2007/0166699 | A1 * | 7/2007 | Zwerschke et al. ............ 435/5 |
| 2007/0190062 | A1 | 8/2007 | Malinowski et al. |
| 2007/0190529 | A1 | 8/2007 | Ridder et al. |
| 2008/0038738 | A1 | 2/2008 | Weigum et al. |
| 2008/0267982 | A1 | 10/2008 | Kiselev et al. |
| 2009/0047660 | A1 | 2/2009 | Lu et al. |
| 2009/0075377 | A1 | 3/2009 | Lu et al. |
| 2009/0104597 | A1 | 4/2009 | Gombrich et al. |
| 2009/0148864 | A1 | 6/2009 | Fischer et al. |

FOREIGN PATENT DOCUMENTS

| | | |
|---|---|---|
| TW | 201043958 | 12/2010 |
| WO | WO9700888 | 1/1997 |
| WO | WO9910375 | 3/1999 |
| WO | WO0204007 A2 | 1/2002 |
| WO | WO2004085683 | 10/2004 |
| WO | WO2005008248 | 1/2005 |
| WO | 2005063286 | 7/2005 |
| WO | WO2005/063286 | 7/2005 |
| WO | WO2005088311 | 9/2005 |
| WO | WO2006083984 | 8/2006 |
| WO | WO2007059492 | 5/2007 |
| WO | WO2007095320 | 8/2007 |
| WO | WO2009042488 | 4/2009 |
| WO | 2009079192 | 6/2009 |
| WO | WO2009151632 | 12/2009 |
| WO | WO2009151633 | 12/2009 |
| WO | WO2010129821 | 11/2010 |
| WO | WO2011084598 | 7/2011 |

OTHER PUBLICATIONS

Kashmiri et al. Methods. 2005; 36:25-34).*
Tamura et al. Journal of Immunology. 2000; 164:1432-1441.*
Greenspan et al Nature Biotechnology 7:936-937 (1999).*
Griesser et al. Analytiical and Quantitative Cytology and Histology. 2004; 26: 241-245.*
Gillison et al. (Journal of the National Cancer Institute. 2008; 100: 407-420).*
Christensen et al. (Virology. 1996; 223: 174-184).*
Pavai et al. (Romanian Journal of Morphology ad Embryology. 2006; 47 (3): 229-234).*
Klaes et al. (American Journal of Surgical Pathology. 20002; 26 (11): 1389-1399).*
EPO Communication for App. No. 06846299.3, dated May 9, 2012.
Rocha-Zavaleta et al., 1997. British Journal of Cancer 75(8), 1144-1150. Differences in serological IgA responses to recombinant baculovirus-derived human papillomavirus E2 protein in the natural history of cervical neoplasia.
Final Office action for U.S. Appl. No. 12/456,076 dated May 24, 2012.
Advisory Action for U.S. Appl. No. 12/456,054 dated Jun. 13, 2012.
Advisory action for U.S. Appl. No. 12/456,055 dated Mar. 12, 2012.
Arbyn et al., 2009. J Cell Mol Med. vol. 13 No. 4 648-659. "Triage of women with equivocal or low-grade cervical cytology results: a meta-analysis of the HPV test positivity rate".
Andersson et al., 2006. International Journal of Oncology 29: 705-711. "Expression of E6/E7 mRNA from 'high risk' human papillomavirus in relation to CIN grade, viral load and p16INK4a".
Balasubramanian et al., Cancer Epidemiol Biomarkers Prev 2009;18:3008-3017. "Evaluation of an ELISA for p16INK4a as a Screening Test for Cervical Cancer".
Cardenas-Turanzas et al., Gyn Oncology 107 (2007) S138-S146. "The clinical effectiveness of optical spectroscopy for the in vivo diagnosis of cervical intraepithelial neoplasia: Where are we?".
Castle et al., 2010. AACCP. Benefits and risks of HPV testing in cervical cancer screening See Online/Articles DOI:10.1016/S1470-2045(09)70360-2.
Castle et al., American Journal of Obstetrics & Gynecology Oct. 2007 "Risk assessment to guide the prevention of cervical cancer".
Choi et al., Biosensors and Bioelectronics 20 (2005) 2236-2243. "Adenoviral p53 effects and cell-specific E7 protein-protein interactions of human cervical cancer cells".
Cole et al., Journal of Virology, Jun. 1986, vol. 58, No. 3. p. 991-995. "Genome Organization and Nucleotide Sequence of Human Papillomavirus Type 33, Which is Associated with Cervical Cancer".
Cole et al., J. Mol. Biol. (1987) 193, 599-608. "Nucleotide Sequence and Comparative Analysis of the Human Papillomavirus Type 18 Genome Phylogeny of Papillomaviruses and Repeated Structure of the E6 and E7 Gene Products".
Sawaya 2008 Annals of Internal Medicine vol. 148 • No. 7 p. 557 "Adding Human Papillomavirus Testing to Cytology for Primary Cervical Cancer Screening: Shooting First and Asking Questions Later".
Fuchs et al., Journal of Virology, May 1986, p. 626-634. vol. 58, No. 2 "Epidermodysplasia Verruciformis-Associated Human Papillomavirus 8: Genomic Sequence and Comparative Analysis".
Garcia-Alai et al., Biochemistry 2007, 46, "High-Risk HPV E6 Oncoproteins Assemble into Large Oligomers that Allow Localization of Endogenous Species in Prototypic HPV-Transformed Cell Lines".
Gravitt et al., Vaccine 265 (1008) K42-K52. "New Technologies in Cervical Cancer Screening".
Kulasingam et al., Obstetrics & Gynecology vol. 107, No. 2, Part 1, Feb. 2006 Cost-effectiveness of Extending Cervical Cancer Screening Intervals Among Women With Prior Normal Pap Tests.
Mao et al., Int. J. Cancer: 120, 2435-2438 (2007) "Evaluation of a new p16INK4a ELISA test and a high-risk HPV DNA test for cervical cancer screening: Results from proof-of-concept study".

(56) References Cited

OTHER PUBLICATIONS

Molden et al., Int. J. Cancer: 114, 973-976 (2005) "Predicting CIN2 when detecting HPV mRNA and DNA by PreTect HPV-Proofer and consensus PCR: a 2-year follow-up of women with ASCUS or LSIL Pap smear".
Marimatsu et al., Am J Clin Pathol 2005;123:716-723 "High-Throughput Cervical Cancer Screening Using Intracellular Human Papillomavirus E6 and E7 mRNA Quantification by Flow Cytometry".
NCCN Clinical Practice Guidelines in Oncology™ v.2. 2007 Cervical Cancer Screening.
Negri et al., Am J Surg Pathol 2008;32:1715-1720 "p16ink4a and HPV L1 Immunohistochemistry is Helpful for Estimating the Behavior of Low-grade Dysplastic Lesions of the Cervix Uteri".
Norchip et a;., 22nd. International Papillomavirus Conference, Vancouver, BC, Canada, Apr. 30-May 6, 2005 "Persistent transforming HPV infection may correlate with persistent histologically defined CIN II+ Summary of studies by Frank Karlsen and Hanne Skomedal".
Trope et al., Journal of Clinical Microbiology, Aug. 2009, p. 2458-2464. "Pe rformance of Human Papillomavirus DNA and mRNA Testing Strategies for Women with and without Cervical Neoplasia".
Schiffman et al., Arch Pathol Lab Med—vol. 127, Aug. 2003. "Findings to Date From the ASCUS-LSIL Triage Study (ALTS)." pp. 946-949.
Woodman et al., "The natural history of cervical HPV infection: unresolved issues." Nature Review Cancer, vol. 7 | Jan. 2007 | 11.
Ronco et al., BMC Women's Health 2008, 8:23. "New paradigms in cervical cancer prevention: opportunities and risks">.
Talora et al., Genes Dev. 2002 16: 2252-2263. Specific down-modulation of Notch1 signaling in cervical cancer cells is required for sustained HPV-E6/E7 expression and late steps of malignant transformation.
Tungteakkhun wr al., Arch Virol (2008) 153:397-408. "Cellular binding partners of the human papillomavirus E6 protein".
Sellor et al., Journal of Lower Genital Tract Disease, vol. 15, No. 2, 2011, 169-176. Association of Elevated E6 Oncoprotein With Grade of Cervical Neoplasia Using PDZ InteractionYMediated Precipitation of E6.
Ronco et al., "Effi cacy of human papillomavirus testing for the detection of invasive cervical cancers and cervical intraepithelial neoplasia: a randomised controlled trial:." Published Online Jan. 19, 2010.
Schneider-Gadicke et al., The EMBO Journal vol. 5 No. 9 pp. 2285-2292, 1986. "Different human cervical carcinoma cell lines show similar transcription patterns of human papillomavirus type 18 early genes."
Wentzensen et al., Disease Markers 23 (2007) 315-330. "Biomarkers in cervical cancer screening."
Molder et a;., Cancer Epidemiology Biomarkers and Prevention. 2005, 14, p. 367. Comparison of Human Papillomavirus Messeger DNA and DNA detection: A crodd sectional study of 4136 wk e > 30 years of age with a 2, year fikkiw-up of high=grade squamous intraepitehlial Lesion.
Sawaya et al., 2005. www.nejm.org May 10, 2007. "HPV Vaccination—More Answers, More Questions."
Perez et al., 2009. 25th International Papillomavirus Conference, Sweden. "Detection of HPV E6/E7 Oncoporteins in Cervical Cancer."
Parkin et al , Int. J. Cancer: 80, 827-841 (1999). "Estimates of the Worldwide Incidence of 25 Major Cancers in 1990."
Schneider et al., 1991 Int. j. Gynecol Pathol. 10:1-14 "Prevalence of Human Papillomavirus Genomes in Tissue from the Lower Genital Tract as Detected by Molecular in situ hybridization."
Segnan et al., 1994 European Journal of Cancer vol. 30, 873-875. "Cervical cancer screening. Human benefits and human costs in the evaluation of screening programmes."
Partridge et al., 2008 J. National Compr. Cancer Network 6: 58-82. Abstract only.

Heck et al., 1992 Proc. Natl. Acad. Sci. USA vol. 89, pp. 4442-4446, May 1992. "Efficiency of binding the retinoblastoma protein correlates with the transforming capacity of the E7 oncoproteins of the human papillomaviruses."
Chellappan et al., 1992 Proc. Natl. Acad. Sci. USA vol. 89, pp. 4549-4553, May 1992. "Adenovirus EIA, simian virus 40 tumor antigen, and human papillomavirus E7 protein share the capacity to disrupt the interaction between transcription factor E2F and the retinoblastoma gene product."
Dyson et al., Science 1989. 243: 934-937. "The Human Papilloma Virus-16 E7 Oncoprotein is Able to Bind to the Retinoblastoma Gene Product."
Zerfass et al., J. Virol. 1995, 69(10):6389. "Sequential activation of cyclin E and cyclin A gene expression by human papillomavirus type 16 E7 through sequences necessary for transformation."
Zerfass-Thome et al., 1996 Oncogene 13:2323-2330. "Inactivation of the cdk inhibitor p27KIP1 by the human papillomavirus type 16 E7 oncoprotein."
Saint, M., G. Gildengorin, and G. F. Sawaya. 2005. Current Cervical Neoplasia Screening Practices of Obstetriciaqn/Gynecologists in the US. Am. J. Obstet. Gynecol. 192:414-421.
Bosch, et al 1995. Prevalence of human papillomavirus in cervical cancer: a worldwide perspective. J Natl Cancer Inst 87:796-802.
Doeberitz, Magnus Von Knebel New Molecular tools for efficient screening of cervical cancer, Disease Markers 17 (2001) 123-128.
Fisher, et al. "The Association of Human Papillomavirus Type 16 E6 and E7 Antibodies with stage of Cervical Cancer", Gynecologic Oncology 61,73-78 (1996) Article No. 0099.
Guimaraes, et al. 2005. "Immunohistochemical expression of p161NK4a and bcl-2 according to HPV type and to the progression of cervical squamous intraepitheliallesions". J Histochem Cytochem. 53: 509-16).
Hagensee, et al. "Detection of Cervical Antibodies to Human Papillomavirus Type 16 (HPV-16) Capsid Antigens in Relation to Detection of HPV-16 DNA and Cervcal Lesions", The Jourrnal of Infectious Diseases 2000; 181: 1234-9.
Kiviat, et al. 1993. Specific human papillomavirus types as the causal agents of most cervical intraepithelial neoplasia: implications for current views and treatment. J Natl Cancer Inst 85: 934-35.
Koutsky, et al. 1992. A cohort study of the risk of cervical intraepithelial neoplasia grade 2 or 3 in relation to papillomavirus infection. N Engl J med 327:1272-1278. Abstract Only.
Kuroda, et al. 2005. The human papillomavirus E6 and E7 inducible oncogene, hWAPL, exhibits potential as a therapeutic target. Br J Cancer 92:290-3.
Li, et al. 2005. Regulation of apoptosis by papillomavirus E6 oncogene. World J Gastroenterol 11:931-37.
Longworth, et al., 2004. Pathogenesis of human papillomavirus in differentiating epithelia. Microbiol Mol Bioi Rev 68: 362-72.
Madrigal, et al. 1997. In vitro antigene therapy targeting HPV-16 E6 and E7 in cervical carcinoma. Gynecol Oncol 64: 18-25.
Meschede, et al. "Antibodies agains Early Proteins of Human Papillomaviruses as Diagnostic Markers for Invasive Cervical Cancer" Journal of Clinical Microbiology Feb. 1998, pp. 475-480.
Munoz, et al. 2003. Epidemiologic classification of human papillomavirus types associated with cervical cancer. N Engl J Med 348:518-27.
Park, et al. 1995. Molecular biology of cervical cancer and its precursors. Cancer 76: 1902-13.
Park, et al. "HPV-16-Related Proteins as the Serolgic Markers in Cervical Neoplasia", Gynecologic Oncology 69,47-55 (1998).
Parkin, et al. 1993. Estimates of the worldwide incidence of eighteen major cancers in 1985. Int J Cancer 54:594-606.
Sehr, et al. "A generic capture ELISA for recombinant proteins fused to glutathione S-transferase: validation for HPV serology" Journal of ImmunoloQical Methods 253 (2001) 153-162.
Solomon, et al. 2002. The 2001 Bethesda Systems. Terminology for reportinQ results of cervical cytoloQY. JAMA 287:2114-19.
Studentsov, et al. "Polymer-Based Enzyme-Linked Immunosorbent Assay Using Human Papillomavirus Type 16 (HPV16) Virus-Like Particles Detects HPV16 Clade-Specific Serologic Responses", Journal of Clinical Microbiology Jul. 2003 pp. 2827-2834.

(56) References Cited

OTHER PUBLICATIONS

Sun, et al., "Comparison of Peptide Enzyme-Linked Immunosorbent Assay and Radioimmunoprecipitation Assay with In Vitro-Translated Proteins for Detection of Serum Antibodies to Human Papillomavirus Type 16 E6 and #7 Proteins" Journal of Clinical MicrobioloQY Sep. 1994 pp. 2216-2230.
Tjiong, et al. "Antibodies agains Human Papillomavirus Type 16 and 18 E6 and E7 Proteins in Cervicovaginal Washings and Serum of Patients with Cervical Neoplasia" Virallmjmunolgy vol. 14, No. 4, 2001 pp. 415-424.
Veress, et al. "Human Papillomavirus DNA and Anti-HPV Secretory IgA Antibodies in Cytologically Normal Cervical Specimens" Journal of Medical Virology 43:201-207-(1994).
Viscidi, et al. 1993. Serologic response in human papillomavirus-associated invasive cervical cancer. Int. J. Cancer 55:780-784.
Walboomers, et al. "Human Papillomavirus is a Necessary Cause of Invasive Cervical Cancer Worldwide", Jouranl of PatholoQv 189: 12-19 (1999).
Wang, et al. "Cervical Mucus Antibodies against Human Papillomavirus Type 16, 18, and 33 Capsids in Relation to Presence of Viral DNA" Journal of Clinical Microbiology Dec. 1996 pp. 3056-3062.
Zumbach, et al "Antibodies Against Oncoproteins E6 and E7 of Human Papillomavirus Types 16 and 18 in Cervical-Carcinoma Patents from Russia", Int. J. Cancer 85, 313-318 (2000) [Publication of the International Union Against Cancer].
Fitzgerald Industries International Inc., Product Data Sheet for Monoclonal Antibody to human Papillomavirus (Early Protein), Human, Clone BF7. 2006.
Wang et al., Am J. Surg Patholo. 2004, vol. 28. No. 7, pp. 901-908 Detection of Human Papillomavirus DNA and Expression of p16, Rb, p53 proteins in small cell carcinomas of the uterine cervix.
Gabriella et al., BMC Cancer. 2007, vol. 7, pp. 25. Characterization of antibodies in single-chain format against the E7 oncoprotein of the human papillomavirus type 16 and their improvement by mutagenesis.
Arbyn, M., P. Sasieni, C. J. L. M. Meijer, C. Clavel, G. Koliopoulos, and J. Dillner. 2006. Chapter 9: Clinical applications of HPV testing: A summary of meta-analyses. Vaccine 24:78-89.
Castle, P. E., J. Dockter, C. Giachetti, F. A. Garcia, M. K. McCormick, A. L. Mitchell, E. B. Holladay, and D. P. Kolk. 2007. A cross-sectional study of a prototype carcinogenic human papillomavirus E6/E7 messenger RNA assay for detection of cervical precancer and cancer. Clinical cancer research : an official journal of the American Association for Cancer Research 13:2599-2605.
Cuschieri, K., and N. Wentzensen. 2008. Human Papillomavirus mRNA and p16 Detection as Biomarkers for the Improved Diagnosis of Cervical Neoplasia. Cancer Edidemiol. Biomarkers Prev. 17:2536-2545.
Dehn, D., K. C. Torkko, and K. R. Shroyer. 2007. Human Papillomavirus Testing and Molecular Markers of Cervical Dysplasia and Carcinoma. Cancer Cytopathology 111:1-14.
O'Sullivan, J. P., R. P. A'Hern, P. A. Chapman, L. Jenkins, R. Smith, and A. A. Nafussi. 1998. A case-control study of truepositive versus false-negative cervical smears in women with cervical intraepithelial neoplasia (CIN) III. Cytopathology 9:155-161.
Yim, E.-K., and J.-S. Park. 2006. Biomarkers in Cervical Cancer. Biomarker Insights 1:215-225.
Schiffman, M., A. G. Glass, N. Wentzensen, B. B. Rush, P. E. Castle, D. R. Scott, J. Buckland, M. E. Sherman, G. Rydzak, P. Kirk, A. T. Lorincz, S. Wacholder, and R. D. Burk. 2011. A long-term prospective study of type-specific human papillomavirus infection and risk of cervical neoplasia among 20,000 women in the Portland Kaiser Cohort Study. Cancer epidemiology, biomarkers & prevention : a publication of the American Association for Cancer Research, cosponsored by the American Society of Preventive Oncology 20:1398-1409.
Schweizer, J., P. S. Lu, C. W. Mahoney, M. Berard-Bergery, M. Ho, V. Ramasamy, J. E. Silver, A. Bisht, Y. Labiad, R. B. Peck, J. Lim, J. Jeronimo, R. Howard, P. E. Gravitt, and P. E. Castle. 2010. Feasibility study of a human papillomavirus E6 oncoprotein test for diagnosis of cervical precancer and cancer. Journal of clinical microbiology 48:4646-4648.
Stoler, M. H., P. E. Castle, D. Solomon, and M. Schiffman. 2007. The Expanded Use of HPV Testing in Gynecologic Practice per ASCCP=Guided Manmagement Requires the Use of Well-Validated Assays. American Journal of Clinical Pathology 127:335-337.
Woodman, C. B. J., S. I. Collins, and L. S. Young. 2007. The natural history of cervical HPV infection: unresolved issues. Nature Reviews Cancer 7:11-22.
Non-final Office action for U.S. Appl. No. 12/456,053 dated Apr. 6, 2012.
Final Office action for U.S. Appl. No. 12/456,054 dated Apr. 16, 2012.
La Selvey et al., 1992 Journal of Virological Methods, 37, 119-128. "An ELISA capture assay for the E7 transforming proteins of HPV16 and HPV18."
H Griesser et al., 2004 Analyt Quant Cytol Histol 26, 241-245. "Correlation of Immunochemical Detection of HPV L1 capsid protein in Pap Smears with Regression of High-Risl HPV Positive Milk/Moderate Dysplasia."
Tindle RW et al., 1990 Journal of General Virology. 71, 1347-1354. "Identification of B epitopes in human papillomavirus type 16 E7 open reading frame protein."
Santa Cruz Biotechnology, Inc. Product Data Sheet for sc-18114 E6-AP (C-19). 2006.
Stacey, et al. 1992. "Expression of human papillomavirus type 16 E6 protein by recombinant baculovirus and use for detection of anti-E6 antibodies in human sera", Journal of General Virology vol. 73, pp. 2337-2345.
Dorland's Pocket Medical Dictionary, P420, 25th Edition, 1995, W,B, Saunders Company. Philadelphia, Pennsylvania, 19106.
TIPO Search Report and Communication for Taiwan Invention Patent Application No. 095142312, Mar. 24, 2012. English search report on p. 1.
TIPO Search Report and Communication for Taiwan Invention Patent Application No. 098119611, Mar. 22, 2012. English search report on p. 1.
TIPO Search Report and Communication for Taiwan Invention Patent Application No. 098119612, Mar. 13, 2012. English search report on p. 1.
Volgareva et al., Protein p16 as a marker of dysplastic and neoplastic alterations in cervical epithelial cells. BMC Cancer 2004, 4:58. pp.
Liu et al., Preparation of monoclonal antibodies against human papillomavirus 16 E6 protein. Journal of Monoclonal Antibody, vol. 11 No. 3-4, Dec. 1995. English abstract on p. 3.
Su et al., Expression of human papillomavirus type 16 E6 oncogene production of monoclonal antibodies against HPV 16 E6 protein. Journal of Chinese Microbiology and Immunology, vol. 13 No. 3, 1993. English abstract on p. 4.
Wang et al., Expression of human papillomavirus type 16 L1 and construction of hybridoma cell strain of human papillomavirus type 16 L1 monoclonal antibody. Chin J. Endemiol, Jan. 20, 2007, vol. 26, No. 1. English abstract on p. 1.
SJ Lee et al., J Immunol (2001); 167; 497-504. "Both E6 and E7 Oncoproteins of Human Papillomavirus 16 Inhibit IL-IS-Induced IFN-'Y Production in Human Peripheral Blood Mononuclear and NK Cells."
S Vazquez-Vega et al., BMC Cancer (2007). 7(Suppl 1), A21. "Expression of viral and cellular cycle proteins and proteinases in cervical carcinoma cell lines as possible immunocytochemical markers of malignant phenotype."
J Doorbar, (2006) Clinical Science 1, 10, 525-541. "Molecular biology of human papillomavirus infection and cervical cancer."
M Fiedler et al., (2004) The FASEB Journal vol. 18 pp. 1120-1122. "High level HPV-16 E7 oncoprotein expression correlates with reduced pRb-levels in cervical biopsies."
KH Kim et al., (1994) Yonsei Medical Journal vol. 35, No. 1, pp. 1-9. "Expression and Localization of Human Papillomavirus Type 16 E6 and E7 Open Reading Frame Proteins in Human Epidermal Keratinocyte."

(56) References Cited

OTHER PUBLICATIONS

M Fiedler et al., (2005) Journal of General Virology, 86, 3235-3241. "Expression of the high-risk human papillomavirus type 18 and 45 E7 oncoproteins in cervical carcinoma biopsies."

E Guccione et al., (2002) Virology 283, 20-25. "Comparative Analysis of the Intracellular Location of the High- and Low-Risk Human Papillomavirus Oncoproteins."

H Valdovinos-Torres et al., (2008) The Open Virology Journal vol. 2. 15-23. "Different Isoforms of HPV-16 E7 Protein are Present in Cytoplasm and Nucleus."

T Li et al., (2001) Carcinogenesis vol. 22. No. 6 pp. 929-934. "Human papillomavirus type 16 is an important infections factor in the high incidence of esophageal cancer in Anyang area of China."

Blevins et al., Applied and Environmental Microbiology 2007, pp. 1501-1513. "Adaptation of a Luciferase Gene Reporter Aand lac ExpressionSystem to Borrelia burgdorferi."

EA Mirecka et al., (2006) Protein Expression and Purification 48, 281-291. "Expression and purification of His-tagged HPV16 E7 protein active in pRb binding!"

MS Lechner et al., (1994) Journal of Virology, Jul. 1994, p. 4262-4273. "Inhibition of p53 DNA Binding by Human Papillomavirus E6 Proteins."

B Bjorndal et al., (2003) Protein Expression and Purification 31 (2003) 47-55. "Expression and purification of receptor for activated C-kinase 1 (RACK1)."

ND Christensen et al., (1996) Virology 223, 174-184. "Surface Conformational and Linear Epitopes on HPV-16 and HPV•18 L1 Virus-like Particles as Defined by Monoclonal Antibodies"

Y Nomine et al., (2001) Protein Engineering vol. 14 No. 4 pp. 297-305, "A strategy for optimizing the monodispersity of fusion proteins: application to purification of recombinant HPV E6 oncoprotein."

ND Christensen et al., (1994) Journal o/General Virology (1994), 75, 2271-2276. "Assembled baculovirus-expressed human papillomavirus type 11 L1 capsid protein virus-like particles are recognized by neutralizing monoclonal antibodies and induce high titres of neutralizing antibodies.".

T Oltersdorf et al., (1987) J. gen. Viral. (1987), 68, 2933-2938. "Identification of Human Papillomavirus Type 16 E7 Protein by Monoclonal Antibodies."

P Di Bonito et al., (2006) Infectious Agents and Cancer 2006, 1:6. "Serum antibody response to Human papillomavirus (HPV) infections detected by a novel ELISA technique based on denatured recombinant HPVI6 L1, L2, E4, E6 and E7 proteins."

JF Kearney et al., (1979) The Journal of Immunology, V 123 No. 4 p. 1548-1550. "A New Mouse Myeloma Cell Line That Has Lost Immunoglobulin Expression But Permits the Construction of Antibody-Secreting Hybrid Cell Lines."

K Seedorf et al., The EMBO Journal 1987, vol. 6, pp. 139-144. Identification of Early Proteins of the Human Papilloma Viruses Type 16 (HPV 16) and Type 18 (HPV 18) in Cervical Carcinoma Cells.

D Patel et al., (1989) J. gen. Virol. (1989),70,69-77. "Reactivities of Polyclonal and Monoclonal Antibodies Raised to the Major Capsid Protein of Human Papillomavirus Type 16."

S-H Kee et al., (1997) J. Korean Soc. Microbiol., vol. 32, No. 3, "Generation of Monoclonal Antibodies Against Human Papillomavirus Type16 E7 Protein: Usefulness for Various E7 Detection Systems."

AK Graham et al., (1991) Clin Pathol 1991;44:96-101. "Simultaneous in situ genotyping and phenotyping of human papillomavirus cervical lesions: Comparative sensitivity and specificity."

HG Kochel et al., (1991) Int. J. Cancer: 48, 682-688. "Occurrence of Antibodies to Lt, L2, E4 and E7 Gene Products of Human Papillomavirus Types 6b, 16 and 18 Among Cervical Cancer Patients and Controls."

AK Ghosh et al., (1993) Int. J. Cancer: 53. 591-596. "Serological Responses to HPV 16 in Cervical Dysplasia and Neoplasia: Correlation of Antibodies to E6 With Cervical Cancer."

SA Jenison et al., (1990) The Journal of Infectious Disease162:60-69. "Evidence of Prevalent Genital-Type Human Papillomavirus Infections in Adults and Children."

T Fule et al., (2006) Virology 348, 289-396. "The presence of human papillomavirus 16 in neural structures and vascular endothelial cells."

Tommasino et al., Oncogene 1993, vol. 8, pp. 195-202. HPV16 E7 Protein Associates with the Protein Kinase p22 CDK2 and Cyclin A.

de Villiers et at., Virology 2004, vol. 324, pp. 17-27. "Classification of Papillomaviruses".

Banks et al., J. gen. Virol. 1987, vol. 68, pp. 1351-1359, "Identification of human papillomavirus type 18 E6 polypeptide in cells derived from human cervical carcinomas".

Thermo Scientific, Product Data Sheet for Human Papilloma Virus type 16-E7 (HPV 16-e7) Ab-1 (TVG701Y) Mouse Monoclonal Antibody. Dec. 8, 2011.

BioDesign Internation, Product Data Sheet for MAb to HPV16 E7 protein 716-218. Feb. 1, 2006.

BioDesign Internation, Product Data Sheet for MAb to HPV16 E7 protein 716-325. Aug. 3, 2005.

Chemicon International, Product Data Sheet for Mouse anti-human Papilloma Virus 16,18 E6 (C1P5) Monoclonal Antibody. Nov. 10, 2000.

Dako, Product Data Sheet for Monoclonal Mouse anti-Human Papillomavirus Clone K1H8. 2010.

G Volgareva et al., BMC Cancer 2004, 4:58. "Protein p16 as a marker of dysplastic and neoplastic alterations in cervical epithelial cells."

Digene Corporation, "hc2 HPV DNA Test," Ref. 5198-1220, 2007, 56 pages.

Matlashewski G., et al. The expression of human papillomavirus type 18E6 proteins in bacteria and the production of anti-E6 antibodies J Gen Virol (1986) 67: 1909-1916.

Radhakrishna pillai et al 1998 High-risk human papillomavirus infection and E6 protein expression in lesions of the uterine cervix Pathobiology 66(5) 240-246.

Ressler et al 2007 High-risk human popillomavirus E7 oncoprotein detection in cervical squamous cell carcinoma Clin Cancer Res 13(23) 7067-7072.

Androphy et al 1987 Identification of the HPV-16 E6 protein from transformed mouse cells and human cervical carcinoma cell lines EMBO 6(4) 989-992.

Andersson et al 2006 Expression of E6/E7 mRNA from high rish human papillomavirus in relation to CIN grade, viral load and p161NK4a Int J oncology 29:70-711.

Keegan et al 2009 Comparison of HPV detection technologies: Hybrid capture 2, preTect HPV prooer and analysis of HPV DNA viral load in HPV 16, HPV 18 and HPV 33 E6/E7 mRNA.

Inoue et al 1990 A novel monoclonal antibody against squamous cell carcinoma Jpn J Cancer res 81:176-182.

Non-final Office action for U.S. Appl. No. 11/559,366 dated Dec. 5, 2008.

Final Office action for U.S. Appl. No. 11/559,366 dated May 5, 2009.

Notice of Allowance for U.S. Appl. No. 11/559,366 dated Jan. 4, 2010.

Non-final Office action for U.S. Appl. No. 12/082,740 dated Jun. 12, 2009.

Final Office action for U.S. Appl. No. 12/082,740 dated Aug. 20, 2010.

Notice of Allowance for U.S. Appl. No. 12/082,740 dated Mar. 8, 2011.

Non-final Office action for U.S. Appl. No. 12/456,053 dated May 31, 2011.

Non-final Office action for U.S. Appl. No. 12/456,054 dated Aug. 17, 2011.

Non-final Office action for U.S. Appl. No. 12/456,055 dated Jul. 22, 2011.

EPO Communication for App. No. 09762928.1-1223/2300824, dated Aug. 15, 2011.

Extended European Search Report for App. No. 09762928.1-1223/2300824, dated Jul. 22, 2011.

EPO Communication for App. No. 06846299.3-2402/1951915, dated Apr. 7, 2010.

Extended European Search Report for App. No. 06846299.3-2402/1951915, dated Jan. 8, 2010.

(56) References Cited

OTHER PUBLICATIONS

International Search Report for Int'l App. No. PCT/US2009/003537, dated Oct. 8, 2009.
International Search Report for Int'l App. No. PCT/US2009/003538, dated Oct. 15, 2009.
International Search Report for Int'l App. No. PCT/US2010/033944, dated Jul. 2, 2010.
International Preliminary Report on Patentability for Int'l App. No. PCT/US2009/003538, dated Dec. 14, 2010.
International Preliminary Report on Patentability for Int'l App. No. PCT/US2009/003537, dated Dec. 14, 2010.
Written Opinion of the International Searching Authorigy for Int'l App. No. PCT/US2009/003538, dated Oct. 15, 2009.
Written Opinion of the International Searching Authorigy for Int'l App. No. PCT/US2009/003537, dated Oct. 8, 2009.
Written Opinion of the International Searching Authorigy for Int'l App. No. PCT/US2010/033944, dated Jul. 2, 2010.
International Search Report for Int'l App. No. PCT/US2010/060765, dated Mar. 25, 2011.
Written Opinion of the International Searching Authorigy for Int'l App. No. PCT/US2010/0060765, dated Mar. 25, 2011.
International Search Report for Int'l App. No. PCT/US2006/60883, dated Jul. 18, 2007.
International Preliminary Report on Patentability for Int'l App. No. PCT/US2006/60883, dated Jul. 18, 2007.
Written Opinion of the International Searching Authority for Int'l App. No. PCT/US2006/60883, dated Jul. 18, 2007.
EPO Communication for App. No. 06846299.3-2401, dated Oct. 21, 2011.
Final Office action for U.S. Appl. No. 12/456,055 dated Jan. 6, 2012.
Final Office action for U.S. Appl. No. 12/456,053 dated Nov. 17, 2011.
Non-final Office action for U.S. Appl. No. 12/589,692 dated Feb. 7, 2012.
Non-final Office action for U.S. Appl. No. 12/589,641 dated Feb. 6, 2012.
Non-final Office action for U.S. Appl. No. 12/456,076 dated Feb. 9, 2012.
Advisory action for U.S. Appl. No. 12/456,053 dated Jan. 26, 2012.
Advisory action for U.S. Appl. No. 12/082,740 dated Nov. 3, 2010.
Berumen et al., 2001 Asian-American Variants of Human Papillomavirus 16 and Risk for Cervical Cancer: a Case Control Study. Journal of the National Cancer Institute, vol. 93, No. 17.
Bleul et al., 1991 Human Papillomavirus Type 18 E6 and E7 Antibodies in Human Sera: Increased Anti-E7 Prevalence in Cervical Cancer Patients. Journal of Clinical Microbiology, Aug. 1991, pp. 1579-1588.
Bosch et al, 2002 Te Causal Relation between Human Papillomavirus and Cervical Cancer. J. Clinical Pathology, vol. 55, pp. 244-265.
de Villiers 1997. Papillomavirus and HPV typing. Clin. Dermatol 15:199-206.
Zur Hausen 2002. Papillomavirus and cancer: from basic studies to clinical pplication. Nat. rev. Cancer 2: 342-350.
Kreimer, et al. 2005. HPV 16 semiquantitative viral load and serological biomarkers in oral and oropharyngeal squamous cell carcinomas. Int J Cancer 115: 329-32.
Nair, Pillai 2005 Human papillomavirus and disease mechanisms: relevance to oral and cervical cancers Oral Diseases 11, 350-359.
Nindl, et al. 1994. Antibodies against linear and conformational epitopes of the human papillomavirus (HPV) type 16 E6 and E7 oncoproteins in sera of cervical cancer patients. Arch. Virol. 137:341-353.
Sasagawa, et al. 2003. Mucosal immunoglobulin-A and -G responses to oncogenic human papilloma virus capsids. Int J Cancer. Apr. 10, 2003; 104(3): 328-35.
Snijders, et al. 2006 HPV-mediated cervical carcinogenesis: concepts and clinical implications J Pathol 2006; 208: 152-164.

Stacey, et al. "Expression of human papillomavirus type 16 E6 protein by recombinant baculovirus and use for detection of anti-E6 antibodies in human sera", Journal of General Virology vol. 73, pp. 2337-2345.
Stoppler, et al. 1996 Natural Variants of the Human Papillomavirus Type 16 E6 Protein Differ in Their Abilities to Alter Keratinocyte Differentiation and to Induce p53 Degradation. Journal of Virology, p. 6987-6993 vol. 70, No. 10.
Tornesello, et al. 2004 Analysis of human papillomavirus type-16 variants in Italian women with cervical intraepithelial neoplasia and cervical cancer J Med Virol.; 74(1): 117-26.
Lehtinen, et al.2001. Human papillomavirus infection, risk for subsequent development of cervical neoplasia and associated population attributable fraction. J Clin Virolo 22:117-124.
Mougin, et al. 2001. Epidemiology of cervical papillomavirus infections. Recent knowledge. Press Med 30: 1017-23.
European Patent Office Communication dated Oct. 23, 2012 for Application No. 09762928.1, PCT/US2009003537.
Non-final Office Action for U.S. Appl. No. 13/029,131 dated Nov. 9, 2012.
China Patent Office Communication dated Apr. 1, 2013 for Application No. 200980131078.4.
China Patent Office Communication dated Mar. 13, 2012 for Application No. 200980131077.X.
Notice of Allowance for U.S. Appl. No. 12/456,076 dated Aug. 1, 2012.
Examiner-Initiated Interview Summary and Amendment after Final initiated by the Examiner for U.S. Appl. No. 12/456,076 dated Aug. 1, 2012.
European Patent Office Communication dated Jan. 30, 2013 for Application No. 12164498.3-2402/2522756.
Non-final Office Action for U.S. Appl. No. 13/585,509 dated Jan. 15, 2013.
Qiao et al., 2008. "A New HPV-DNA Test for Cervical-Cancer Screening in Developing Regions: a Cross-Sectional Study of Clinical Accuracy in Rural China." Lancet Oncology 9: 929-936.
Zhao et al., 2010. "Performance of High-Risk Human Papillomavirus DNA Testing as a Primary Screening for Cervical Cancer: a Pooled Analysis of Individual Patient Data from 17 Population-Based Studies from China." Lancet Oncology 11: 1160-1171.
Zhao et al., 2011. "Pooled Analysis of a Self-Sampling HPV DNA Test as a Cervical Cancer Primary Screening Method." JNCI 104: 1-11.
Arbyn et al., 2010. "HPV-Based Cervical-Cancer Screening in China." World Health Organization GLOBOCAN 2008. Published online Nov. 12, 2010. http://globocan.iarcfr/.
Wong et al., 2011. "Efficacy of Abbott Real Time High Risk HPV Test in Evaluation of Atypical Squamous Cells of Undetermined Significance from an Asian Screening Population." Journal of Clinical Virology 51, 136-138.
Petignat et al., 2012. "Is It Time to Introduce HPV Seld-Sampling for Primary Cervical Cancer Screening?" Editorial, JNCI. 104 (3): pp. 1-2.
Japan Patent Office Communication dated Apr. 2, 2013 for Application No. 2011-513504.
Final Office Action for U.S. Appl. No. 12/456,054 dated May 14, 2013.
Taiwan Patent Office Communication dated Apr. 8, 2013 for Application No. 100100781.
Taiwan Patent Office Communication dated Apr. 3, 2013 for Application No. 095142312.
EPO Communcation for Application No. 12164498.3 dated on Sep. 28, 2012.
MA Romanos et al., 1995. Production of a phosphorylated GST::HPV-6 E7 Fusion Protein Using a Yeast Expression Vector and Glutathione S-transferase Fusions. Gene. 152, 137-138.
Partial European Search Report for Application No. 12164498, dated Sep. 19, 2012.
T. Ristriani et al., 2001. "Specific Recognition of Four-way DNA Junctions by the C-terminal Zinc-binding Domain of HPV Oncoprotein E6." J. Mol. Biol. 305, 729-739.

(56) References Cited

OTHER PUBLICATIONS

KLMC Franken et al., 2000. "Purificaiton of His-Tagged PRoteins by Immobilized Chelate Affinity Chromatography: The Benefits from the Use of Organic Solvent." Protein Expression and Purification 18, 95-99.
Y. Nomine et al., 2001. "A strategy for optimizing the monodispersity of fusion proteins: application to purification of recombinant HPV E6 oncoprotein." Protein Engineering. 14, No. 4 pp. 297-305.
JA DeVoti et al., 2004. "Failure of Gamma Interferon but Not Interleukin-10 Expression in Response to Human Papillomavirus Type 11 E6 PRotein in Respiratory Papillomatosis." Clinical and Vaccine Immunology 11(3) 538-547.
TIPO Search Report and Communication for Taiwan Invention Patent Application No. 098119612, Oct. 5, 2012. Search Report Brief is on p. 1.
European Patent Office Communication dated Dec. 3, 2012 for Application No. 09762929.9, PCT/US2009003538.
Oltersdorf et el., 1987. "Identification of Human Papillomavirus Type 16 E7 Protein by Monoclonal Antibodies." J. Gen. Virol. 68, 2933-2938.
Jochmus et al., 1999. "Chimeric Virus-like Partiles of the Human Papillomavirus Type 16 (HPV 16) as a Prophylactic and Therapeutic Vaccine." Archives of Medical Research. 30, 269-274.
HyTest News. Mar. 2008, pp. 1-8. Advanced ImmunoChemical, Finland.
Mattil-Fritz et al., 2008. "Immunotherapy of equine sarcoid: dose-escalation trial for the use of chimeric papullomavirus-like particles." Journal of General Virology 89, 138-147.
Rizk et al., 2008. "Reactivity pattern of 92 monoclonal antibodies with 15 human papillomavirus types." Journal of General Virology, 89, 117-129.
J Melnikow et al., 1998. "Natural history of Cervical Squamous Intraepithelial Lesions: A meta-Analysis." 1998 vol. 92, No. 4, pp. 727-735.
Non-final Office Action for U.S. Appl. No. 12/456,054 dated Sep. 25, 2012.
Final Office Action for U.S. Appl. No. 12/456,053 dated Sep. 24, 2012.
JH Joen et al., "Immunocytochemical detection of HPV16E7 in cervical smear." 2007. Experimental and Molecular Medicine, vol. 39, No. 5, 621-628.
C Liang et al., "Biomarkers of HPV in Head and Neck Squamous Cell Carcinoma." 2012, Cancer Research. Published online Sep. 18, 2012.
D Holzinger et al., "Viral RNA Patterns and High Viral Load Realiably Define Oropharynx Carcinomas wit hActive HPV16 Involvement." 2012, Cancer Research. Published online Sep. 18, 2012.
AG Ostor et al., "Natural History of Cervical Intraepithelial Neoplasia: A Critical Review." 1993 International Journal of Gyncological Pathology . 12:186-192.
European Patent Office Communication dated Jun. 6, 2013 for Application No. 10842601.6.
European Patent Office Communication dated Jul. 18, 2013 for Application No. 10772861.0.
Non-final Office action dated Jul. 3, 2013 for U.S. Appl. No. 12/456,055.
Santer et el., 2007 Carcinogenesis, vol. 28 No. 12 pp. 2511-2520. "Human papillomavirus type 16 E7 oncoprotein inhibits apoptosis mediated by nuclear insulin-like growth factor-binding protein-3 by enhancing its ubiquitin/ proteasome-dependent degradation."
Non-final Office action dated Jul. 11, 2013 for U.S. Appl. No. 13/585,509.
China Patent Office Communication dated Jul. 19, 2013 for Application No. 201080020175.9.
Taiwan Patent Office Communication dated Aug. 22, 2013 for Application No. 100100781.
Zhao et al., 2013 Cancer Prevention Research. Published OnlineFirst Jul. 22, 2013. "An Evaluation of Novel, Lower-Cost Molecular Screening Test for Human Papillomavirus in Rural China."

Shi et al., 2009 American Journal of Epideminology vol. 170 No. 6. 708-716. "Human papillomavirus testing for cervical cancer screening: results from a 6-year prospective study in rural China."
Belinson et al., Am J. Clin Pathol 2011; 135:790-795. "A population-based clinical trial comparing endocervical high-risk HPV testing using hybrid capture 2 and Cervista from the SHENCCAST II study."
Dockter et al., 2009 Journal of Clinical Viroogy 45, 51: 539-547. "Analytical characterization of the APTIMA HPV assay."
Wong et al., 2011 Journal of Clinical Virology 51 (2011) 136-138. "Efficacy of Abbott real time high risk HPV test in evaluation of atypical squamous cells of undetermined significance from and Asian screening population."
Branca et al., 2005 Am J Clin Pathol 124: 113-121. "Survivin as a marker of cervical intraepithelial neoplasia and high-risk human papillomavirus and a predictor of virus clearance and prognosis in cervical cancer."
Branca et al., 2006 J Clin Pathol 59: 40-47. "Aberrant expression of VEFG-C is related to grade of cervical intraepithelial neoplasia (CIN) and high risk HPV but does not predict virus clearance after treatment of CIN or prognosis of cervical cancer."
Lambert et al., 2006 Experimental and Molecular Pathology 80: 192-196. "p16INK4A expression in cervical premalignant and malignant lesion."
Giannoudis et al., 2000 British J. Cancer 81:424-7. "Differential expression of p53 and p21 in low grade cervical squamous intraepithelial lesions infected with low, intermediate, and high risk human papillomaviruses."
Saqi et al., 2002 "Overexpression of p16INK4A in liquid-based specimens (SurePath) as marker of cervical dysplasia and neoplasia." 27: 365-370.
Park et al., 1998 "HPV-16-releated proteins as the serologic markers in cervical neoplasis." Gynecologic oncology 69, 47-55.
Lie et al., 1999 Int J Gynecol Pathol 18(1): 5-11."Expression of p53, MDM2, and p21 proteins in high-grade cervical intraepithelial neoplasia and relationship to human papillomavirus infection."
Aug. 30, 2013 EPO Office communication for EPA No. 09762928.1.
Sep. 9, 2013 USPTO Communication for U.S. Appl. No. 13/520,021.
Fiedler et. al., 2004 FASEB Journal express article. High Level HPV-16 E7 oncoprotein expression correlates with reduced pRb-levels in cervical biopsies.
Sep. 18, 2013 USPTO Non-Final Office Action for U.S. Appl. No. 12/456,053.
Sep. 30, 2013 USPTO Non-Final Office Action for U.S. Appl. No. 12/456,054.
Sep. 30, 2013 USPTO Final Office Action for U.S. Appl. No. 12/590,747.
European Patent Office Communication dated Oct. 28, 2013 for Application No. 12164498.3-1404.
Dec. 20, 2013 USPTO Non-Final Office Action dated Dec. 20, 2013 for U.S. Appl. No. 13/520,021.
Caceres-Cortes et al., Implication of Tyrosine Kinase Receptor and Steel Factor in Cell Density-dependent Growth in Cervical Cancers and Leukemias. Cancer Research. 2001;61:6281-6289.
Taiwan Patent Office Communication, Notice of Allowance, for TW Patent App. No. 95142312, Feb. 11, 2014.
Japan Patent Office Communication for JP Patent App. No. 2011-513505, Jan. 14, 2014.
Japan Patent Office communication for JP Patent App. No. 2012-509989, Jan. 21, 2014.
China Patent Office communication for CN Patent App. No. 200980131077.x, Jan. 24, 2014.
US Patent Office non-final Office action for U.S. Appl. No. 13/319,312, Feb. 28, 2014.
China Patent Office communication for CN Patent App. No. 200980131078.4, Feb. 12, 2014.
Pillai et al., Cancer Epidemiology Biomarkers & Prevention 1996; 5: 329-335. "The presence of human papillomavirus-16/-18 E6, p. 53, and Bcl-2 protein in cervicovaginal smears from patients with invasive cervical caner".
Pavai et al., Romanian Journal of Morphology and Embryology 2006, 47(3): 229-234. "Comparative detection of high-risk HPV (16, 18, 33) in ervical bioptic material of County Hospital of Tg. Mures."

(56) References Cited

OTHER PUBLICATIONS

Non-final Office action for U.S. Appl. No. 12/456,055 dated Mar. 21, 2014.
Non-final Office action for U.S. Appl. No. 12/590,747 dated Mar. 26, 2014.
Final Office action for U.S. Appl. No. 13/520,021 dated Apr. 14, 2014.
Apgar et al., "The Bethesda System Terminology." Am Fam Physician 2003; 68: 1992-1998.
Kovanda et al., "Characterization of a Novel Cutanous Human Papillomavirus Genotype HPV-125." PLosOne 2011; vol. 6 e22414vol.
Narechania et al., "Phylogenetic incongruence among Oncogenic Genital Alpha Human Papillomaviruses." J. Virol. 2005, 79(24): 15503.
Rudikoff et al., "Single amino acid substitution altering antigen-binding specificity." Proc. Natl. Acad. Sci 1982 vol. 79 1979-1982.
European Patent Office Communication for EPO Patent App. No. 097629299 dated Feb. 27, 2014.
China patent Office Communication for CN Patent App. No. 2010800609626 dated Mar. 10, 2014.
Liu et al., "Fixed-cell immunoperoxidase Technology." China Academic Journal, Production Technology. 1993 vol. 23 No. 2 pp. 37-38.
Taiwan Intellectual Property Office Notice of Allowance for TW Patent App. No. 098119612 dated May 9, 2014.
Final Office action for U.S. Appl. No. 13/319,312 dated Jul. 24, 2014.
Final Office action for U.S. Appl. No. 12/590,747 dated Jul. 23, 2014.
Final Office action for U.S. Appl. No. 12/456,055 dated Sep. 9, 2014.
European Patent Office Communication for EPO Patent App. No. 097629299108426 01.6 dated Jul. 14, 2014.
European Patent Office Communication for EPO Patent App. No. 12164498.3 dated Jun. 26, 2014.
European Patent Office Communication for EPO Patent App. No. 09762928.1 dated Aug. 26, 2014.
Japan Patent Office Communication for JP Patent App. No. 2011-513504 dated May 2, 2014.
Japan Patent Office Communication for JP Patent App. No. 2012-548021 dated Jul. 15, 2014.
China patent Office Communication for CN Patent App. No. 201080020175.9 dated May 28, 2014.
Notice of Allowance for U.S. Appl. No. 12/456,053 dated Jun. 13, 2014.
Notice of Allowance for U.S. Appl. No. 12/456,054 dated Jun. 13, 2014.

\* cited by examiner

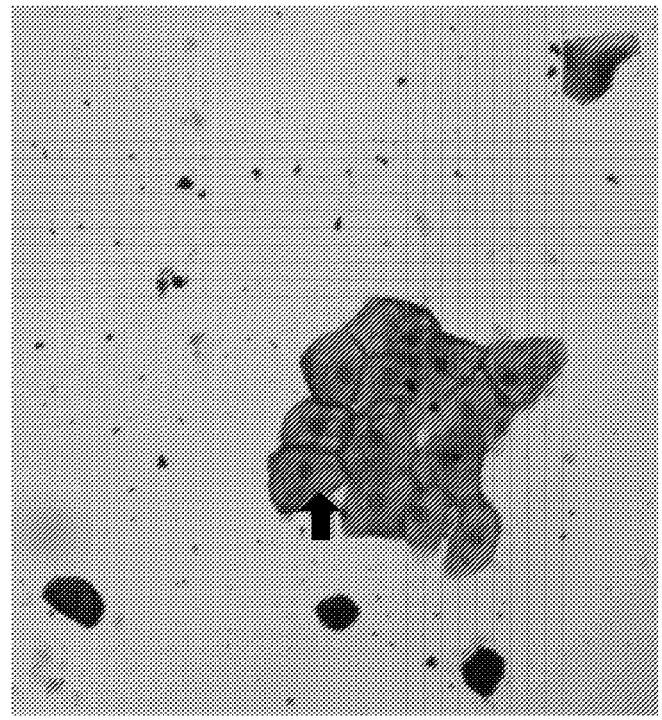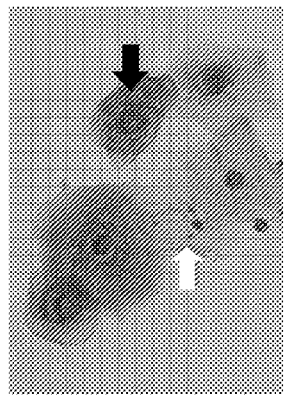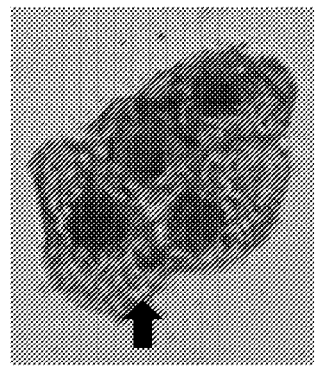
Figure 24C
Figure 24B
Figure 24A

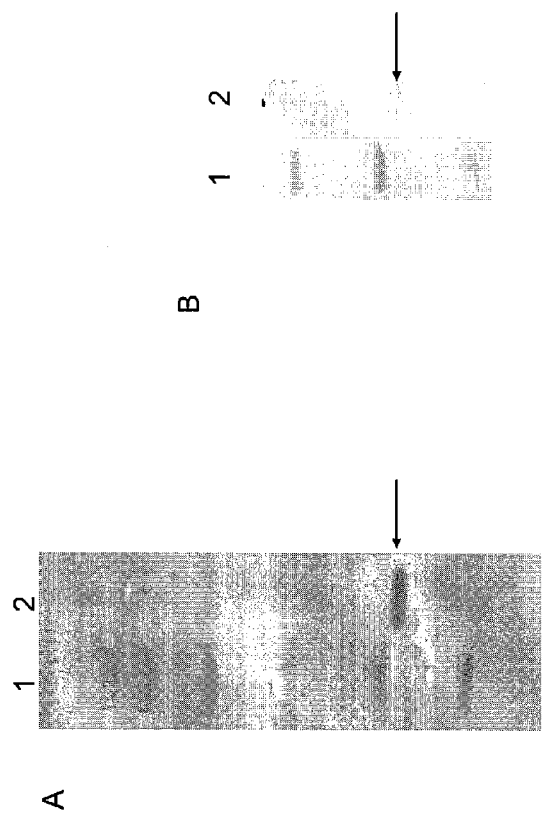
A). SDS-PAGE and B). western blot demonstrating the full length E6 recombinant protein stained with commassie blue, then probed with anti-E6 monclonal antibody, respectively.
Lane1:Protein marker (14.4, 20.1, 31, 43, 66.2, 96.7KD upward)
Lane2:HPV16E6 recombinant protein
Figure 27A&B

DETECTION, SCREENING, AND DIAGNOSIS OF HPV-ASSOCIATED CANCERS

CROSS-REFERENCE TO RELATED APPLICATIONS

This application claims benefit of U.S. provisional patent application Ser. No. 61/199,013, filed Nov. 12, 2008, and U.S. provisional patent application Ser. No. 61/215,589, filed May 7, 2009. Each of the aforementioned related patent applications is herein incorporated by reference.

This application is cross related to U.S. Pat. No. 7,732,166, issued on Jun. 8, 2010, entitled "Detection Method for Human Papillomavirus (HPV) and Its Application in Cervical Cancer", U.S. Pat. No. 7,972,776, issued on Jul. 5, 2011, entitled "Protein Chips for HPV Detection", U.S. App. Ser. No. 61/131,991, filed on Jun. 13, 2008, entitled "Antibodies and Assays for HPV Detection", and U.S. App. Ser. No. 61/192,912, filed on Sep. 22, 2008, entitled "Novel Monoclonal Antibodies against HPV Proteins Useful for Early State and Late Stage Detection, Screening, and Diagnosis of HPV Related Cervical Cancer", U.S. application Ser. No. 12/456,053, filed on Jun. 10, 2009, entitled "Novel Monoclonal Antibodies against HPV Proteins", U.S. application Ser. No. 12/456,054, filed on Jun. 10, 2009, entitled "in situ Detection of Early Stages and Late Stages HPV Infection", U.S. application Ser. No. 12/456,055, filed on Jun. 10, 2009, entitled "in situ Detection of Early Stages and Late Stages HPV Infection", U.S. application Ser. No. 12/456,076, filed on Jun. 10, 2009, entitled "Detection of Early Stages and Late Stages HPV Infection", and U.S. application Ser. No. 13/319,312, filed on Nov. 7, 2011, entitled "Identification of High Grade or >=CIN2 for Early Stages and Late Stages Detection, Screening, and Diagnosis of Human Papillomavirus (HPV) and HPV-Associated Cancers". Essential material from each of the above applications is hereby incorporated by reference in their entireties.

BACKGROUND OF THE INVENTION

Infection by human papillomaviruses (HPV) at specific epithelium cells to induce epithelial proliferations plays an important role for cervical carcinogenesis. About 99 percent of confirmed cervical cancer cases are found to be associated with HPV infection with biopsy-confirmed squamous intraepithelial lesions (SIL) or cervical intraepithelial neoplasia (CIN). The incidence of HPV infection, primarily transmitted through sexual contact, is highest among young women and about 20 million sexually active men and women worldwide are currently infected.

In addition to cervical cancer, the presence of HPV DNA has been detected in tumor tissues of head and neck cancer, oral cancer, esophageal cancer, and some skin cancers, as well as lung cancer and colorectal cancer. The detection of HPV DNA in colorectal cancer tissues by in situ hybridization and PCR suggested that HPV infection might be associated with the carcinogenesis of colorectal cancer. However, HPV DNA was not detectable by regular PCR in one earlier study and a survey of HPV16 virus-like particle (VLP) antibodies in patients with epithelial cancers also failed to provide an association of HPV with colorectal cancer challenging the association of colorectal cancers with HPVs. However, colorectal HPV infection is common in patients with colorectal cancer, albeit at a low DNA copy number, with HPV16 being the most prevalent type. The inconsistent results may come from the issues of assay sensitivity for HPV detection. HPV infection may play a role in colorectal carcinogenesis. More sensitive assays for detection of HPV in colorectal cancer are required to demonstrate the association of HPV with carcinogenesis of colorectal cancer.

Some genital malignancies like vulvar or cervical neoplasms are associated with previous infection with human papillomavirus (HPV). Because of vicinity of bladder to mucosal surface of urogenital tract, HPV may play a significant role in transitional cell carcinoma (TCC). The etiology of TCC, which represents 90 percent of bladder malignancies, is not quite clear, while squamous cell carcinoma (5%) of the bladder is well associated with some factors like urinary stones and prolonged infections. HPV detection rate in clinical samples of invasive cervical cancer can be as high as 99%. Recently, conflicting findings have been reported on association of HPV infection and TCC. Using PCR techniques to detect human papillomavirus (HPV), HPV DNA can be observed prevalently in about 40% to 45% of penile carcinoma clinical samples, about 45% of vulvar carcinoma, and some bladder malignancies.

Methods of detecting HPV infection with nucleic acid methods, such as "DNA Hybrid Capture", have been developed. However, they are not ideal, not only due to its high cost, assay operation procedures, the requirements for facility, equipment, and highly trained personnel, but also its very low positive predictive value to CIN. In addition, DNA testing could not differentiate the diagnosis of LSIL from HSIL, or CIN lesions from non-transforming latent or remissive viral infection. What is needed is a low cost, simple, sensitive and specific assay that can be performed routinely in a clinical lab or doctor's office and is capable of detecting early stages of epithelial lesions, distinguishing LSIL from HSIL, or predicting the risk of progression into cervical cancer.

Thus, there is a need to detect whether HPV proteins are expressed in a variety of carcinomas and cancers, and determine whether HPV proteins play any role in the progression of the different types of carcinomas/cancers; and if so, which HPV proteins are important in these carcinomas/cancers.

SUMMARY OF THE INVENTION

Embodiments of the invention provide a method of assessing the risk for malignancy of a variety of cancers and carcinomas in a clinical sample from a human subject including, providing a clinical sample from a source sample other than cervical samples; conducting one or more detection assays on the clinical sample from the human subject using one or more anti-HPV antibodies; and detecting the presence of HPV proteins present in the clinical sample to assess the risk of malignancy for the human subject. In another embodiment, the HPV proteins in the human subject are detected using antibodies raised against HPV recombinant proteins, including but not limited to, various polyclonal and monoclonal antibodies against various HPV early and late proteins. In another embodiment, the one or more immunoassays include, but are not limited to, immunohistochemistry (IHC) assay, immunocytochemistry (ICC) assay, ELISA, and protein chip assay, etc.

In one embodiment, a method of detecting papillomavirus infection in a human subject includes obtaining a clinical sample from the human subject; and conducting one or more immunological assays on the clinical sample from the human subject using lab-generated anti-HPV antibodies to detect the presence of HPV infection from the presence of HPV proteins in the clinical sample and access the risk for malignancy of non-cervical cancer.

In one embodiment, IHC staining for cancers other than cervical cancer, including, but not limited to, bladder cancers, head and neck cancers, ovarian cancers were provided herein. In one embodiment, the presence of HPV oncoproteins are herein detected in a variety of cancers and carcinomas, including, but not limited to, bladder cancer, head and neck cancer, ovarian cancers, bladder transitional cell carcinoma (TCC), endometrioid adenocarcinoma, serous papillary cystadenocarcinoma (SPC), urothelial carcinoma, squamous cell carcinomas of cheeks, tonsillar carcinoma, squamous cell carcinoma of larynx, squamous cell carcinoma of nose, squamous cell carcinoma of upper jaw, among others. In another embodiment, HPV oncoproteins are herein not detected in some low grade squamous cell carcinomas of nasal cavity, clear cell carcinoma, sarcomatoids carcinomas of the left ethmoid sinus, low grade endometrioid adenocarcinoma, among others.

Embodiments of the invention provide useful antibodies for in situ detection of HPV L1, E6, and E7 proteins in various cancers and carcinoma. The antibodies and assays as described herein are useful for detecting HPV oncoproteins as cancer biomarkers, screening for various HPV associated cancers, and/or accessing the risk for malignant transformation into these HPV associated cancers. As an example, it is possible that male subjects can be HPV carriers to transmit HPV to their partners. A robust test for HPV detection as described in this invention provides promise to develop assays in different formats for detection of HPV in different tissues for various HPV associated cancers.

Developing appropriate assays, such as HPV immunoassays, is needed for detection of HPV oncoproteins or biomarkers for various cancers associated with HPV infection. The presence of E6/E7 oncoproteins could be evidence to indicate high progression risk of various types of cancer. A robust tool for HPV detection as described herein provides promise to develop assays in different formats for detection of HPV in various tissues from different cancers.

SUMMARY OF DRAWING

FIG. 24A shows the representative staining image of cervical cells from a CIN2 cervical scrape sample prepared by thin prep and stained by a mouse monoclonal anti-HPV E7 antibody in an immunocytochemistry (ICC) assay.

FIG. 24B shows the representative staining image of cervical cells from a CIN3 cervical scrape sample prepared by thin prep and stained by a mouse monoclonal anti-E6 antibody in an ICC assay.

FIG. 24C shows the representative image of cervical cells from an adenocarcinoma (ADC) cervical scrape sample prepared by thin prep and stained by the same anti-E6 antibody shown in FIG. 24B in an ICC assay.

FIG. 27A demonstrates one embodiment of an exemplary purified recombinant protein encoded by an E6 early gene as visualized by SDS-PAGE by staining with commassie blue.

FIG. 27B demonstrates detection of a purified recombinant protein, HPV-16 E6 recombinant protein, by Western blot analyses according to one or more embodiments of the invention.

DETAILED DESCRIPTION

Figure 1A:
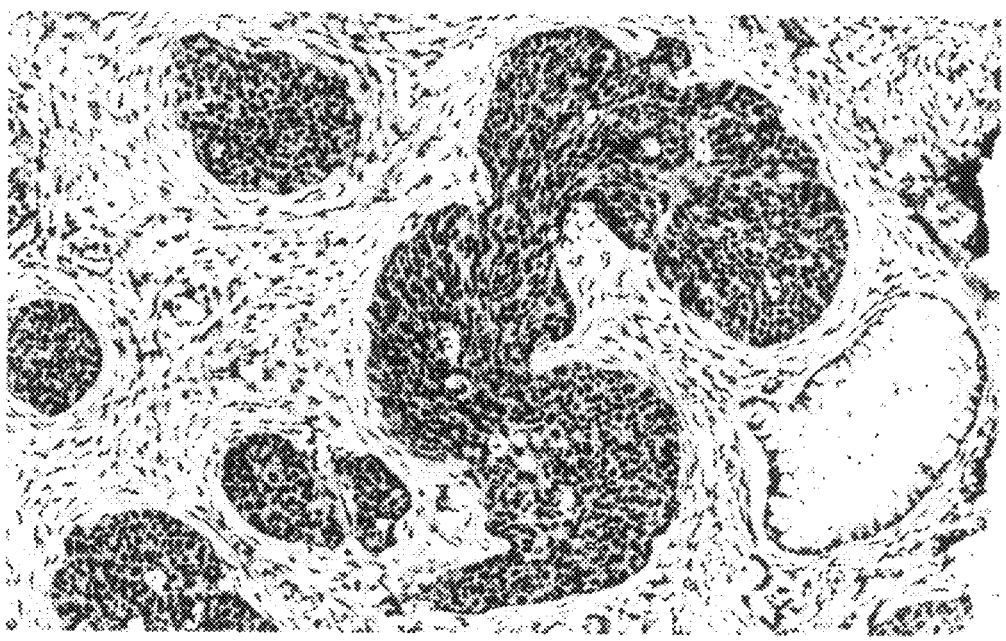
FIG. 1A-1B: Images of IHC using anti-HPV-E6 antibody on cervical cancer tissue and its adjacent normal tissue.

Embodiments of the invention provide various methods, detection assays, kits, polyclonal and monoclonal antibodies, polypeptides, recombinant proteins, and nucleic acids useful for detecting HPV proteins present in various cancers from various tissues. In one embodiment, various monoclonal antibodies against HPV proteins are provided such that HPV proteins can be detected by a single monoclonal antibody. Detecting HPV proteins of the invention include, but are not limited to, HPV E6 proteins, HPV E7 proteins, HPV L1 proteins, etc. The sources of HPV proteins for making monoclonal antibodies are not limited and can be from various HPV types/species.

In one embodiment, a method of assessing the risk for malignancy of a variety of cancers and carcinomas in a clinical sample from a human subject includes providing a clinical sample from a source sample other than cervical sample; conducting one or more detection assays on the clinical sample from the human subject using one or more anti-HPV antibodies; and detecting the presence of HPV proteins present in the clinical sample to assess the risk of malignancy for the human subject. In another embodiment, the HPV proteins in the human subject are detected using antibodies raised against HPV recombinant proteins, including but not limited to, various polyclonal and monoclonal antibodies against various HPV early and late proteins. In another embodiment, the one or more immunoassays include, but are not limited to, immunohistochemistry (IHC) assay, immunocytochemistry (ICC) assay, ELISA, and protein chip assay, etc.

In one embodiment, a method of detecting papillomavirus infection in a human subject includes obtaining a clinical sample from the human subject; and conducting one or more immunological assays on the clinical sample from the human subject using lab-generated anti-HPV antibodies to detect the presence of HPV infection from the presence of HPV proteins in the clinical sample and assess the risk for malignancy of non-cervical cancer.

As an example, the invention provides one or more anti-HPV-E7, anti-HPV-E6, or anti-HPV-L1 monoclonal antibody useful for detecting HPV infection and predicting HPV associated cancers including, but not limited to, head and neck cancers, bladder cancers, etc. with 82% to 100% of positive predictive value (PPV). The obtained monoclonal antibodies can be very useful in screening clinical samples for various invasive cancers. In an IHC assay on oral biopsy samples, the best results using the monoclonal antibodies of the invention result in about 100% positive predictive value (PPV) for head and neck cancer. Also, monoclonal antibodies with 100% positive predictive value (PPV) for IHC staining of other clinical samples like bladder cancer, head and neck cancer, and ovarian cancer, can also be obtained.

In another embodiment, a negative predictive value (NPV) ranging from more than about 31% to about 100% for various clinical cancer samples can be observed in an IHC assay for one or more anti-HPV-E7 or anti-HPV-E6 monoclonal antibody. NPV value of about 100% for clinical biopsy samples as observed for some of the antibodies provided herein supports the use of these antibodies for diagnosing and screening HPV associated cancers.

In one embodiment, IHC staining for cancers other than cervical cancer, including, but not limited to, bladder cancers, head and neck cancers, ovarian cancers were provided herein. In one embodiment, the presence of HPV oncoproteins are herein detected in a variety of cancers and carcinomas, including, but not limited to, bladder cancer, head and neck cancer, ovarian cancers, bladder transitional cell carcinoma (TCC), endometrioid adenocarcinoma, serous papillary cystadenocarcinoma (SPC), urothelial carcinoma, squamous cell carcinomas of cheeks, tonsillar carcinoma, squamous cell carcinoma of larynx, squamous cell carcinoma of nose, squamous cell carcinoma of upper jaw, among others. In another embodiment, HPV oncoproteins are herein not detected in some low grade squamous cell carcinomas of nasal cavity, clear cell carcinoma, sarcomatoid carcinomas of the left ethmoid sinus, low grade endometrioid adenocarcinoma, among others.

As an example, all monoclonal antibodies optimized on IHC assay and tested on each tissue microarray using a method that includes providing a thin section containing one or more kinds of tissue cells from a clinical tissue sample of the human subject, applying the thin section on a slide, conducting one or more immunohistochemical assays on the slide containing the thin section of the clinical tissue sample, staining the thin layer of human cells using one or more antibodies generated against one or more purified recombinant papillomavirus proteins, wherein at least one antibody is capable of recognizing a papillomavirus early protein, and detecting in situ one or more proteins from one or more papillomavirus types present in the thin section of the clinical tissue sample on the slide. All figures show representative IHC staining by at least one monoclonal anti-HPV-E6 antibodies, one monoclonal anti-HPV-E7 antibodies or one monoclonal anti-HPV-L1 staining compared to its normal adjacent tissues. Both cytoplasm and nucleus staining were found in the dysplasia or tumor cells.

As an example, using normal epithelial staining as a base line, the percentage of IHC staining over 10% is considered as positive; otherwise, it is negative for the IHC assay. In one embodiment, E6 and E7 oncoproteins expression, the assays or sample formats in detecting the presence of HPV proteins in various HPV associated cancers are not limited and can be used for various tissues like cervical, bladder, head and neck, colon, cervical cells, cervical scrapes, oral scrapes, nose scrapes, serum, body fluids, etc. The useful screening or diagnosing assay can be IHC, ICC, flow cytometry assay, antibodies coupled to beads, rapid tests, protein chips, dot blots, slots, as well a conventional ELISA assay. HPV proteins can be detected by the antibodies of the invention to be present in tumor cells as evidenced by IHC staining after scoring by a pathologist.

As another example, on the cellular level, HPV proteins can be observed in the nucleus and cytoplasm, but not in the membrane of a cell. It is found that the HPV proteins are present in the nucleus and/or cytoplasm of dysplasia from most of the samples tested. The staining of tumor cells by the antibodies of the invention results in diffused staining. However, there is focused staining as well. As an example, for invasive cancer like SCC and ADC described here in this invention, staining of the tumor cells by anti-HPV protein antibodies displays distinct high levels of staining on both the nucleus and cytoplasm as compared to the staining of the adjacent normal tissues.

Comparing various HPV proteins related to HPV early genes and late genes, it is found that HPV E6 and E7 oncoproteins are present at high level in head and neck cancers. However, the E6 and E7 oncoproteins are detected at lower positive rate in bladder cancer and ovarian cancer compared to detection of L1 protein in the same tumor tissues. Results indicate tat HPV E6 or E7 can be served as a cancer biomarker and the invention provides various antibodies tested to high PPV and high NPV values, high specificity and high sensitivity for clinical samples from all stages of a variety of cancers associated with HPV infection. It is possible to use one single monoclonal antibody to detect HPV E6 or E7 proteins present in various early precancerous lesions, as well as late stage invasive cancer and other HPV associated cancers. For example, the antibodies are very successful in screening CIN2 and CIN 3 lesions, as well as various types of cervical cancers during cancer development. These tools apply to other HPV associated cancers as demonstrated in this invention.

Head and neck cancer: as an example, tonsillar carcinoma is the most prevalent oropharyngeal carcinoma. Cigarette smoking and alcohol are the primary risk factors traditionally associated with the development of this malignancy. The association of human papillomavirus (HPV) infection with tonsillar carcinoma has been suggested by the following observations: HPV DNA has been detected in around 50% of tonsillar carcinomas with HPV-16 as the predominant virus type. HPV-16 DNA is transcribed and present in episomal form in most tonsillar carcinomas and can be detected in carcinoma cells by in situ hybridization. Patients with HPV-16 positive tonsillar tumors seem to have a better survival than HPV negative patients, thus presenting a distinct group among patients with tonsillar carcinoma. Patients with anogenital cancer might have an increased risk for tonsillar carcinoma; HPV DNA has also been detected in lymph node metastases. It should be emphasized that the detection of viral DNA per se does not confirm that the virus has a causal connection with malignant transformation. However, so far, it seems that HPV-16 E6 and E7 are actively transcribed in most tonsillar carcinomas that have been analyzed Independent of the physical state of the virus, all tonsillar tumors expressed E7 encoding HPV-33 E6*I mRNA, it has been suggested that the transcription of HPV-16 E6/E7 mRNA in tonsillar carcinomas is not necessarily dependent on viral DNA integration.

To demonstrate a variety of tumors from head and neck cancers can be detected by HPV IHC as described in this invention, Table 7 shows IHC results by anti-E6 or anti-E7 antibody stain positively on tissues including Squamous cell carcinoma (SCC) of left cheek, SCC of cheek, SCC of larynx, and SCC of nose. Results of IHC by anti-L1 antibody demonstrated in Table 8 show positive staining on tumor tissues including Squamous cell carcinoma (SCC) of upper jaw, SCC of cheek, SCC of larynx, and SCC of left gingival while negatively staining of IHC by anti-L1 antibody including little tissue of SCC of larynx, SCC of nasal cavity, Carcinoma sarcomatoids of left ethmoid sinus, and SCC of left gingiva. These results indicate HPV proteins expressed and distributed in different part of tumors from different organs.

Staining of cytoplasm is found most distinguishable in tumor cells compared to its corresponding normal cells. These data suggest the IHC staining by E6 or E7 monoclonal antibody is specific in the cytoplasm of tumor cells. In addition, the expression of the L1 viral protein in the tumor cells is also detected in various organs/tissues at the various stages of head and neck cancer. However, the IHC assay sensitivity of about 56% by the Anti-L1 antibody is much lower than assay sensitivity of 100% by the Anti-E7 antibody and Anti-the E6 antibody. These data suggest that detection of E6 or E7 oncoproteins are more relevant to cancer than the detection of the viral capsid protein in head and neck cancer. Previous studies have shown HPV detection of head and neck cancers by DNA test. Together, the results support previous study that HPV-16 E6 and E7 are actively transcribed in most of the tonsillar carcinomas that have been analyzed and all tonsillar tumors expressed E7 encoding HPV-33 E6*I mRNA independent of the physical state of the virus. Therefore, E6 and E7 oncoproteins can better serve as biomarkers for detection of head and neck cancers.

Bladder cancer: As another example, results demonstrate that HPV L1 viral protein can be detected in the tumor cells of urothelial tissues of bladder cancer by IHC staining, showing HPV present in urothelial carcinoma, transitional cell carcinoma and bladder adenocarcinoma with positive rates varying from 95%, 71% and 33%, respectively. HPV IHC on bladder cancer tissues using anti-E6 and anti-E7 mouse monoclonal antibody demonstrate HPV E6 and E7 oncogenic proteins can be detected in the tumor cells of urothelial tissues of bladder cancer by IHC. The nucleus and/or cytoplasmic staining of tumor cells by Anti-E6, or Anti-E7 antibody confirms HPV oncogenic proteins present in situ in the tumor cells of bladder cancer. Data indicated HPV E6 and E7 oncoproteins can be detected in situ present in TCC with positive rates of 19% and 26%, respectively. A total of 19 TCC HPV DNA positive tissues (confirmed by PCR using L1 primer) were further analyzed by performing HPV E6 or E7 RNA and/or HPV IHC assays. Three out of 18 (14%) and 4 out of 19 (19%) show positive staining by IHC using anti-HPV E6 and anti-HPV E7 antibody, respectively. Among the four IHC/HPV E7 positive samples, two are HPV16 E7 RNA positive confirmed by RT-PCR while the other two were not tested yet. Among the three IHC/HPV E6 positive samples, one is HPV16 E6 RNA positive confirmed by RT-PCR while the other 2 were not tested yet. These data suggest correlation of E6 and E7 oncogenes expressed at the RNA and protein level.

In summary, HPV E6, E7 and L1 proteins expressed in the tumor cells of bladder cancer can be detected by IHC with positive rate of 17%, 26%, and 81% using anti-E6, anti-E7, and anti-L1 antibody, respectively. The IHC positive rate of E6 and E7 expression found in bladder cancer is much lower than found in cervical cancer. Data suggest that, in addition to HPV infection and/or overexpression of E6 E7 oncoproteins, other factors may have contributed to the progression and development of bladder cancer. Most of the E6 or E7 IHC positive samples are found in grade 1 and grade 2, with very few found in grade 3 of TCC. Comparing HPV DNA/RNA and IHC assays, three samples found to be HPV DNA, RNA and IHC E6/E7 positive were diagnosed as grade 2 of TCC; four samples were found to be HPV DNA/RNA positive, and IHC E6/E7 negative samples were diagnosed as grade 3 of TCC. HPV E6 E7 oncoproteins can be used for early detection of transforming TCC and may serve as potential biomarkers for early stage stages of HPV infected bladder cancers. More studies with more cases are mandatory.

Ovarian cancer: As another example, various stages of ovary tissues were used to demonstrate the expression of the E6 or E7 oncoprotein in the tumor cells of serous papillary cystadenocarcinoma of ovarian cancers using the monoclonal anti-E6 and anti-E7 antibody provided in this invention. The staining results indicate localization of the E6 or E7 proteins expressed in the cytoplasm of tumor cells, but not in the adjacent normal cells, nor stroma cells. The expression of the L1 viral protein is also detected in the tumor cells from the tissue samples at various ovarian cancer stages. The results of the assay sensitivity for an Anti-E7 antibody show about 33% (2 out of 6) for serous papillary cystadenocarcinoma (SPC) with 100% specificity using normal adjacent tissues as negative control. The results of assay sensitivity for an Anti-E6 antibody were at about 60% (3 out of 5) for serous papillary cystadenocarcinoma (SPC) with 100% specificity using normal adjacent tissues as negative control. The results of assay sensitivity for an Anti-L1 antibody were at 64% (7 out of 11) for serous papillary cystadenocarcinoma (SPC) and 17% (1 out of 6) for other carcinoma with 100% specificity using normal adjacent tissues as negative control. The positive predictive value (PPV) is at about 100% and negative predictive value (NPV) is at about 31%.

It's worth noting that HPV is associated with serous papillary cystadenocarcinoma (SPC) more often than other ovarian cancer, as data demonstrated by HPV IHC using anti-E6, anti-E7 and anti-L1 antibody as data shown in Table 13-16. HPV IHC using anti-E6 or anti-E7 detects most of SPC, but not endometrioid adenocarcinoma. Using anti-L1 antibody, there is about 64% (7 out 11) of SPC samples that are HPV positive as compared to only about 17% (1 out of 6) of other non-SPC carcinoma. The 6 non-SPC ovary carcinomas include endometrioid adenocarcinoma (3), clear cell carcinoma (2), and necrosis tissue (1). The only one out of the 6 non-SPC that was demonstrated as positive on HPV L1 is endometrioid adenocarcinoma. Average assay sensitivity of ovary cancer for IHC L1 is about 46% (8 out of 17). However, the assay sensitivity obtained herein is much higher sensitivity than any previous reported connection between HPV and serous papillary cystadenocarcinoma, having about 10% reported HPV DNA positive rate for serous papillary cystadenocarcinoma. This HPV IHC assay provides a more robust tool to detect HPV in ovarian cancer, and to access the risk of cancer progression by HPV infection.

Detection of HPV DNAs, genomes, early viral proteins, late viral proteins, oncoproteins, and/or capsid proteins from various HPV genotypes can be performed by the method and detection assays as described herein and can be very useful in general clinical screening for HPV infection. Detection of HPV antibodies and/or oncoproteins by immunological assays can be used in early clinical screening for HPV infection and general diagnosis for HPV associated cancers and can be performed in a single rapid test or in a multiplexed test. Comparative detection of altered levels of HPV proteins and host proteins can be performed in the same or different assays. It can also be used in diagnosing HPV-associated carcinomas with epithelial cell abnormalities induced by HPV infection, pre-malignant and malignant HPV-associated epithelial cell lesions, and those at risk of developing HPV-associated carcinoma and adenocarcinoma. The methods as described herein can be used independently or as adjunct histological tests, and the results thereof can be compared for follow-up patient management.

Developing appropriate assays, such as HPV immunoassays, is needed for detection of HPV oncoproteins or biomarkers for various cancers associated with HPV infection. The presence of E6/E7 oncoproteins could be evidence to indicate high progression risk of various types of cancer. Embodiments of the invention provided useful antibodies for in situ detection of HPV L1, E6, and E7 proteins in various cancers and carcinomas. The antibodies and assays, as described herein, are useful for detecting HPV oncoproteins as cancer biomarkers, screening for various HPV associated cancers, and/or assessing the risk for malignant transformation into these HPV associated cancers. As an example, it is possible that male subjects can be HPV carriers to transmit HPV to their partners. A robust test for HPV detection as described in this invention provides promise to develop assays in different formats for detection of HPV in different tissues for various HPV associated cancers.

The one or more immunological assays as developed herein lend themselves to the high quality and properly purified recombinant proteins encoded by HPV early and late genes, as well as high quality polyclonal and monoclonal antibodies, resulting in immunological assays with very high sensitivity and specificity for screening HPV infection. The one or more immunological assays include, but are not limited to, protein chip assays, antigen assays for papillomavirus proteins, antibody assays for antibodies against papillomavirus proteins, ELISA assays for papillomavirus immunocomplexes, radioimmunoprecipitation assays, rapid membrane immunochromatographic assays, rapid stick immunochromatographic assays, immunohistochemistry for tissues and/or cervical cells among others, and immunocytological assays followed by flow cytometry. The one or more immunological assays may be non-invasive with minimal or no additional instrument required. The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art.

EXAMPLES

1. The Anti-HPV Antibody

HPV recombinant proteins can be any kind of HPV viral proteins, HPV proteins of early genes and/or late genes, including, but not limited to, E2, E6, E7, L1, L2 and can be from various HPV types. One aspect of the invention provides recombinant proteins, such as recombinant hybrid proteins containing a partial sequence or a full length sequence of HPV oncogenic proteins. For example, full-length E6, E7, and/or L1 polypeptide sequences have been found very difficult to obtain and purify due to undesirable aggregation during protein purification, protein instability, low levels of expression, and low immunogenic responses of purified proteins. For example, many early E6 oncoproteins contain many cysteine amino acids and thus the correct topography of the E6 oncoproteins requires the proper formation of many disulfide bonds. In addition, it was known that certain immunological assays using small peptides of early E6 and E7 proteins result in extremely low assay specificity and sensitivity and, thus, are unsuitable as commercialized diagnostic tools.

HPV recombinant proteins were produced to use as immunogens for generating antiserum, and screening of monoclonal antibody from hybridoma cell lines: Cloning and production of various recombinant proteins include genes encoded by HPV16 E6 and HPV18 E6 gene, HPV16 E7 and HPV18 E7 gene, HPV16 L1 and HPV18 L1 gene. To provide the recombinant proteins mostly in (or close to) their native forms with much desirable conformation, recombinant HPV E6, E7 or L1 proteins expressed in *E. coli* was purified from soluble fraction, then concentrated, and dialyzed with PBS to be used as immunogen. Immunization of mice and fusion was done by standard procedure to select clones that met our screening criteria on ELISA. Each hybridoma cell line was grown in tissue culture and injected to mice for ascites production. Ascites were collected, isotyped, and purified by Protein G column for use in HPV immunoassays.

For example, a number of samples from various organs are tested in an immunohistochemistry (IHC) assay concurrently as a tissue microarray format using a monoclonal antibody to detect HPV proteins from a variety of HPV types. In addition, the monoclonal antibodies generated using methods of the invention are useful to detect infection by oncogenic HPVs, such as infection by high risk HPV types and/or low risk HPV types. As an example, antibodies raised against a recombinant protein HPV16 E6 oncoprotein generated by the method of invention are able to recognize E6 proteins present inside the cells of clinical samples due to single or multiple HPV infection, and react with E6 proteins from high risk HPV types (such as HPV-16, HPV-18, HPV-31, HPV-33, HPV-45, HPV-52, HPV-58, etc.) or low risk HPV types (HPV-6, etc). In addition, a single anti-E6 monoclonal antibody can detect multiple HPV infection in a clinical sample, having two or more HPV types, such as the combinations of HPV-16, HPV-18, HPV-51, HPV-52, HPV-58, among others.

As another example, antibodies raised against a recombinant protein HPV16 L1 capsid protein generated by the method of invention are able to recognize L1 proteins present inside the cells of clinical samples due to HPV infection, and react with L1 proteins from high risk HPV types (such as HPV-16, HPV-18, HPV-31, HPV-33, HPV-45, HPV-52, HPV-58, etc.) or low risk HPV types (HPV-6, etc). In addition, a single anti-L1 monoclonal antibody can detect multiple HPV infections in a clinical sample, having two or more HPV types, such as the combination of HPV-16, HPV-18, HPV-51, HPV-52, HPV-58, among others.

2. Immunohistochemisty (IHC)

Sample preparation: Paraffin tissue blocks sectioned into 4 microns were placed on slides and baked at 60° C. overnight. Deparaffin/hydrate sections were unmasked followed by standard IHC staining procedures. Purified monoclonal antibody against HPV proteins were diluted to use as the primary antibody. Staining procedure was followed by secondary antibody solution, washing, and further followed by appropriate substrate reagent to each section. As soon as the sections were developed, the slides were immered in deionized $H_2O$. The sections were counterstained with Hematoxylin, dehydrated, and the coverslips were mounted.

Once the tissues were processed and fixed, the Immunohistochemistry (IHC) assay was performed by boiling the tissues on the slide with antigen retrieval buffer for a period of time. The slides were then cooled down to room temperature, blocked with pre-antibody blocking solution for a period of time, then incubated with the HPV antibodies. The slides were then washed 3 to 5 times with PBS or $H_2O$, or other solution to get rid of any unbound HPV antibody. Then the slides were incubated with the secondary antibody, for example, anti-mouse IgG HRP, followed by appropriate substrate for detection. As an example, DAB is oxidized in the presence of peroxidase and hydrogen peroxide resulting in the deposition of a brown, alcohol-insoluble precipitate at the site of enzymatic activity. The precipitate may range in color from a light golden brown to dark golden brown depending upon the amount of enzyme present. The golden brown precipitate viewed under a microscope indicates the specific binding of HPV antibodies with HPV proteins present in the cells. The assay can be performed at room temperature or higher temperature to accelerate the binding reaction. This IHC assay can be performed manually, or by IHC automation, thus it can be a powerful tool to detect HPV infection and HPV oncoproteins in situ localization in the epithelium cells from various tissues including, but not limited to, cervical, colon, lung, bladder, head and neck, ovarian, etc.

For the dysplasia or tumor cells identified, HPV IHC staining may provide additional information for status of HPV infection, stages of diseases, and/or expression of HPV oncoproteins. Therefore, HPV IHC staining assay is very useful as a confirmatory test. In addition, overexpression of HPV E6 and E7 oncoproteins in various stage of cervical dysplasia may indicate progression of CIN and/or cervical cancer development.

In addition to cervical cancer, IHC staining for other cancers like bladder cancers, head and neck cancers, and ovarian cancers were investigated in this invention. The images of each dot on the other tissue microarray slides were viewed and stained cells are examined under microscope. Areas of tumor cells were looked up to find the cells stained, with staining intensity of score 0-3. Adjacent normal epithelium or normal tissue away from its corresponding tumors was also scored to use as internal control of the assay. Stained intensity score 1 or above was used as cut off to determine positive or negative of the assay. All data were shown in Tables 1-6 for bladder cancers, Tables 7-11 for head and neck cancers, and Tables 12-16 for ovarian cancers.

3. HPV Detection in Bladder Cancer

The prevalence of HPV DNA in cancers of the urinary bladder varies a lot depending on the techniques applied in the studies. For transitional-cell carcinomas using PCR-based studies, HPV was detected in 3-80% of the samples. Only genital (low- and high-risk) HPV types have been assessed in these studies and HPV 16 and 18 were detected most frequently. Relatively few studies addressed HPV positivity in squamous-cell carcinoma of the bladder using PCR.

According to the International Expert Group, that evidence of the etiological role of HPV for bladder cancer is currently inadequate. There are fewer studies on the association between HPV and cancers at sites other than the cervix, and the number of cases reported is much smaller. To allow for a preliminary assessment of the association between HPV and these cancers, a wider variety of techniques and methods should be considered to be compared in studies. In this invention, we use HPV IHC method to in situ detect the presence of HPV proteins in bladder cancer tissues.

High rate of HPV positivity in studies suggests that other sexually transmissible viruses may play some roles in development and progression of transitional cell carcinoma of the bladder. There may be a high synergism between Human Papillomaviruses type 16 and 18 (HPV 16, HPV 18), Epstein-Barr virus (EBV), cytomegalovirus (CMV) and herpes simplex virus type 2 (HSV-2) and bladder carcinogenesis. In this regard, further investigation with a large number of patients seems to be required. Public education regarding HPV transmission and high-risk behavior may be helpful for decreasing the incidence of urogenital malignancies. Males may be carriers of oncogenic HPVs and male partners may markedly contribute to the risk of developing cervical cancer in their female partners.

HPV may have a great role in the progression of transitional cell carcinoma (TCC) by inactivation of the tumor suppressors or other unknown mechanisms. Previous studies showed the presence of HPV correlated with malignancy of urothelium transformation, but some reported contradictory results. In this regard, more sensitive detection of HPV in bladder cancers is required to demonstrate the association of HPV and cancer progression in TCC. Detecting expression and localization of HPV oncoproteins in different stages of bladder cancer will help in understanding the mechanism. In this invention, we detect HPV proteins in TCC by immunohistochemistry (IHC) using our novel antibodies to HPV E6, E7 and L1 proteins. We also compared HPV E6, E7 oncoprotein expression with HPV DNA and HPV mRNA transcript in TCC specimen.

The bladder cancer (BC) specimen: Tissue microarrays (TMA) containing various stages of bladder cancer and its adjacent normal tissues were obtained from a commercially available vendor. Additional HPV typed TCC specimens performed in this study were obtained from patients of N.N. Blokhin Cancer Research Center or P.A. Hertzen Research Institute of Oncology with consent. DNA isolated from frozen tissues was screened by PCR using primer GP 5/6 and My 09/11 for L1 region. The amplification products obtained by the My 09/11 primers were subjected to restriction analysis to determine HPV types 6, 11, 16, 18, 31, 33 and 35. RNA preparation was used to perform RT-PCR with random hexanucleotide primers ("Lytekh", Russia) and Super Script II reverse transcriptase ("Invitrogene") according to the instructions of the manufacturer. Analysis of the HPV16 E7 transcripts was performed using primers: sense, 5'-CGG ACA GAG CCC ATT ACA AT-3'; antisense, 5'-GAA CAG ATG GGG CAC ACA AT-3' for amplification product length of 144 bp.

Figure 1B:
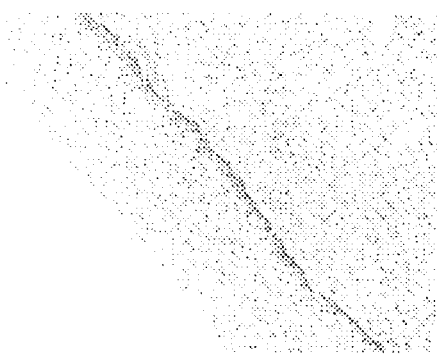
Figure 1C:
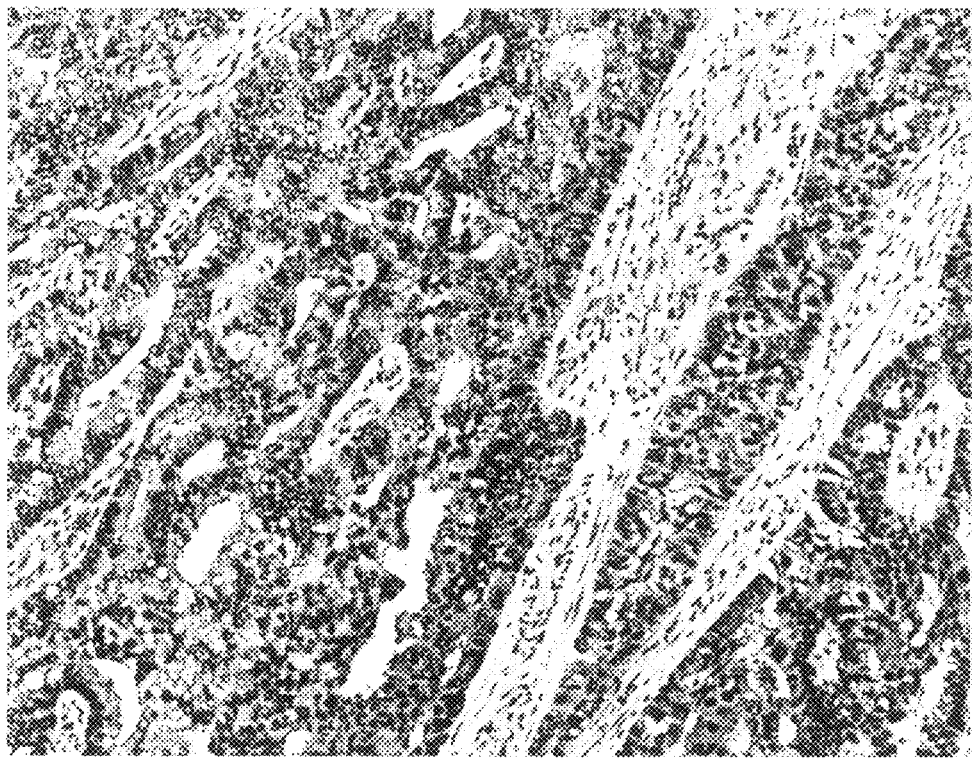
FIG. 1C-1D: Images of IHC using anti-E7 antibody on cervical cancer and its adjacent normal tissue.
Figure 1D:

1). HPV IHC on cervical cancer tissues: There is limited study reported for detection of HPV proteins in bladder cancer. To perform HPV IHC assay on bladder cancer, cervical cancer tissues were used as positive control to demonstrate detection of HPV proteins in situ using our novel mouse monoclonal anti-HPV antibodies. FIGS. 1A-1C show IHC staining of cervical cancer tissues using mouse monoclonal anti-HPV L1, anti-HPV E6, and anti-HPV E7.antibody, respectively. Results indicate that HPV proteins are present in the nucleus and/or cytoplasm of dysplasia cells from most of the samples tested. At the cellular level, HPV proteins can be detected in the nucleus and cytoplasm, but not in the membrane of a cell. The staining of tumor cells results in focused staining and diffused staining as well.

Figure 2A:
FIG. 2A-2C: Images of IHC using anti-HPV-L1 antibody on bladder cancer tissue samples.
Figure 2B:
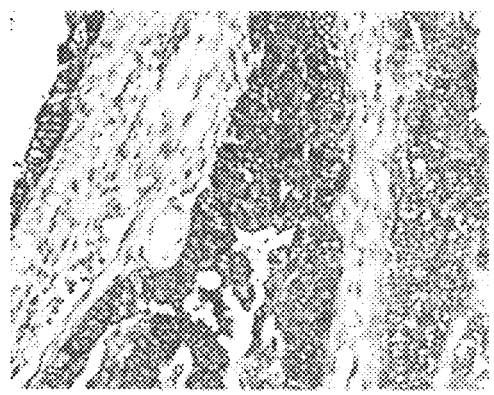
Figure 2C:
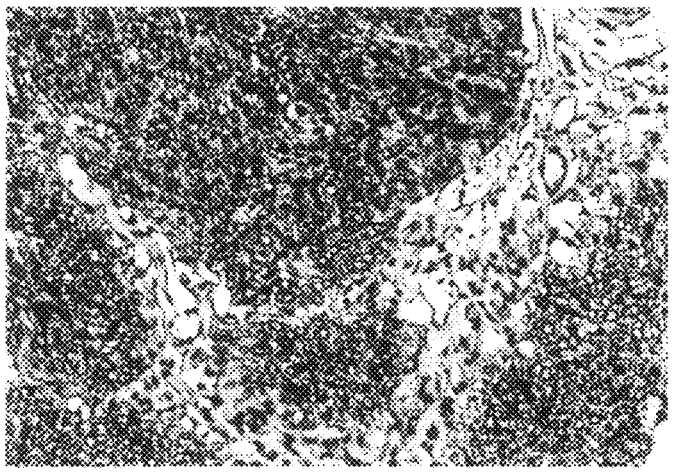

2). HPV IHC on bladder cancer tissues using anti-HPV L1 antibody: To demonstrate HPV IHC assay on BC samples, TMA containing various BC samples were used to perform IHC assay using a mouse monoclonal anti-HPV L1 as results demonstrated in FIG. 2A-2C and summarized in Table 1. FIG. 2A shows representative images of IHC staining of urothelial carcinoma of bladder tissue demonstrated by a mouse monoclonal Anti-HPV-L1. FIG. 2B shows representative images of IHC staining of another urothelial carcinoma of bladder tissue demonstrated by the same Anti-HPV-L1 antibody at high power magnification. FIG. 2C shows representative images of IHC staining of another urothelial carcinoma with glandular metaplasia demonstrated by the same mouse monoclonal Anti-HPV-L1. The results indicate that HPV L1 viral protein can be detected in the tumor cells of urothelial tissues of bladder cancer by IHC staining using a mouse monoclonal anti-HPV L1 antibody.

The images of each dot on the tissue microarray slides were examined and scored with percentage and staining intensity by certified pathologist. Adjacent normal epithelium or normal tissue away from its corresponding tumors was also scored. Stained percentage over 10% or intensity score 1 or above was used as cut off for assay positivity. Table 1 shows summary of IHC data from TMA, containing bladder samples including urothelial carcinoma (20), transitional cell carcinoma (14), adenocarcinoma (3), and normal urocystic tissue (6). As data indicated, nucleus and/or cytoplasmic staining are found in most clinical samples of tumor cells stained by an Anti-L1 antibody. These results confirmed that HPV-protein-specific IHC staining of tumor cells in urothelial cancer. The IHC staining results indicated that HPV L1 proteins can be detected in situ present in urothelial carcinoma, transitional cell carcinoma and bladder Adenocarcinoma. These results confirmed that HPV-protein-specific staining of tumor cells. Staining of cytoplasm is found most distinguishable in dysplasia or tumor cells compared to its corresponding normal cells.

TABLE 1

IHC staining results (stain intensity score; 0-3) for biopsy samples from urothelial carcinoma (20 samples) and adjacent normal tissue (4 samples, as negative controls) using monoclonal Anti-HPV-L1 antibody.

| No. | organ | pathology | grade | type | Anti-L1 Ab |
|---|---|---|---|---|---|
| 1 | Bladder | Urothelial carcinoma (UCC) | I | Malignant | 3+ |
| 2 | Bladder | UCC | I | Malignant | 3+ |

TABLE 1-continued

IHC staining results (stain intensity score; 0-3) for biopsy samples from urothelial carcinoma (20 samples) and adjacent normal tissue (4 samples, as negative controls) using monoclonal Anti-HPV-L1 antibody.

| No. | organ | pathology | grade | type | Anti-L1 Ab |
|---|---|---|---|---|---|
| 3 | Bladder | UCC with glandular metaplasia | II | Malignant | 3+ |
| 4 | Bladder | UCC with glandular metaplasia | II | Malignant | 3+ |
| 5 | Bladder | UCC | I | Malignant | 2+ |
| 6 | Bladder | UCC | I | Malignant | 2+ |
| 7 | Bladder | UCC | I | Malignant | 0 |
| 8 | Bladder | UCC | I | Malignant | 3+ |
| 9 | Bladder | UCC | I | Malignant | 3+ |
| 10 | Bladder | UCC | I | Malignant | 3+ |
| 11 | Bladder | UCC | II | Malignant | 3+ |
| 12 | Bladder | UCC | II | Malignant | 2+ |
| 13 | Bladder | UCC | III | Malignant | 3+ |
| 14 | Bladder | UCC | III | Malignant | 3+ |
| 15 | Bladder | UCC | III | Malignant | 3+ |
| 16 | Bladder | UCC | III | Malignant | 3+ |
| 17 | Bladder | UCC | II | Malignant | 3+ |
| 20 | Bladder | UCC | III | Malignant | 3+ |
| 21 | Bladder | adjacent bladder tissue of No. 01 | — | Normal | 0 |
| 22 | Bladder | adjacent bladder tissue of No. 01 | — | Normal | 0 |
| 23 | Bladder | adjacent bladder tissue of No. 03 | — | Normal | 0 |
| 24 | Bladder | adjacent bladder tissue of No. 03 | — | Normal | 0 |

Another tissue microarray containing 19 bladder samples including transitional cell carcinoma (14), adenocarcinoma (2), normal urocystic tissue (2) and skin malignant melanoma (1) was also tested using anti-HPV-L1 antibody (data shown in table 3). Combined data from the two tissue microarray, Table 2 shows summary of the IHC staining results of bladder cancer tissues using an anti-HPV-L1 antibody.

TABLE 2

Summary of the IHC staining results of bladder cancer tissues using an Anti-L1 mouse monoclonal antibody

| | Bladder Cancer | | | Normal |
|---|---|---|---|---|
| | Urothelial carcinoma | Transitional cell carcinoma | Adenocarcinoma | normal urocystic tissue |
| Anti-L1 antibody | 95% (19/20) | 71% (10/14) | 33% (1/3) | 33% (2/6) |

Figure 3A:
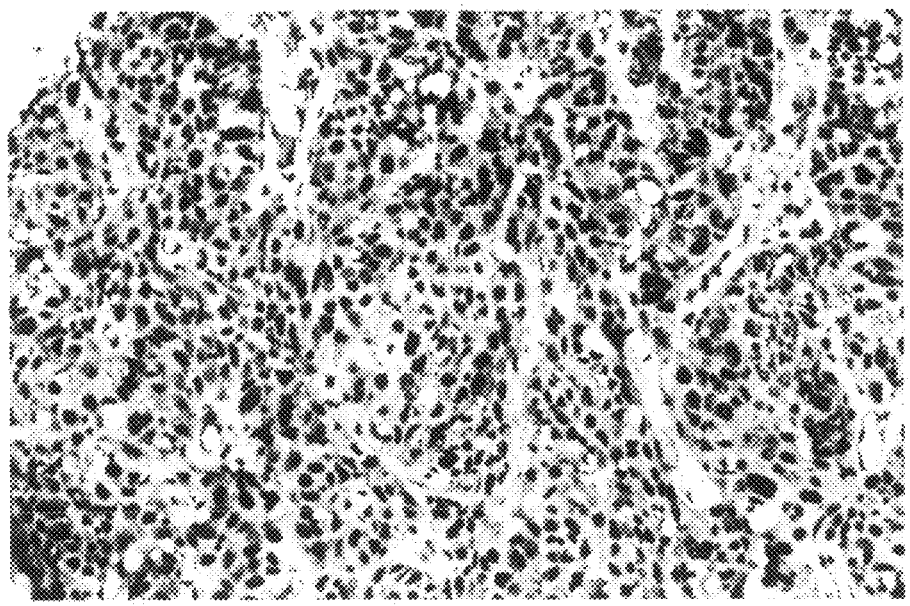
FIG. 3A-3B: Images of IHC using anti-HPV-E6 antibody on bladder cancer tissues.
Figure 3B:
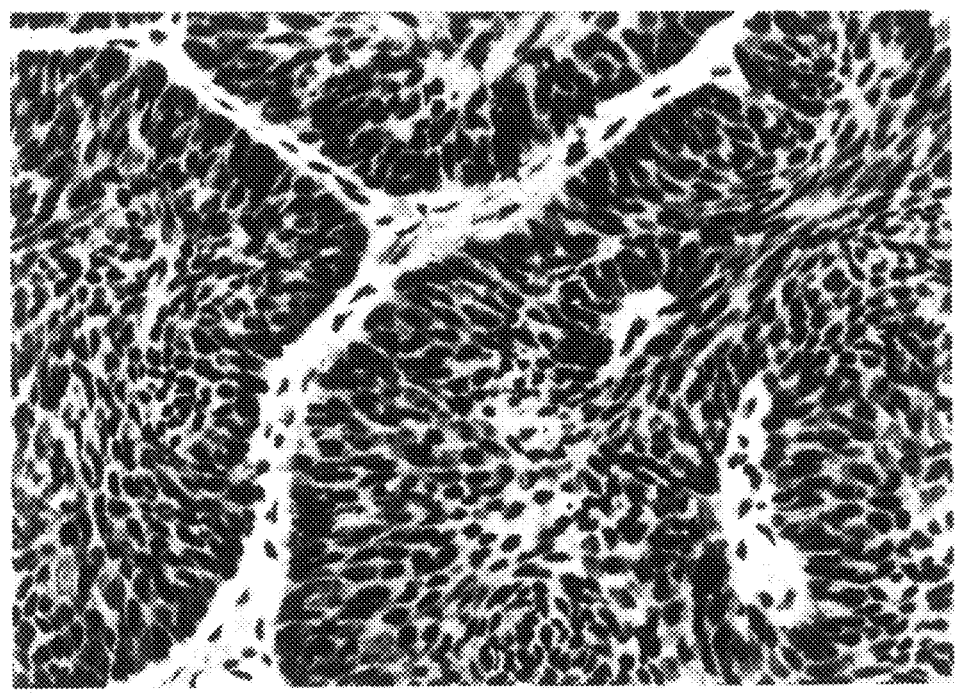
Figure 3C:
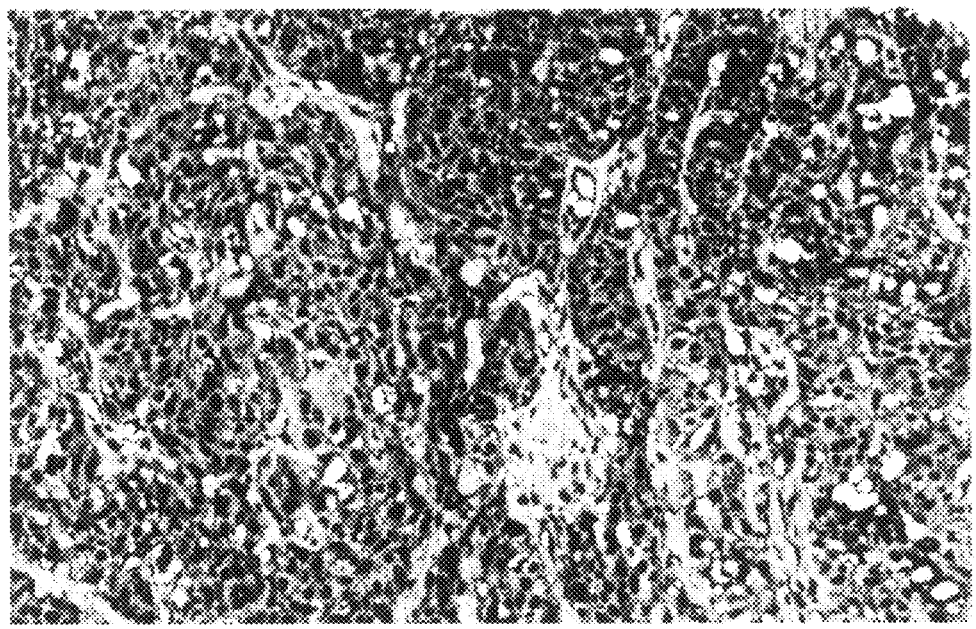
FIG. 3C-3D: Images of IHC using anti-HPV-E7 antibody on bladder cancer tissues.
Figure 3D:

2). HPV IHC on bladder cancer tissues using anti-E6 and anti-E7 mouse monoclonal antibody:

As another example, various stages of urothelial tissues from bladder cancer were used to show the expression of the E6 or E7 oncoprotein in the tumor cells. To demonstrate detection of HPV E6 and E7 oncogenic proteins on BC samples, TMA containing various BC samples were used to perform IHC assay using a mouse monoclonal anti-HPV E6, or anti-HPV E7 antibody. As results demonstrated, FIG. 3A-3B shows representative images of IHC staining of transitional cell carcinoma of bladder tissue using a mouse monoclonal HPV E6 antibody. FIG. 3C-3D shows IHC staining of transitional cell carcinoma of bladder tissue using a mouse monoclonal Anti-E7 antibody. FIG. 3D shows representative images of IHC staining of adenocarcinoma of bladder tissue using the same mouse monoclonal anti-HPV E7 antibody.

These results demonstrate HPV E6 and E7 oncogenic proteins can be detected in the tumor cells of urothelial tissues of bladder cancer by IHC. The nucleus and/or cytoplasmic staining of tumor cells by Anti-E6, or Anti-E7 antibody confirms HPV oncogenic proteins present in situ in the tumor cells of bladder cancer.

Table 3 contains data from 19 bladder samples including transitional cell carcinoma (14), adenocarcinoma (2), normal urocystic tissue (2) and skin malignant melanoma (1). IHC score for staining of cytoplasm, and/or nucleus followed by the intensity of staining with an anti-HPV-E7 antibody or an anti-HPV-E6 antibody were shown. As data shown in Table 3, nucleus and/or cytoplasmic staining are found in clinical samples of tumor cells stained by an Anti-E7 antibody, an Anti-E6 antibody or an anti-L1 antibody. These results confirm HPV-protein-specific IHC staining of tumor cells. However, most of staining by anti-L1 antibody (8 out 10 anti-L1 positive samples) is found in cytoplasm compared to only 2 out of 10 found in nucleus staining by anti-L1 antibody.

TABLE 3

Monoclonal anti-HPV E6 or E7 or L1 antibody IHC staining results (stain intensity score; 0-3) for biopsy samples from bladder cancers including transitional cell carcinoma (14) and adenocarcinoma (2) compared to normal urocystic tissue (2) as negative controls.

| No. | pathology | grade | notes | type | Anti-E7 antibody | Anti-E6 antibody | Anti-L1 antibody |
|---|---|---|---|---|---|---|---|
| 1 | Transitional cell carcinoma (TCC) | 1 | T1N0M1 | Malignant | 0 | 0 | 0 |
| 2 | TCC | 1 | T2N0M0 | Malignant | — | 0 | 1+ |
| 3 | TCC | 1 | T2N0M0 | Malignant | 0-1 | 1+ | 2+ |
| 4 | TCC | 1 | T1N0M0 | Malignant | 1+ | 1+ | 2+ |
| 5 | TCC | 1 | T1N0M0 | Malignant | 1+ | 0 | 1+ |
| 6 | TCC | 1 | T1N0M0 | Malignant | 0 | 0 | 0 |
| 7 | TCC | 1 | T1N0M1 | Malignant | 0 | 0 | 0 |
| 8 | TCC | 2 | T3N0M0 | Malignant | 0 | 0 | 0 |
| 9 | TCC | 2 | T3N0M0 | Malignant | 0 | 0 | 1+ |
| 10 | TCC | 2 | T2N0M0 | Malignant | 0 | 0 | 1+ |
| 11 | TCC | 2 | T2N0M0 | Malignant | 0 | 0 | 1+ |
| 12 | TCC | 3 | T2N0M0 | Malignant | 1-2+ | 0-1 | 1+ |
| 13 | TCC | 3 | T2N0M0 | Malignant | 1-2+ | 0-1 | 1+ |
| 14 | TCC | 3 | T1N0M0 | Malignant | 0 | 0 | 0 |
| 15 | Adenocarcinoma (ADC) | 1 | T3N0M0 | Malignant | 0 | 0 | 1+ |
| 16 | ADC | 1 | T3N0M0 | Malignant | 0-1 | 0 | 0 |
| 17 | ADC | 1 | T3N0M0 | Malignant | — | 0 | 0 |
| 18 | Normal urocystic tissue | — | — | Normal | 0 | 0 | 2+ |
| 19 | Normal urocystic tissue | — | — | Normal | 0 | 0 | 2+ |

TABLE 4

Summary of the IHC staining results from Table 3 for an anti-E7 antibody and anti-E6 antibody on bladder cancer samples

| | Bladder Cancer | | Normal |
|---|---|---|---|
| | Transitional cell carcinoma | Adenocarcinoma | normal urocystic tissue |
| Anti-E7 antibody | 28% (4/13) | 0% (0/3) | 0% (0/2) |
| Anti-E6 antibody | 14% (2/14) | 0% (0/3) | 0% (0/2) |

4. Analysis of HPV DNA/RNA and HPV oncogenic protein expression in bladder cancer tissues: To analyze HPV DNA/RNA and HPV oncoprotein expression on BC samples, 21 TCC HPV DNA positive tissues (confirmed by PCR using L1 primer) and 4 normal urothelial tissues from non oncological patients were further analyzed by performing HPV E7 RNA and/or HPV IHC assays. Four out of 19 (21%) and 3 out To summarize data from Table 3, Table 4 shows assay sensitivity of about 28% (4 out of 14) and about 0% (0 out of 2) using an Anti-E7 antibody for detecting bladder transitional cell carcinoma (TCC) and bladder Adenocarcinoma (ADC), respectively, with about 100% specificity for normal urothelial as negative control; about 100% of positive predictive value (PPV) and about 14% of negative predictive value (NPV) were also obtained.

For detecting HPV E6 protein in situ in bladder cancer tissues as shown in Table 4, assay sensitivity of about 14% (2 out of 14) and about 0% (0 out of 2) using an Anti-E6 antibody for detecting bladder transitional cell carcinoma (TCC) and bladder Adenocarcinoma (ADC), respectively, with about 100% specificity using normal urothelial or skin melanoma as negative control; about 100% of positive predictive value (PPV) and about 12% of negative predictive value (NPV) were also obtained.

of 18 (17%) are positive staining by IHC using anti-HPV E7 and anti-HPV E6 antibody, respectively. These data seem to correlate to our overall positive rate of IHC assay shown in Table 4. Among the four IHC/HPV E7 positive samples, two are HPV16 E7 RNA positive confirmed by RT-PCR while the other two were not tested yet. Among the three IHC/HPV E6 positive samples, one is HPV16 E6 RNA positive confirmed by RT-PCR while the other 2 were not tested yet. These data suggest correlation of E6 and E7 oncogenes expressed at the RNA and protein level. There are four TCC samples that are positive for both HPV DNA and RNA, but IHC negative stained by anti-E6 or anti-E7 antibody. These four HPV DNA/RNA positive, IHC negative samples were diagnosed grade 3 while those HPV DNA/RNA and IHC positive samples are diagnosed as grade 2 of TCC. These data suggest that E6 E7 oncoproteins can be detected in grade 2 as early detection of transformation for TCC and may serve as potential biomarkers for HPV infected bladder cancers. More studies with more cases are required.

To demonstrate the specific detection of E6 E7 proteins in bladder cancer, an additional 12 cases of tissues from various organs were also tested on IHC by anti-E6 or anti-E7 antibody. To summarize the cases tested by IHC assay for detection of E6 and E7 proteins in bladder cancer, Table 5 shows combined IHC data from Table 4 containing transitional cell carcinoma (14), adenocarcinoma (3), normal urocystic tissue (2) and 18 TCC specimen from Russia and 12 normal tissues from various organs. These data also indicate higher positive rate of IHC using anti-HPV E7 antibody detecting E7 proteins in TCC (transitional cell carcinoma) compared to IHC using anti-HPV E6 antibody detecting E6 proteins in TCC. More cases to be studied are mandatory. Table 5 shows summary of IHC data indicating HPV E7 and E6 oncoproteins can be detected in situ present in TCC with positive rates of 26% and 16% respectively.

To demonstrate the detection of HPV proteins on bladder cancer and to compare the expression of HPV viral proteins (L1 as an example) and oncoproteins (E6, E7 as example), Table 6 shows summary of IHC assay sensitivity and specificity using anti-HPV L1, E7, and E6 antibody. About 81% of bladder cancer shows HPV L1 positive while about 23% and 14% shows positive staining by anti-HPV E7 and anti-HPV E6 antibody respectively. These IHC data correlate with HPV DNA/RNA test on bladder cancer that about 33% (7 out of 21) of HPV DNA positive TCC specimens show positive HPV E7 mRNA. However, HPV IHC assays are more robust compared to HPV DNA or RNA by PCR, which involves many steps in target nucleic acid amplification and issues of contamination among samples. It is advantageous to use the HPV IHC assays provided in this invention to detect the association of HPV with bladder cancer and the role of HPV in transformation and malignancy of bladder cancers.

TABLE 5

Summary of the IHC staining results of bladder cancer tissues using an Anti-E7 and anti-E6 mouse monoclonal antibody.

| | Bladder Cancer | | Normal tissue | |
|---|---|---|---|---|
| | Transitional cell carcinoma | Adeno-carcinoma | normal uro-cystic tissue | various organ |
| Anti-E7 antibody | 26% (8/32) | 0% (0/3) | 0% (0/6) | 8% (1/12) |
| Anti-E6 antibody | 16% (5/32) | 0% (0/3) | 0% (0/6) | 8% (1/12) |

TABLE 6

Summary of the HPV IHC assay for bladder cancer samples

| IHC | sensitivity (Bladder Cancer stained positively) | Specificity (Normal tissue stained negatively) |
|---|---|---|
| Anti-L1 | 81% (30/37) | 67% (2/6) |
| Anti-E7 | 23% (8/35) | 94% (1/18) |
| Anti-E6 | 14% (5/35) | 94% (1/18) |

The invention described herein provides a robust tool for detection of HPV in bladder cancer tissues. In summary: 1). HPV E6, E7 and L1 proteins expressed in the tumor cells of bladder cancer can be detected by IHC with positive rate of 14%, 23%, and 81% using anti-E6, anti-E7, and anti-L1 antibody, respectively, as shown in Table 6. 2). The IHC positive rate of E6 and E7 expression found in bladder cancer is much lower than found in cervical cancer. Data suggest that in addition to HPV infection and/or overexpression of E6 E7 oncoproteins, other factors may have contributed to the progression and development of bladder cancer. 3). Most of E6 or E7 IHC positive samples are found in grade 1 and grade 2, very few found in grade 3 of TCC. 4). Comparing HPV DNA/RNA and IHC assay, three samples found to be HPV DNA, RNA and IHC E6/E7 positive were diagnosed as grade 2 of TCC; four samples found to be HPV DNA/RNA positive, IHC E6/E7 negative were diagnosed as grade 3 of TCC. 5). HPV E6 E7 oncoproteins can be used for early detection of transforming TCC and may serve as potential biomarkers for early stage of HPV infected bladder cancers. More studies with more cases are required.

4. HPV Detection in Head and Neck Cancer

Figure 4A:
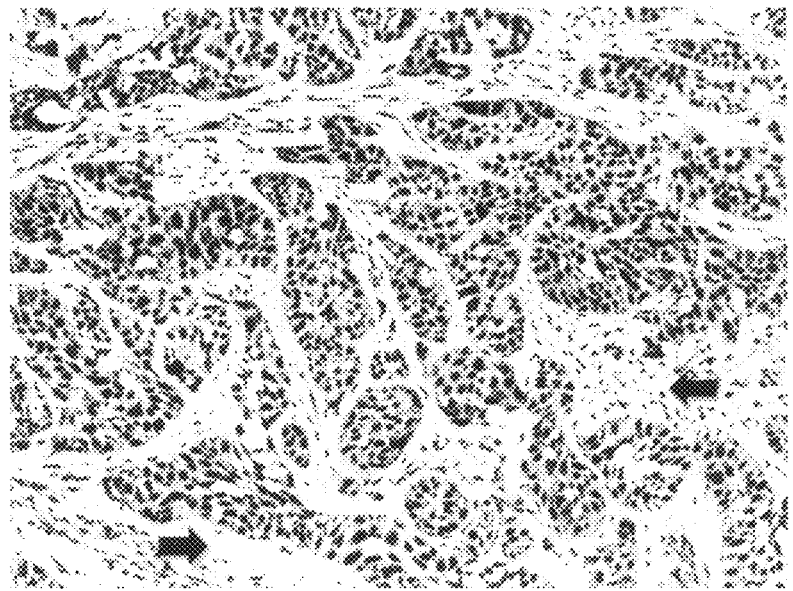
FIG. 4A shows IHC staining of squamous cell carcinoma of nose by an anti-HPV-E6 antibody
Figure 4B:
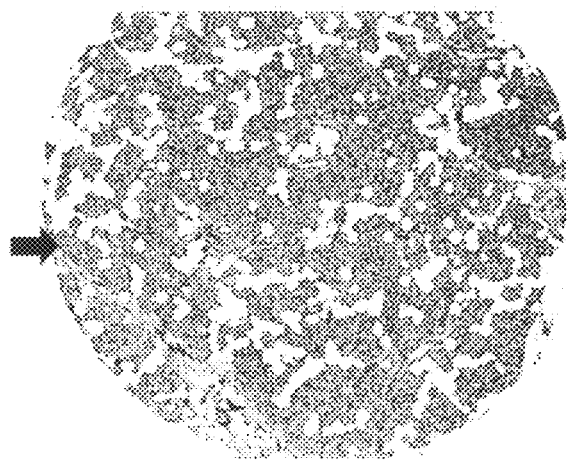
FIG. 4B shows IHC staining of cancer adjacent normal tissue of salivary gland by an anti-HPV-E6 antibody.
Figure 5A:
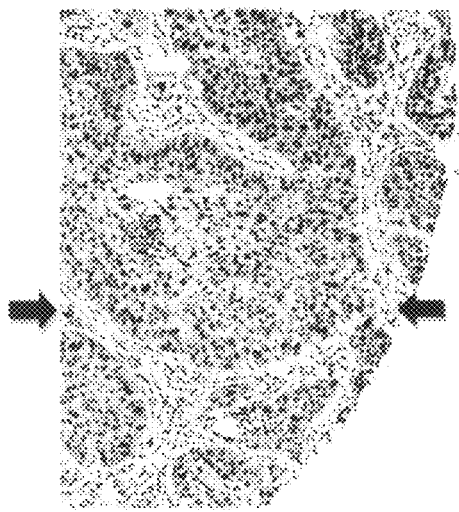
FIG. 5A shows IHC staining of squamous cell carcinoma of larynx by an anti-HPV-E7 antibody.
Figure 5B:
FIG. 5B shows IHC staining of cancer adjacent normal tissue of tongue by an anti-HPV-E7 antibody.

As another example, various organs with various stages of tissues from head and neck cancer were used to show the expression of the E6 or E7 oncoprotein in the tumor cells. FIGS. 4A-4B shows representative images of IHC staining of squamous cell carcinoma of nose tissue (FIG. 4A) and its adjacent normal tissue (FIG. 4B) by staining with a mouse monoclonal Anti-HPV E6 antibody. FIGS. 5A-5B shows representative images of IHC staining of squamous cell carcinoma of nose tissue (FIG. 5A) and its adjacent normal tissue (FIG. 5B) demonstrated by Anti-E7 antibody (mouse monoclonal HPV E7).

The IHC staining results indicate E6 or E7 oncoproteins can be detected in SCC (squamous cell carcinoma) but not in the normal adjacent tissues. Empty blank arrows indicate the specific staining of E6 or E7 protein in tumor cells, while solid black arrows indicate the normal cells with no stain. Highly magnified images indicate localization of the E6 or E7 proteins expressed in the cytoplasm of tumor cells, but not in the adjacent normal cells, nor stroma cells. These data suggest the IHC staining by E6 or E7 monoclonal antibody is specific in the cytoplasm of tumor cells.

Figure 6:
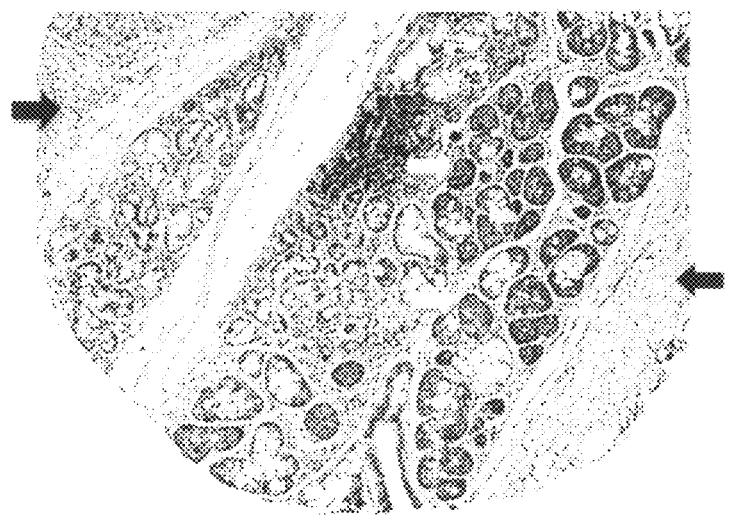
FIG. 6 shows IHC staining of squamous cell carcinoma of the larynx stained by an anti-HPV-L1 antibody.

In addition, the expression of the L1 viral protein in the tumor cells is also detected in various organs/tissues at the various stages of head and neck cancer. FIG. 6 shows representative images of IHC staining of squamous cell carcinoma of larynx tissue demonstrated by a mouse monoclonal Anti-HPV-L1 antibody.

As an example, tonsillar carcinoma is the most prevalent oropharyngeal carcinoma. Cigarette smoking and alcohol are the primary risk factors traditionally associated with the development of this malignancy. The association of human papillomavirus (HPV) infection with tonsillar carcinoma has been suggested by the following observations: HPV DNA has been detected in around 50% of tonsillar carcinomas with HPV-16 as the predominant virus type. HPV-16 DNA is transcribed and present in episomal form in most tonsillar carcinomas and can be detected in carcinoma cells by in situ hybridization. Patients with HPV-16 positive tonsillar tumors seem to have a better survival than HPV negative patients, thus presenting a distinct group among patients with tonsillar carcinoma. Patients with anogenital cancer might have an increased risk for tonsillar carcinoma; HPV DNA has also been detected in lymph node metastases. It should be emphasized that the detection of viral DNA per se does not confirm that the virus has a causal connection with malignant transformation. However, so far, it seems that HPV-16 E6 and E7 are actively transcribed in most tonsillar carcinomas that have been analyzed. Independent of the physical state of the virus, all tonsillar tumors expressed E7 encoding HPV-33 E6*I mRNA, it has been suggested that the transcription of HPV- 16 E6/E7 mRNA in tonsillar carcinomas is not necessarily dependent on viral DNA integration.

To demonstrate a variety of tumors from head and neck cancers tested by HPV IHC, Table 7 contains the results from 19 clinical samples including head and neck squamous cell carcinoma (9) and adjacent normal tissue (10) as negative controls. IHC intensity score for staining of cytoplasm and/or nucleus with an anti-HPV-E7 antibody or an anti-HPV-E6 antibody were shown. Both nucleus and cytoplasmic staining are found the tumor cells of these clinical samples stained with the anti-E7 antibody or anti-E6 antibody. The tissues tested in this microarray and shown positive staining of IHC by anti-E6 or anti-E7 antibody include squamous cell carcinoma (SCC) of left cheek, SCC of cheek, SCC of larynx, and SCC of nose. The results confirm HPV-protein-specific staining of tumor cells from various parts of head and neck cancer. Staining of cytoplasm is found most distinguishable in tumor cells compared to its corresponding normal cells.

TABLE 7

IHC staining results (stain intensity score; 0-3) for biopsy samples from head and neck squamous cell carcinoma (9) and cancer adjacent normal tissue (10) as negative controls using monoclonal Anti-HPV-E6 or Anti-HPV-E7 antibody.

| No. | Organ | pathology | grade | type | α-E7 Ab | α-E6 Ab |
|---|---|---|---|---|---|---|
| 1 | Cheek part | Squamous cell carcinoma (SCC) of left cheek | I | Malignant | 1-2+ | 3+ |
| 2 | Tongue | adjacent normal tissue | — | Adjacent | 0 | 0 |
| 3 | Tongue | adjacent normal tissue | — | Adjacent | 0 | 0 |
| 4 | Cheek part | SCC of cheek | I | Malignant | 1-2+ | 3+ |
| 5 | Cheek part | SCC of cheek | I | Malignant | 1-2+ | NA |
| 6 | Parotid | adjacent normal tissue | — | Adjacent | 0 | 0-1+ |
| 7 | Parotid | adjacent normal tissue | — | Adjacent | 0 | 0-1+ |
| 8 | Larynx | SCC of larynx | II | Malignant | 2+ | 2+ |
| 9 | Larynx | SCC of larynx | III | Malignant | 1+ | 1+ |
| 10 | Larynx | SCC of larynx | III | Malignant | 1+ | 2+ |
| 11 | Tongue | adjacent normal tissue | — | Adjacent | 3+ | 3+ |
| 12 | Tongue | adjacent normal tissue | — | Adjacent | 3+ | 3+ |
| 13 | Nose | SCC of nose | III | Malignant | 2+ | 2+ |
| 14 | Salivary gland | adjacent normal tissue | — | Adjacent | 0 | 0 |
| 15 | Salivary gland | adjacent normal tissue | — | Adjacent | 0 | 0 |
| 16 | Nose | SCC of nose | III | Malignant | 1+ | 2+ |
| 17 | Nose | SCC of nose | III | Malignant | 1+ | 2+ |
| 18 | Tongue | adjacent normal tissue | — | Adjacent | NA | 0 |
| 19 | Tongue | adjacent normal tissue | — | Adjacent | NA | 0 |

To demonstrate a variety of tumors from head and neck cancers can be detected by HPV IHC, additional tissue microarray containing 20 clinical samples including head and neck squamous cell carcinoma (16) and cancer adjacent normal tissue (4) as negative controls are tested using anti-L1 antibody. IHC score for staining of cytoplasm, and/or nucleus followed by the intensity of staining with an Anti-HPV-L1 antibody were shown in Table 8. Both nucleus and cytoplasmic portions of these clinical samples are stained by the anti-L1 antibody. The tumor tissues tested in this microarray and shown positive staining of IHC by anti-L1 antibody include Squamous cell carcinoma (SCC) of upper jaw, SCC of cheek, SCC of larynx, and SCC of left gingiva. The tumor tissues tested in this microarray and shown negative staining of IHC by anti-L1 antibody include little tissue of SCC of larynx, SCC of nasal cavity, Carcinoma sarcomatoids of left ethmoid sinus, and SCC of left gingiva. The results confirm HPV-protein-specific staining of tumor cells as compared to its corresponding normal cells.

TABLE 8

IHC staining results (stain intensity score; 0-3) for biopsy samples from head and neck squamous cell carcinoma (16 samples) and cancer adjacent normal tissue (4 samples, as negative controls) using a monoclonal anti HPV L1 antibody.

| No. | organ | pathology | grade | type | Anti-L1 antibody |
|---|---|---|---|---|---|
| 1 | Upper jaw | SCC of upper jaw | I | Malignant | 1+ |
| 2 | Upper jaw | SCC of upper jaw | I | Malignant | 1+ |
| 3 | Cheek | SCC of cheek | II | Malignant | 2+ |
| 4 | Cheek | SCC of cheek | II | Malignant | 1+ |
| 5 | Larynx | SCC of larynx | I | Malignant | 2+ |
| 6 | Larynx | SCC of larynx | I | Malignant | 1+ |
| 7 | Larynx | SCC of larynx | II | Malignant | 1-2+ |
| 8 | Larynx | SCC of larynx | II | Malignant | 1-2+ |
| 9 | Larynx | Little SCC tissue | — | Malignant | 0 |
| 10 | Nose | SCC of nasal cavity | III | Malignant | 0-1 |
| 11 | Nose | SCC of nasal cavity | III | Malignant | 0-1 |
| 12 | Nose | SCC of nasal cavity | II | Malignant | 0-1 |
| 13 | Nose | SCC of nasal cavity | II | Malignant | 0-1 |
| 14 | Nose | Carcinoma sarcomatoides of left ethmoid sinus | — | Malignant | 0 |
| 15 | Gingiva | SCC of left gingiva | I | Malignant | 0-1 |
| 16 | Gingiva | SCC of left gingiva | I | Malignant | 1+ |
| 17 | Tongue | adjacent normal tissue | — | Adjacent | 0 |
| 18 | Tongue | adjacent normal tissue | — | Adjacent | 0 |
| 19 | Larynx | adjacent normal tissue | — | Adjacent | 0-1 |
| 20 | Larynx | adjacent normal tissue | — | Adjacent | 0-1 |

TABLE 9

Summary of the IHC staining results for an Anti-E7 antibody on head and neck cancer samples.

| | | H&N carcinoma | Normal adjacent | total | | |
|---|---|---|---|---|---|---|
| Anti-E7 antibody | positive | 9 | 2 | 11 | 82% | PPV |
| | negative | 0 | 6 | 6 | 100% | NPV |
| Total | | 9 | 8 | 17 | | |
| Sensitivity | | 100% | | | | |
| Specificity | | | 75% | | | |

To summarize IHC results from table 7, Table 9 shows the results of IHC assay sensitivity for an Anti-E7 antibody at about 100% (9 out of 9) for head and neck cancers with 75% specificity using normal adjacent tissues as negative control; positive predictive value (PPV) at about 82% and negative predictive value (NPV) at about 100%. Two out of the 8 normal adjacent samples show positive staining are tongues tissues adjacent from squamous cell carcinoma of larynx. It requires further investigation to confirm if these two adjacent normal tissues are truly HPV negative To summarize IHC results from table 7, Table 10 shows the results of IHC assay sensitivity for an Anti-E6 antibody at about 100% (8 out of 8) for head and neck cancers with 80% specificity using normal adjacent tissues as negative control; positive predictive value (PPV) at about 80% and negative predictive value (NPV) at about 100%. Two out of the 10 normal adjacent samples show positive staining are tongues tissues adjacent from squamous cell carcinoma of larynx. It requires further investigation to confirm if these two adjacent normal tissues are truly HPV negative.

To summarize IHC results from table 8, Table 11 shows the results of IHC assay sensitivity for an Anti-L1 antibody at about 56% (9 out of 16) for head and neck cancers with 100% specificity using normal adjacent tissues as negative control; positive predictive value (PPV) at about 100% and negative predictive value (NPV) at about 36%. The resulting 100% PPV and 100% specificity values demonstrate HPV-L1 specific IHC staining.

It's noted that the IHC assay sensitivity of about 56% by the Anti-L1 antibody is much lower than assay sensitivity of 100% by the Anti-E7 antibody and Anti-the E6 antibody. These data suggest that detection of E6 or E7 oncoproteins are more relevant to cancer than the detection of the viral capsid protein in head and neck cancer. Previous studies have shown HPV detection of head and neck cancers by DNA test. Together, the results support previous study that HPV-16 E6 and E7 are actively transcribed in most of the tonsillar carcinomas that have been analyzed and all tonsillar tumors expressed E7 encoding HPV-33 E6*I mRNA independent of the physical state of the virus. Therefore, E6 and E7 oncoproteins can better serve as biomarkers for detection of head and neck cancers.

TABLE 10

Summary of the IHC staining results for Anti-E6 antibody on head and neck cancer samples.

| | | H&N carcinoma | Normal adjacent | total | | |
|---|---|---|---|---|---|---|
| Anti-E6 antibody | positive | 8 | 2 | 10 | 80% | PPV |
| | negative | 0 | 8 | 8 | 100% | NPV |
| Total | | 8 | 10 | 18 | | |
| Sensitivity | | 100% | | | | |
| Specificity | | | 80% | | | |

TABLE 11

Summary of the IHC staining results for Anti-L1 antibody on head and neck cancer samples.

| | | H&N carcinoma | Normal adjacent | total | | |
|---|---|---|---|---|---|---|
| Anti-L1 antibody | positive | 9 | 0 | 9 | 100% | PPV |
| | negative | 7 | 4 | 11 | 36% | NPV |
| Total | | 16 | 4 | 20 | | |
| Sensitivity | | 56% | | | | |
| Specificity | | | 100% | | | |

5. Ovarian Cancer

Figure 7A:
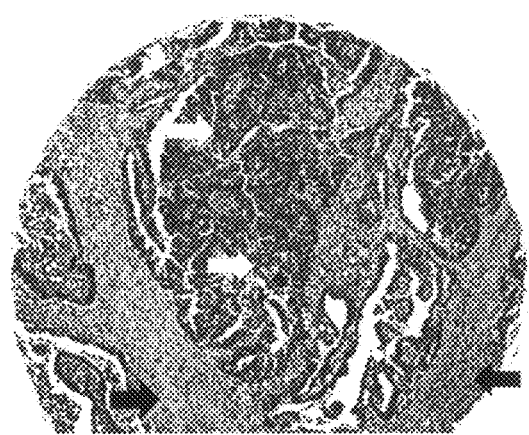
FIG. 7A shows IHC staining of serous papillary cystadenocarcinoma of ovary by anti-HPV-E6 antibody.
Figure 7B:
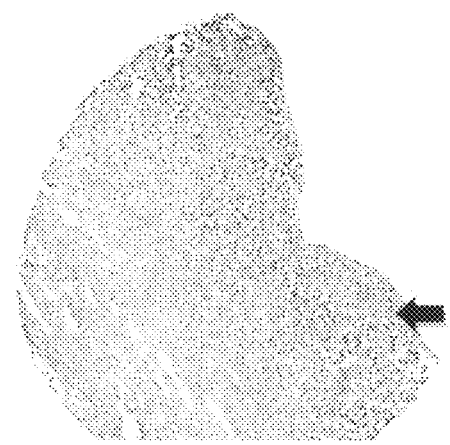
FIG. 7B shows IHC staining of cancer adjacent to ovary tissues of serous papillary cystadenocarcinoma by anti-HPV-E6 antibody.
Figure 8A:
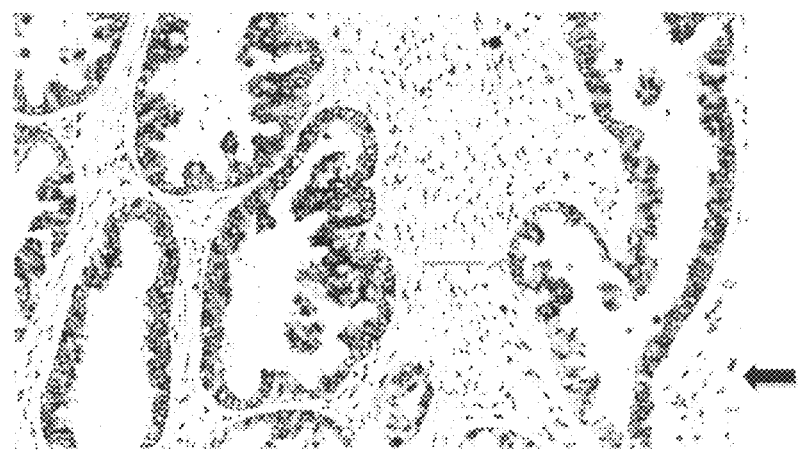
FIG. 8A shows IHC staining of serous papillary cystadenocarcinoma of ovary by anti-HPV-E7 antibody.
Figure 8B:
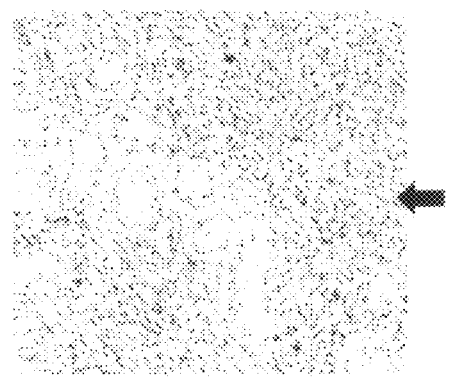
FIG. 8B shows IHC staining of cancer adjacent to ovary tissues of serous papillary cystadenocarcinoma by anti-HPV-E7 antibody.

As another example, various stages of ovary tissues were used to demonstrate the expression of the E6 or E7 oncoprotein in the tumor cells of serous papillary cystadenocarcinoma of ovarian cancers. FIGS. 7A-7B show representative images of IHC staining of serous papillary cystadenocarcinoma of ovary tissue (FIG. 7A) and its adjacent normal tissue (FIG. 7B) demonstrated by the anti-HPV E6 antibody. FIGS. 8A-8B show representative images of IHC staining of serous papillary cystadenocarcinoma of ovary tissue (FIG. 8A) and its adjacent normal tissue (FIG. 8B) by staining with an Anti-E7 mouse monoclonal antibody.

The staining results indicate E6 or E7 oncoproteins can be detected in tumor cells of serous papillary cystadenocarcinoma of ovary but not in the normal adjacent tissues. Empty blank arrows indicate the specific staining of E6 or E7 protein in tumor cells, while solid black arrows indicate the normal cells with no stain. Highly magnified images indicate localization of the E6 or E7 proteins expressed in the cytoplasm of tumor cells, but not in the adjacent normal cells, nor stroma cells. These data suggest the IHC staining by E6 or E7 monoclonal antibody is specific in the cytoplasm of tumor cells.

Figure 9A:
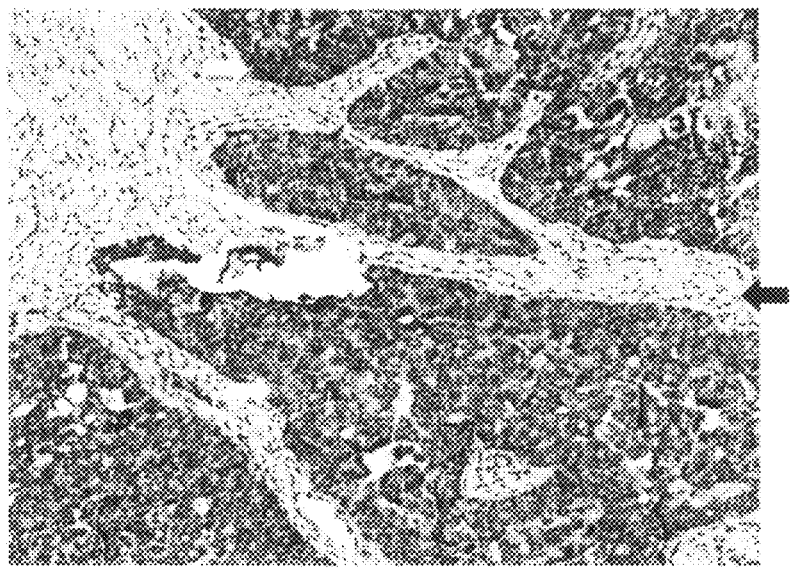
FIG. 9A shows IHC staining of serous papillary cystadenocarcinoma of ovary by an anti-HPV-L1 antibody.
Figure 9B:
FIG. 9B shows IHC staining of another serous papillary cystadenocarcinoma of ovary by anti-HPV-L1 antibody.

The expression of the L1 viral protein is also detected in the tumor cells from the tissue samples at various ovarian cancer stages. FIGS. 9A-9B show representative images of IHC staining of serous papillary cystadenocarcinoma of ovary tissue demonstrated by mouse monoclonal HPV L1 antibody. The IHC staining results indicate expression of L1 viral protein can be detected in tumor cells of serous papillary cystadenocarcinoma of ovary tissue but not in its adjacent normal tissue. Highly magnified images indicate localization of the L1 proteins expressed in the cytoplasm of tumor cells, but not in the adjacent normal cells, nor stroma cells. These data suggest the IHC staining by L1 monoclonal antibody is specific in the cytoplasm of tumor cells.

TABLE 12

IHC staining results (stain intensity score; 0-3) for biopsy samples from ovarian carcinoma (11 samples) and adjacent normal tissue (12 samples, as negative controls) using a mouse monoclonal Anti-HPV-E6 or a mouse Anti-HPV-E7 antibody.

| No. | organ | pathology | grade | type | Anti-E7 antibody | Anti-E6 antibody |
|---|---|---|---|---|---|---|
| 1 | Ovary | Serous papillary cystadenocarcinoma | III | Malignant | 0 | 0 |
| 2 | Ovary | Cancer adjacent ovary tissue of No. 01 | — | Adjacent | 0 | 0 |
| 3 | Ovary | Cancer adjacent ovary tissue of No. 01 | — | Adjacent | 0 | 0 |
| 4 | Ovary | Endometrioid adenocarcinoma | II | Malignant | 1-2+ | 1-2+ |
| 5 | Ovary | Endometrioid adenocarcinoma | II | Malignant | 1-2+ | 1-2 |
| 6 | Ovary | Cancer adjacent ovary tissue of No. 05 | — | Adjacent | 1-2+ | 3+ |
| 7 | Ovary | Cancer adjacent ovary tissue of No. 05 | — | Adjacent | 1-2+ | 1 |
| 8 | Ovary | Serous papillary cystadenocarcinoma | III | Malignant | 0 | 0 |

TABLE 12-continued

IHC staining results (stain intensity score; 0-3) for biopsy samples from ovarian carcinoma (11 samples) and adjacent normal tissue (12 samples, as negative controls) using a mouse monoclonal Anti-HPV-E6 or a mouse Anti-HPV-E7 antibody.

| No. | organ | pathology | grade | type | Anti-E7 antibody | Anti-E6 antibody |
|---|---|---|---|---|---|---|
| 9 | Ovary | A little serous papillary cystadenocarcinoma | III | Malignant | 0-1 | 0 |
| 10 | Ovary | Cancer adjacent ovary tissue | — | Adjacent | 0 | 0 |
| 11 | Ovary | Cancer adjacent ovary tissue | — | Adjacent | 0 | 0 |
| 12 | Ovary | Serous papillary cystadenocarcinoma | II | Malignant | 1+ | 2-3+ |
| 13 | Ovary | Serous papillary cystadenocarcinoma | II | Malignant | 1+ | 2+ |
| 14 | Ovary | Cancer adjacent ovary tissue | — | Adjacent | 0 | 0 |
| 15 | Ovary | Cancer adjacent ovary tissue | — | Adjacent | 0 | 0 |
| 16 | Ovary | Serous papillary cystadenocarcinoma | I | Malignant | 1+ | 1-2+ |
| 17 | Ovary | Serous papillary cystadenocarcinoma | I | Malignant | 1+ | 1-2+ |
| 18 | Ovary | Cancer adjacent ovary tissue | — | Adjacent | 0 | 1 |
| 19 | Ovary | Cancer adjacent ovary tissue | — | Adjacent | 0 | 1 |
| 20 | Ovary | Serous papillary cystadenocarcinoma | I | Malignant | 0 | 1 |
| 21 | Ovary | Serous papillary cystadenocarcinoma | I | Malignant | 0 | 1+ |
| 22 | Ovary | Cancer adjacent ovary tissue | — | Adjacent | 0 | 0 |
| 23 | Ovary | Cancer adjacent ovary tissue | — | Adjacent | 0 | 0 |

TABLE 13

IHC staining results (stain intensity score; 0-3) for biopsy samples from ovarian carcinoma (17 samples) and adjacent normal tissue (4 samples, as negative controls) using a monoclonal Anti-HPV-L1 antibody.

| No. | organ | pathology | grade | type | Anti-L1 antibody |
|---|---|---|---|---|---|
| 1 | Ovary | Endometrioid adenocarcinoma | II | Malignant | 1+ |
| 2 | Ovary | Necrosis tissue | — | Malignant | 0 |
| 3 | Ovary | Serous papillary cystadenocarcinoma | II | Malignant | 1+ |
| 4 | Ovary | Serous papillary cystadenocarcinoma | II | Malignant | 1+ |
| 5 | Ovary | Clear cell carcinoma | — | Malignant | 0 |
| 6 | Ovary | Clear cell carcinoma | — | Malignant | 0 |
| 7 | Ovary | Serous papillary cystadenocarcinoma | II | Malignant | 1+ |
| 8 | Ovary | Serous papillary cystadenocarcinoma | II | Malignant | 0-1+ |
| 9 | Ovary | Serous papillary cystadenocarcinoma | III | Malignant | 1+ |
| 10 | Ovary | Endometrioid adenocarcinoma | I | Malignant | 0 |
| 11 | Ovary | Endometrioid adenocarcinoma | I | Malignant | 0 |
| 12 | Ovary | Serous papillary cystadenocarcinoma | III | Malignant | 1-2+ |
| 13 | Ovary | Serous papillary cystadenocarcinoma | III | Malignant | 0-1 |
| 14 | Ovary | Serous papillary cystadenocarcinoma | II | Malignant | 1+ |
| 15 | Ovary | Serous papillary cystadenocarcinoma | II | Malignant | 1+ |
| 16 | Ovary | Serous papillary cystadenocarcinoma | III | Malignant | 0-1+ |
| 17 | Ovary | Serous papillary cystadenocarcinoma | III | Malignant | 0-1+ |
| 18 | Ovary | Cancer adjacent ovary tissue | — | Adjacent | 0 |
| 19 | Ovary | Cancer adjacent ovary tissue | — | Adjacent | 0 |
| 20 | Ovary | Cancer adjacent ovary tissue | — | Adjacent | 0 |
| 21 | Ovary | Cancer adjacent ovary tissue | — | Adjacent | 0 |

Limited reports suggest HPV infection is associated with ovarian cancer. As a histopathologic diagnosis, a study found that the majority of the patients had serous papillary tumors (81%). HPV was found to be positive in eight patients (8.5%). All of the positive patients had serous papillary tumors (8/76, 10.5%) and advanced stage disease. Six patients had HPV type 16, and the remaining two patients had HPV type 33. None of the patients had more than one type of HPV. These data suggest HPV may have a role in the carcinogenesis of ovarian cancer. It requires investigating this possible relation both in large case-control studies and in vitro models by using more sensitive techniques.

To demonstrate a variety of tumors from ovarian cancers can be detected by HPV IHC, Table 12 shows the results of IHC cytoplasm and/or nucleus staining scores from 21 clinical samples including ovarian carcinoma (11 tissues, 2 tissues per case) and cancer adjacent normal tissue (12 tissues, 2 tissues per case) as negative controls by staining with an anti-HPV-E7 antibody or an Anti-HPV-E6 antibody. The tumor tissues tested in this microarray and shown positive staining of IHC by anti-E6 or anti-E7 antibody on Serous papillary cystadenocarcinoma (SPC). One endometrioid adenocarcinoma tested positively by anti-E6 antibody also positively stained in its normal adjacent tissues. The same case of tissues shows negatively stained by anti-E7 antibody. This endometrioid adenocarcinoma staining by anti-E6 antibody is not considered truly positive as compared to its normal adjacent. These data indicate that this case might be a false positive of IHC assay. However, most SPC tumor samples displayed cytoplasmic staining by the Anti-E7 antibody and/or the Anti-E6 antibody, confirming HPV-specific staining of tumor cells, most distinguishable as compared to corresponding normal cells.

To demonstrate a variety of tumors from ovarian cancers can be detected by HPV IHC, Table 13 shows the results of IHC cytoplasm and/or nucleus staining scores from 21 clinical samples including ovarian carcinoma (17) and cancer adjacent normal tissue (4) as negative controls by staining with an Anti-HPV-L1 antibody. The tumor tissues tested in this microarray and shown positive staining of IHC by anti-E6 or anti-E7 antibody on Serous papillary cystadenocarcinoma (7) and endometrioid adenocarcinoma (1). The tumor tissues tested in this microarray and shown negative staining of IHC by anti-E6 or anti-E7 antibody include endometrioid adenocarcinoma (2), clear cell carcinoma (2), and necrosis tissue (1). Cytoplasmic staining is found in most dysplasia cells samples, confirming HPV-specific staining of dysplasia cells, distinguishable in tumor cells as compared to corresponding normal cells.

TABLE 14

Summary of the IHC staining results for Anti-E7 antibody on serous papillary cystadenocarcinoma (SPC) cancer samples.

| Anti-E7 antibody | Ovary SPC | Normal adjacent | Endometrioid adenocarcinoma | Normal adjacent |
|---|---|---|---|---|
| Positive | 2 | 0 | 0 | 0 |
| negative | 3 | 5 | 1 | 1 |
| total | 5 | 5 | 1 | 1 |
| Sensitivity | 33% | | | |
| Specificity | | 100% | | |

TABLE 15

Summary of the IHC staining results for Anti-E6 antibody on serous papillary cystadenocarcinoma (SPC) cancer samples.

| Anti-E6 antibody | Ovary SPC | Normal adjacent | Endometrioid adenocarcinoma | Normal adjacent |
|---|---|---|---|---|
| Positive | 3 | 1 | 1 | 1 |
| negative | 2 | 4 | 0 | 0 |
| total | 5 | 5 | 1 | 1 |
| Sensitivity | 67% | | | |
| Specificity | | 80% | | |

To summarize data from table 12 using anti-E7 antibody, Table 14 shows the results of assay sensitivity for HPV IHC using an Anti-E7 antibody at about 33% (2 out of 6 cases) for serous papillary cystadenocarcinoma (SPC) with 100% specificity using normal adjacent tissues as negative control. To summarize data from table 12 using anti-E6 antibody, Table 15 shows the results of assay sensitivity for HPV IHC using an Anti-E6 antibody at about 67% (4 out of 6 cases) for serous papillary cystadenocarcinoma (SPC) and endometrioid adenocarcinoma with 80% specificity using normal adjacent tissues as negative control.

To summarize data from table 13 using anti-L1 antibody, Table 16 shows the results of assay sensitivity for HPV IHC using an Anti-L1 antibody at 64% (7 out of 11) for serous papillary cystadenocarcinoma (SPC) and 17% (1 out of 6) for other carcinoma with 100% specificity using normal adjacent tissues as negative control. The positive predictive value (PPV) is at about 100% and negative predictive value (NPV) is at about 31%.

TABLE 16

Summary of the IHC staining results for Anti-L1 antibody on serous papillary cystadenocarcinoma (SPC) and other ovarian cancer samples.

| Anti-L1 antibody | Ovary SPC | Other carcinoma | Normal adjacent | total | | |
|---|---|---|---|---|---|---|
| Positive | 7 | 1 | 0 | 8 | 100% | PPV |
| negative | 4 | 5 | 4 | 13 | 31% | NPV |
| total | 11 | 6 | 4 | 21 | | |
| Sensitivity | 64% | 17% | | | | |
| Specificity | | | 100% | | | |

It's worth noting that HPV is associated with serous papillary cystadenocarcinoma (SPC) more often than other ovarian cancer as data demonstrated by HPV IHC using anti-E6, anti-E7 and anti-L1 antibody as data shown in Table 13-16. HPV IHC using anti-E6 or anti-E7 detects most of SPC, but not endometrioid adenocarcinoma. Using anti-L1 antibody, there is about 64% (7 out 11) of SPC samples that show HPV positive as compared to only about 17% (1 out of 6) of other non-SPC carcinoma. The 6 non-SPC ovary carcinomas include endometrioid adenocarcinoma (3), clear cell carcinoma (2), and necrosis tissue (1). The only one out of the 6 non-SPC shown positive on HPV L1 is endometrioid adenocarcinoma. To average assay sensitivity of ovary cancer for IHC L1 is about 46% (8 out of 17). However, the assay sensitivity obtained herein is much higher sensitivity than any previous reported connection between HPV and serous papillary cystadenocarcinoma, having about 10% reported HPV DNA positive rate for serous papillary cystadenocarcinoma. This HPV IHC assay provide more robust tool to detect HPV in ovarian cancer, and to access the risk of cancer progression by HPV infection.

6. Immunocytochemistry (ICC)

Cervical scrapes collected by liquid based solution were processed according to the manufacturer's instructions. The cell preparation was divided into two parts, one for conventional papsmear, the other one for immunostaining. A monolayer of cervical cells on a slide was processed by cytospin or thin prep techniques. The cells were then fixed and stained followed by immunostaining protocol. Stained cells are examined under a microscope. The same techniques can be applied to various HPV associated cancers for sample scrapes from different part including, but not limited to, oral, nose, respiratory, etc.

Figure 10A:
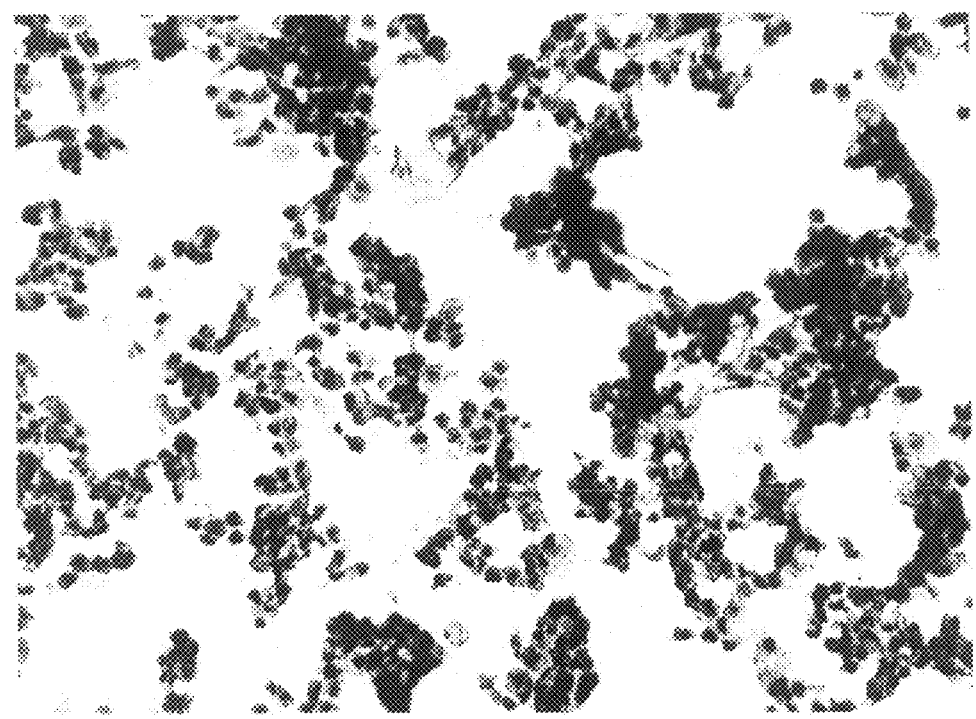
FIG. 10A shows ICC staining of cervical scrape samples (pap smear liquid based) by a mouse monoclonal anti-HPV-E6 antibody.
Figure 10B:
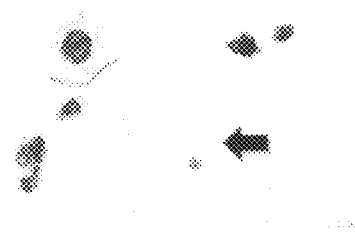
FIG. 10B: ICC staining of cervical scrape samples (liquid based cytology) by a mouse monoclonal anti-HPV-E6 antibody.

FIGS. 10A-10B show ICC staining of cervical scrape cells from liquid based solution. Staining on different types of sample collection like: Digene sample collection, sure path, thin prep; and conventional pap smear sample: demonstrate our ICC staining method using our HPV monoclonal antibody can be applied on all types of samples collected from different solution. FIG. 10A shows ICC staining of cervical scrape samples (pap smear liquid based solution) by a mouse monoclonal Anti-HPV-E6 antibody indicating both nuclear and cytoplasm staining in the SCC cells from cervical cancer sample. FIG. 10B shows IHC staining of cervical scrape samples (pap smear liquid based) by a mouse monoclonal Anti-HPV-E6 antibody indicating nuclear staining in the cells from LSIL sample Samples at different stages of cancer development are confirmed by either Digene DNA test or cytology/pathology for LSIL, ASCUS, HSIL, SCC, etc. Our results show that our antibodies are able to stain all stages of clinical samples in ICC staining. Antibodies for E6, E7, and L1 are tested to demonstrate the ICC staining method works to distinguish positive staining only on abnormal cells, but not normal cells. The same techniques should apply to scrape samples from different parts of tissue, including, but not limited to urothelial, head and neck, colon, etc., to demonstrate detection of HPV proteins in epithelial cell from various cancers/tissues.

7. Cell Staining Followed by Flow Cytometry

As another example of immunoassay for HPV protein detection, flow cytometry assay is used. Cells from cervical scrapes were collected, centrifuged, washed, and immunostained followed by the ICC procedure described above. The HPV E6, E7, or L1 protein can be detected by the specific antibody followed by the $2^{nd}$ antibody labeled with fluorescent dye (FITC, PE, Cy5, etc. conjugated). The cells analyzed by flow cytometry can be gated by size or other parameters to look at the cell population with or without staining. The stain intensity from cell population with smaller cell size can be compared to the cell population with bigger cell size as control of normal cells in the assay. This assay provides specific staining for individual cells. Number of cells stained or unstained can be counted, and the intensity of staining can also be quantitated by analysis of data from flow cytometry. This assay can be high throughput, requires no microscope, nor cytologist to score the staining results. The powerful computer software from the flow cytometry provides non-biased data analysis, and a trained personnel in cytology required. This assay should apply well in the clinical setting as screening test or as a companion test for detection of HPV associated proteins.

To detect HPV proteins followed by flow cytometry, scrape cells from various source of tissues were harvested, washed, cytospinned, monolayered on slides, fixed, and then primary antibody and $2^{nd}$ antibody. The cell suspension was immediately stored at 4° C. in the dark. Analysis: For best results, analyze the cells on the flow cytometer as soon as possible. If longer than an hour before flow analysis, it's necessary to fix the cells. This can preserve them for at least several days. This will stabilize the light scatter and inactivate most biohazardous agents. The fixation for different antigens will require optimization for different assays. Format 1. Paraformaldehyde 0.01% to 1% for 10-15 minutes only, 100 µL per sample. Format 2: Acetone or methanol: Add 1 mL ice cold acetone to each sample. Mix gently. Place at −20° C. for 5 to 10 minutes. Centrifuge, wash twice in PBS 1% BSA.

For intracellular staining, cells can be fixed first to ensure stability of soluble antigens or antigens with short half life. This should retain the target protein in the original cellular location. Detection of intracellular antigens requires a cell permeabilization step prior to staining. Antibodies should be prepared in permeabilization buffer to ensure the cells remain permeable. When gating on cell populations, the light-scatter profiles of the cells on the flow cytometer will change considerably after permeabilization. Antigens in cytoplasmic organelles and granules will require a fixation and permeabilization method depending on the antigen. The epitope needs to remain accessible.

Indirect labeling requires two incubation steps; the first with a primary antibody followed by a compatible secondary antibody. The secondary antibodies are conjugated with a fluorescent dye (FITC, PE, Cy5, etc.). Fixation is critical for the quality of staining assay. There are several methods available for fixation: (1) Formaldehyde followed by detergent: Fixation in 0.01% formaldehyde for 10-15 minutes (this will stabilize proteins), followed by disruption of membrane by detergent. Detergents: Triton or NP-40 (0.1 to 1% in PBS). These will also partially dissolve the nuclear membrane and are therefore very suitable for nuclear antigen staining. It should be noted that loss of cell membrane and cytoplasm will result in decreased light scattering and also in reduced non-specific fluorescence. Tween 20, Saponin, Digitonin and Leucoperm are mild membrane solubilizers. When used at 0.5% in PBS, these give large enough pores for antibodies to go through without dissolving plasma membrane and they are suitable for antigens in the cytoplasm or the cytoplasmic face of the plasma membrane, as well as for soluble nuclear antigens. (2) Formaldehyde (0.01%) followed by methanol. Methanol followed by detergent. Add 1 ml ice cold methanol to each sample. Mix gently. Place at −20° C. for 10 minutes. Centrifuge, wash twice in PBS 1% BSA. Acetone fixation and permeabilization: Add 1 ml ice cold acetone to each sample. Mix gently. Place at −20° C. for 5 to 10 minutes. Centrifuge, wash twice in PBS 1% BSA.

8. Various Immunoassays for Detection of HPV Proteins

As an example, ELISA (Enzyme Linked Immuno Sandwich Assay) or EIA (Enzyme Immuno Assay) can be used as the assay format for HPV protein detection. First, cells, samples or cultured cells to be tested were collected, centrifuged, washed, and lysed to generate cell lysate as anyalyte. The protein in the cell lysate was quantitated and coated to microtiterplate using the same amount of protein for coating of each sample in each well. The plate was blocked, and detected by the HPV monoclonal antibody followed by HRP conjugated anti-mouse IgG. TMB substrate was added, followed by stopping solution. OD 450 was taken by an ELISA plate reader. Cell lysate from cervical cancer cell lines, including cervical cancer cell lines like Caski, Siha, Cxca, Hela, and endometrial cancer cell line like HEC-1A (non-HPV infected) were used to demonstrate the detection of HPV E6, E7, or L1 protein by various Anti-HPV monoclonal antibodies on EIA format. The same assay can be used for cell lysate from different type of malignant cells with various cancers associated with HPV infection.

In one embodiment, the early gene that can be used herein may include papillomavirus E6 genes, papillomavirus E7 genes, among others. In another embodiment, the late gene that can be used herein may include papillomavirus L1 genes, papillomavirus L2 genes, among others.

In high grade CIN lesions, E6 and E7 are strongly expressed in host basal epithelial cells and interfere substantially with cell cycle control of these replication competent host cells. Expression of HPV oncoproteins interferes with G1-S-Phase regulation in host cells. The HPV E6 and E7 proteins target a plethora of cellular interactions, such as the inactivation of pRB by E7 and the degradation of p53 by E6. High level of HPV E7 proteins inactivates pRB and leads to disruption of E2F-Rb binding. Usually, binding of pRB to E2F blocks E2F driven cell cycle activation. In replicating cells, E2F is regulated by phosphorylation of RB. Rb phosphorylation is normally mediated by cyclin dependent kinases (CDK4, CDK6) that are controlled by several kinase inhibitors (INKs).

In addition, host cell proteins important for proliferation and host cell genome replication may be overexpressed as a result of HPV infection. These host cell proteins include, ki67 (MIB-1), MYC cellular oncogene, Cyclin proteins (e.g., cyclin A, B, E, etc.), CDKN2A/p16INK4a, telomerase (e.g., TERC), replication complex proteins (e.g., MCM5, CDC6, topoisomerase II alpha (TOP2A), MCM2, minchromosome maintenance proteins 2, 4, and 5, etc.).

As an example, the immunological assays for detection of HPV proteins, such as E6, E7, L1, etc., or immune response thereof due to HPV infection can be performed in high throughput ELISA screening assays, rapid immunological screening assays, and additional multiplexed protein chip assays, etc., and combinations thereof. Embodiments of the invention provide one or more assays, including antibody, antigen, or immunocomplex assays developed to detect HPV viral proteins encoded by early genes (e.g., E6 and E7) and late genes (e.g., L1). In addition, the developed antibody, antigen, or immunocomplex assays for E6, E7, L1, protein or their antibodies thereof in one format, for example, a microplate format, can be adapted into a one-step immunochromatographic assay for the direct measurement of E6, E7, L1 proteins or antibodies induced by HPV infection.

The one or more protein chip assays, immunological assays, nucleic acid assays, as provided herein aims to employ user friendly procedures with simple instrument or no additional instrument to perform in a short period of time. Comparison of the results of the various immunological assays, nucleic acid hybridization assays with cytological and histological data for the human subjects, as well as demographic information, serve to validate the correlation and accuracy in diagnosing HPV infection and/or cervical cancer and other HPV associated cancers.

The one or more diagnostic immunological assays as described therein may also include obtaining polyclonal antibodies, monoclonal antibodies, and/or antiserum specific against the one or more recombinant proteins as obtained and described herein, taking a clinical sample likely to contain HPV associated proteins and/or antigens, reacting it with the obtained polyclonal antibodies, monoclonal antibodies, and/or antiserum specific for the one or more recombinant proteins, and assaying for the presence of any antibody-antigen complexes by suitable detection systems. Suitable detection systems may employ various colorimetric, chemilluminiscent, fluorescent substrates, etc., specific for a secondary antibody used in each immunological assay.

Early diagnosis of HPV infection is important for successful prevention and treatment of cervical cancer. Strategies to prevent cervical cancer requires improved HPV testing/screening to cover a broad range of the worldwide population, in addition to close follow-up to those subjects with past or present HPV infection and/or precancerous lesions. Importantly, it is known that infection in women for 12-15 years with HPV is required before invasive cancer to develop. It is thus important to be able to assay biomarkers for HPV infection as described herein to pre-screen women early, such that it will be possible to treat HPV infection early and prevent cervical cancer development, rather than having to rely on chemotherapy or radiation to treat cancer malignancy. It is also important to detect HPV infection in different cancers, as males infected with HPV can transmit HPV to his partners. A robust test for HPV detection as described in this invention provides promise to develop assays in different formats for detection of HPV in various tissues from different cancers.

The basic techniques for conducting the immunological assays can be found in "Antibodies: A Laboratory Manual", Harlow and Lane, Cold Spring Harbor Laboratory, Cold Spring Harbor, N.Y. 1989; "Molecular Cloning", A Laboratory Manual, eds. Sambrook, Fritsch and Maniatis, Cold Spring Harbor Laboratory Press, 1989, and others books and manuals known in the art.

Example 9

1. Expression, purification, and preparation of HPV Recombinant protein used as immunogens for generating antiserum, and screening for monoclonal antibody from hybridoma cell lines The method described in this Example can be applied to HPV recombinant proteins from any kinds of HPV proteins, HPV proteins of early genes or late genes, including, but not limited to, E2, E6, E7, L1, L2 and can be from various HPV types. One aspect of the invention provides recombinant proteins, such as recombinant hybrid proteins containing a partial sequence or a full length sequence of HPV oncogenic proteins. Examples include full-length E6, E7, and L1 polypeptide sequences, which have been found very difficult to obtain and purify due to undesirable aggregation during protein purification, protein instability, low levels of expression, and low immunogenic responses of purified proteins. For example, many early E6 oncoproteins contain many cysteine amino acids and thus the correct topography of the E6 oncoproteins requires formation of many disulfide bonds properly. In addition, it was known that certain immunological assays using small peptides of early E6 and E7 proteins results in extremely low assay specificity and sensitivity and thus are unsuitable as tools for clinical in vitro diagnostics.

1). Cloning and production of various recombinant proteins encoded by HPV16 E6 and HPV18 E6 gene. Cloning of an exemplary oncogenic E6 early gene from an exemplary HPV type, HPV-16 described herein a 474 base pair (b.p.) DNA fragment containing the 157 amino acid coding region of the HPV-16 E6 gene was obtained by polymerase chain reaction (PCR) amplification. The DNA sequence of the isolated DNA fragment was confirmed by comparing with the sequence from Gene Bank database. All cloning procedures were carried out according to the protocols described in "Molecular Cloning", A Laboratory Manual, eds. Sambrook, Fritsch and Maniatis, Cold Spring Harbor Laboratory Press, 1989. In addition, HPV18E6, fragments were also cloned and sequence confirmed.

2). Cloning and production of various recombinant proteins encoded by HPV16 E7 and HPV18 E7 gene. Cloning of an exemplary oncogenic E7 early gene from an exemplary HPV type, HPV-16, is described herein. A 294 base pair (b.p.) DNA fragment containing the 99 amino acid coding region of the HPV-16 E7 gene was obtained by polymerase chain reaction (PCR) amplification. The DNA sequence of the isolated DNA fragment was confirmed by comparing with the sequence from Gene Bank database. In addition, E7 DNA fragments from different strains of HPV-16 were also cloned from different clinical samples or sources.

The one or more recombinant proteins as described herein were expressed in various suitable systems, such as bacterial expression systems, viral expression systems, yeast expression systems, mammalian expression systems, e.g., in *E coli*, yeast, baculovirus, and/or mammalian cell cultures, generally known in the field. Although the polypeptides have been obtained by other means, embodiments of the instant invention provide one or more recombinant proteins mostly in (or close to) their native forms with a desirable conformation for binding with antibodies from tissues of human subjects with HPV infection in an immunological assay.

For example, GST, MBP, or His tagged-HPV16-E6, HPV18 E6, HPV16 E7, HPV18 E7, HPV16 L1, and HPV18 L1 recombinant proteins were expressed in *E. coli* BL21 (DE3) using IPTG driven induction. After induction of protein expression, tagged-HPV recombinant proteins were obtained from soluble fraction after lysis of the cultured cells and purified to a final concentration of about 0.1 to 1 mg/ml or higher. The purity of the recombinant HPV proteins was estimated to be >90% based on PAGE analysis. Recombinant HPV proteins were used to detect the presence of HPV antibody on clinical samples and were also used as immunogens for production of polyclonal antiserum and monoclonal antibodies.

The cell culture containing various recombinant papillomavirus proteins in various expression vectors as described herein were then scaled up to 1 liter or 10 liter, or 100 liters or higher to obtain high quantity of soluable recombinant protein for purification. The soluble fraction was passed through various chromatography columns with appropriate system to bind to the tag expressed along with the HPV recombinant proteins. The tag-HPV recombinant proteins were then eluted from the column and concentrated down to 100 ml or 10 ml to 1 ml. The purified soluble recombinant HPV proteins were further concentrated and dialyzed with buffers at neutral pH or PBS buffers to be used as immunogen to generate antiserum against the HPV proteins. The soluble recombinant HPV proteins were thus purified from soluble fractions and folded close to their native folding states as in vivo natural conditions.

Obtaining high quality purified recombinant HPV proteins is critical in generating various types of monoclonal antibodies that recognizing common epitopes or specific epitopes for detecting HPV infection. The purified recombinant HPV proteins were tested to confirm its binding to the HPV antibody from the HPV infected clinical samples. Thus, such purified recombinant HPV proteins are suitable for use as immunogen to raise antiserum producing antibody recognizing the natural HPV proteins in vivo.

3. HPV Monoclonal antibody development: Recombinant HPV E6, E7 or L1 proteins expressed in *E coli* was purified, concentrated, and dialyzed with PBS to be used as immunogen. Immunization of mice was performed by following the standard procedure. Titer of serum was tested by ELISA followed by periodical boosting and bleeding. When the titer reaches optimal, fusion was done using standard procedure.

1). Hybridoma screening: To obtain hybridoma cell line producing HPV monoclonal antibody with specificity described in this invention, fusion clones were screened against not only the immunogen but also related or unrelated proteins as well. Two or more purified HPV recombinant proteins were used to screen against each hybridoma clones to obtain the specificity of each monoclonal antibody described herein.

As an example of hybridoma screening, a monoclonal antibody was obtained by screening antibody-producing hybridoma cells with two or more purified recombinant human papillomavirus proteins such that the monoclonal antibody is capable of reacting with the two or more purified recombinant human papillomavirus proteins. The two or more purified recombinant human papillomavirus proteins described herein consists of HPV 16 E6 protein, HPV 16 E7 protein, HPV 16 L1 protein, HPV 18 E6 protein, HPV18 E7 protein, HPV 18 L1 protein, and combinations thereof.

The two or more purified recombinant human papillomavirus viral proteins are HPV early proteins such that the monoclonal antibody is capable of reacting with the two or more human papillomavirus early proteins. For example, the selected hybridoma cell line produced a monoclonal antibody recognizing a common epitope on both HPV16 E6 and HPV16 E7 proteins. As another example, the selected hybridoma cell line produced a monoclonal antibody recognizing a common epitope on both HPV18 E6 and HPV18 E7 proteins.

As another example, the two or more purified recombinant human papillomavirus proteins comprise a purified recombinant human papillomavirus early protein and a purified recombinant human papillomavirus late protein such that the monoclonal antibody is capable of reacting with a common epitope on the purified recombinant human papillomavirus early protein and the purified recombinant human papillomavirus late protein. The purified recombinant human papillomavirus early protein consists of HPV 16 E6 protein, HPV 16 E7 protein, HPV 18 E6 protein, HPV18 E7 protein, and combinations thereof, and the purified recombinant human papillomavirus late protein consists of HPV 16 L1 protein, HPV 18 L1 protein, and combinations thereof.

For example, the selected hybridoma cell lines produced a monoclonal antibody recognizing a common epitope on HPV16 E6, HPV16 E7, and HPV16 L1 proteins or a common epitope on HPV16 E6 and HPV18 E6 proteins or a common epitope on HPV16 E7 and HPV18 E7 proteins or a common epitope on HPV16 E6, HPV16 E7, HPV16 L1, HPV18 E6, and HPV18 E7 proteins as described in the drawings of this invention.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types are selected from the group consisting of HPV 16, and HPV 18. The two or more different HPV types can also be selected from the group consisting of high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56, and combinations thereof. As an example, the first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

As another example of hybridoma screening described in this invention, a monoclonal antibody was obtained by screening antibody-producing hybridoma cells with a first purified recombinant human papillomavirus protein from a first HPV type and a second purified recombinant human papillomavirus protein from a second HPV type such that the monoclonal antibody is capable of reacting with a specific epitope on only one of the first and the second purified recombinant human papillomavirus proteins and not the other purified recombinant human papillomavirus protein. The first and the second purified recombinant human papillomavirus proteins consists of HPV 16 E6 protein, HPV 16 E7 protein, HPV 16 L1 protein, HPV 18 E6 protein, HPV18 E7 protein, HPV 18 L1 protein, and combinations thereof.

2). Hybridoma cell line stocks: positive clones with desired reactivity on ELISA were selected and cloned down to single cell. Each single clone was then grown up by tissue culture. When the cell numbers reach millions of cell per ml, the cells were frozen down and kept at −80 C or in liquid nitrogen as stock for each cell line.

3). Ascites production: each cell line was grown in tissue culture and injected to mice for ascites production. Ascites were collected and processed for Ig purification by protein G column. Purified Ig from each cell line was isotyped and used for HPV immunoassays.

4. The Specificity of anti-HPV Antibodies.

One or more immunological assays can be used to test the specificity of the monoclonal antibodies generated by screening the hybridoma cell lines with two or more HPV recombinant proteins. EIA (Enzyme Immuno Assay) and/or Western blots were used as the assay format to test the specificity of the HPV antibodies described herein. Various purified recombinant HPV proteins, including the original screening proteins used for obtaining the anti-HPV antibodies and other proteins not used for screening, were used to coat on the microtiter plate to test the specificity of the obtained anti-HPV antibodies on EIA. Proteins in cell lysate from cervical cancer cell lines (with or without HPV infection) were also used to test the specificity of the anti-HPV antibodies by western blot. To confirm the binding and reactivity of the HPV antibodies with proteins from HPV infected cell lines, western blot is very useful to demonstrate specific protein bands corresponding to the proteins present in the HPV-infected cell lines. The protein bands from Western blots were compared to recombinant HPV proteins at their expected molecular weight positions on SDS-PAGE gels. Cell lysate from cervical cancer cell lines, including Hela cell line (HPV18 positive), SiHa cell line (HPV16 positive) and C33A cell line (non-HPV infected) were used to demonstrate detection of HPV E6, E7, or L1 by the HPV monoclonal antibody on western blot.

Figure 11A:
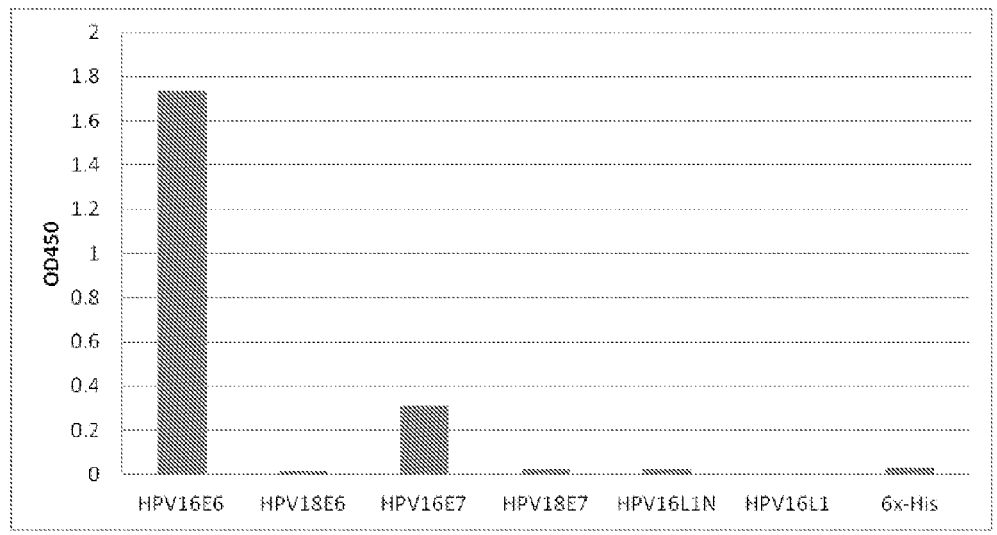
FIG. 11A shows the specificity of a monoclonal antibody capable of reacting with both HPV16 E6 and HPV16 E7 recombinant proteins (different HPV proterins from the same HPV type) and recognizing a common epitope on the different HPV16 E6 and HPV16 E7 proteins from the same HPV 16 type as assayed on EIA (enzyme immuno assays) according to one embodiment of the invention.
Figure 11B:
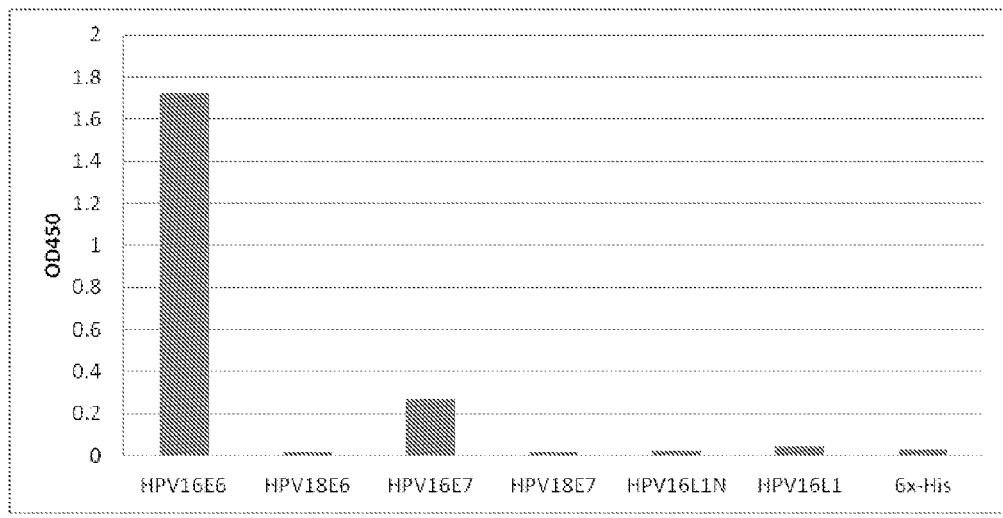
FIG. 11B shows the specificity of another monoclonal antibody capable of reacting with both HPV16 E6 and HPV16 E7 recombinant proteins and recognizing a common epitope on the HPV 16 E6 and HPV16 E7 proteins as assayed on EIA according to one embodiment of the invention.

To demonstrate a monoclonal antibody capable of binding to two or more HPV viral proteins from the same HPV type as described in this invention, FIG. 11A and FIG. 11B show the specificity of a monoclonal antibody, capable of reacting with both recombinant HPV16 E6 and HPV16 E7 proteins on EIA. These data demonstrate the monoclonal antibody described herein reacts specifically to HPV16 E6 and HPV16 E7, but not reactive to HPV16L1, HPV18 E6 or HPV18E7. FIG. 11A and FIG. 11B represent two different clones of hybridoma cells, with each clone being capable of producing a monoclonal antibody recognizing a common epitope on both HPV16 E6 and HPV16 E7 proteins.

Figure 12A:
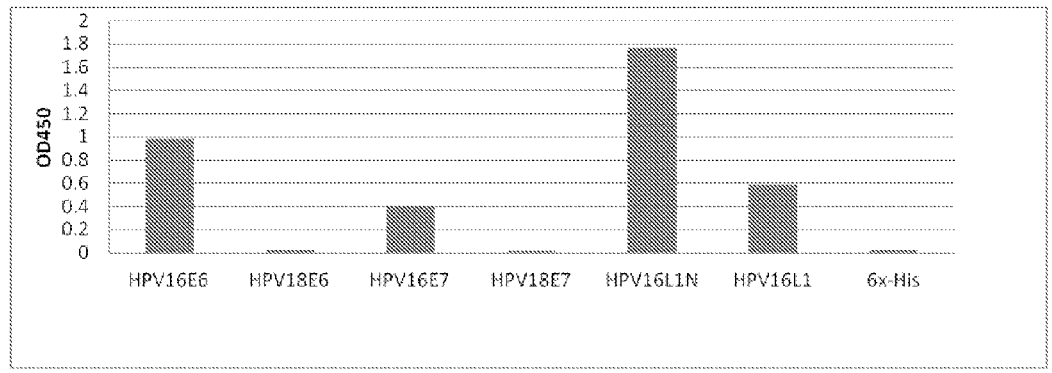
FIG. 12A shows the specificity of a monoclonal antibody capable of reacting with HPV16 E6, E7, L1 & L1 N-terminal recombinant proteins (different HPV proterins from the same HPV type) and recognizing a common epitope on the different E6, E7, L1, and L1 N-terminal proteins from the same HPV 16 type as assayed on EIA according to another embodiment of the invention.

To demonstrate a monoclonal antibody capable of binding to an early HPV viral protein and a late HPV viral proteins from the same HPV type as described in this invention, FIG. 12A shows the specificity of a monoclonal antibody capable of reacting with recombinant HPV E6, HPV E7 and HPV L1 proteins on EIA. The recombinant protein coated on microtiter plate to be detected by the antibody described herein is in native form. These data demonstrate the monoclonal antibody described herein reacts strongly to the native forms of recombinant HPV16 E6 and L1 proteins and weakly to the native form of recombinant HPV16 E7 protein, but is non-reactive to native form of recombinant HPV18 E6 or HPV18 E7. These data indicate that this antibody recognizes an HPV 16 common epitope on the native form of HPV16E6, HPV16E7 and HPV16L1 protein.

Figure 12B:
FIG. 12B shows a western blot of the monoclonal antibody as shown in FIG. 12A, confirming its binding to all of the HPV16 E6, E7 and L1 recombinant proteins.

FIG. 12B shows the results of a Western blot analysis of a monoclonal antibody capable of reacting with recombinant HPV E6, HPV E7 and HPV L1 proteins. The recombinant protein detected by Western blot using the antibody described herein demonstrates the detection of HPV E6 (about 18-20 kDa) and HPV L1 (about 55 kDa) proteins. The bands from each recombinant protein shown with expected molecular weight indicate the monoclonal antibody described herein reacts strongly to denatured HPV16 E6 and HPV18E6 and weakly to denatured HPV L1 proteins on Western blot, and there is no detectable reactivity to HPV16 E7 nor HPV18 E7. Comparing the results as shown in FIG. 12A and FIG. 12B, these data indicate that this anti-HPV monoclonal antibody recognizes an HPV common epitope on the native forms of HPV16 E6, HPV16 E7 and HPV16 L1 protein as well as denatured forms of HPV18 E6 recombinant protein.

Figure 12C:
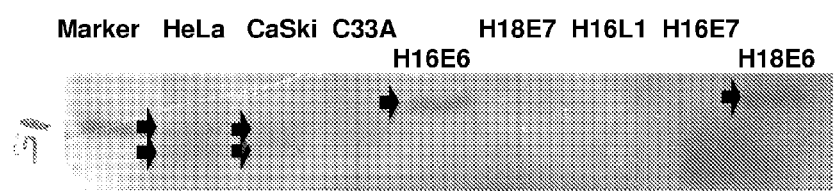
FIG. 12C shows the results of a western blot of cell lysate from cervical cancer cell lines using the monoclonal antibody as shown in FIG. 12A, confirming its binding to all of the HPV16 E6, E7 and L1 viral proteins present in these cervical cancer cell lines.

FIG. 12C shows the results of a Western blot using cell lysate from various cervical cancer cell lines to react with the same monoclonal antibody tested in FIG. 12B binding with recombinant HPV E6, HPV E7 and HPV L1 proteins. Both the cell lysate and recombinant proteins in their denatured forms are tested and shown here (the same monoclonal antibodies as shown in FIG. 12B). The double bands as detected by the monoclonal antibody around the standard molecular weight marker of 17 kDa demonstrate the detection of HPV E6 protein (about 18 kDa) and HPV E7 (about 15 kDa) protein from cervical cancer cell line in HeLa (HPV18) and SiHa (HPV16) cell lines, but not C33A (non-HPV infection) cell line. The bands on the recombinant protein lanes shown with expected molecular weight indicate that the monoclonal antibody reacts strongly to denatured HPV16 E6 and HPV18E6 recombinant proteins, but weakly to denatured HPV L1 recombinant proteins on western blot, and there is no detectable binding to HPV16E7 nor HPV18E7 recombinant proteins.

Figure 13A:
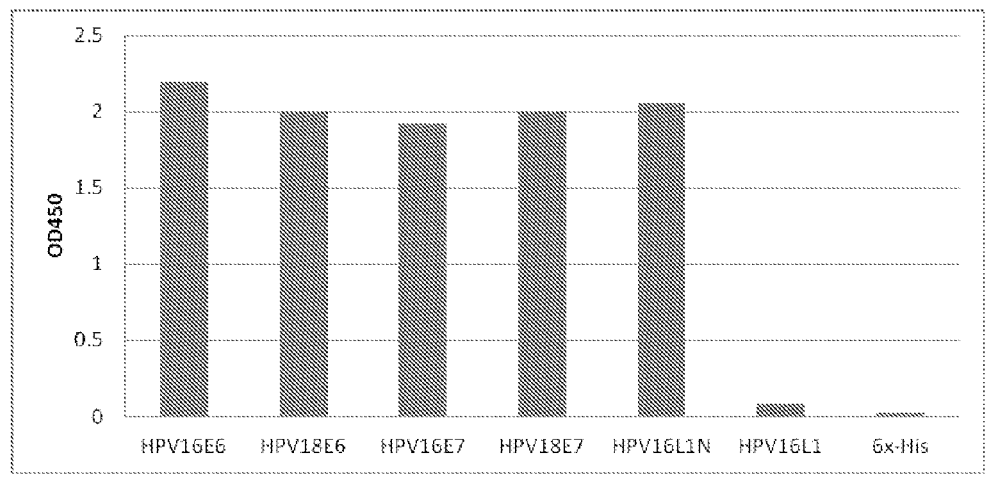
FIG. 13A shows the specificity of a monoclonal antibody capable of binding to all of the recombinant HPV16 E6, E7, and L1 N-terminal proteins as well as HPV18 E6 and E7 proteins (HPV proterins from different HPV types) and recognizing a common epitope on the E6, E7, L1 N-terminal proteins from HPV16 and HPV18 as assayed on EIA according to another embodiment of the invention.

To demonstrate a monoclonal antibody capable of binding to an early HPV viral protein and a late HPV viral protein from different HPV types as described in this invention, FIG. 13A shows the specificity of a monoclonal antibody capable of reacting with recombinant E6, E7 and L1 proteins from both HPV16 and HPV 18 on EIA. These data demonstrate this monoclonal antibody reacts specifically to all of the recombinant E6, E7 and L1 proteins of HPV16, and the recombinant E6 and E7 proteins of HPV18, but not to its common his-tag peptide. These data indicate that this antibody recognizes a common epitope shared by HPV16 and HPV18, as evidenced by its ability to bind to all of the recombinant HPV16 E6, HPV16 E7, HPV16 L1, HPV18 E6, and HPV18 E7 proteins.

Figure 13B:
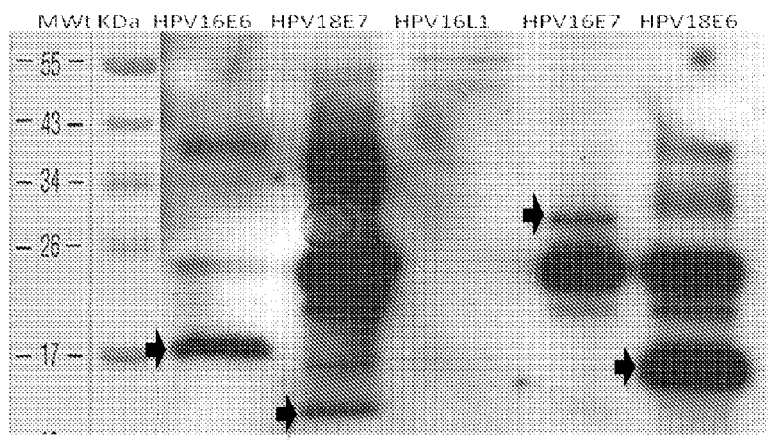
FIG. 13B shows the results of a western blot using the monoclonal antibody as shown in FIG. 13A, confirming its binding to the different recombinant proteins and recognizing a common epitope on the different E6, E7 and L1 proteins from the two different HPV types HPV16 and HPV18.

FIG. 13B shows the results of a Western blot using a monoclonal antibody that recognized a common epitope and is capable of binding to the recombinant E6, E7 and L1 proteins of HPV16 and HPV18. The reactivity of this monoclonal antibody to these recombinant proteins demonstrate that the monoclonal antibody is capable of recognizing E6 (about 18 kDa), E7 (About 15 kDa) and L1 (about 55 kDa) proteins. The resulting bands from each recombinant protein lane of the Western blot analysis showed up at the expected molecular weight position and indicated that this monoclonal antibody reacts strongly to denatured E6 and E7 proteins from both HPV 16 and HPV18, and weakly to denatured L1 proteins on Western blot. The results of FIG. 13A and FIG. 13B indicate that this monoclonal antibody recognizes an HPV common epitope and is capable of binding to the native and denatured form of HPV16 E6, HPV16 E7, HPV16 L1, HPV18 E7 and HPV18 E6 proteins.

Figure 13C:
FIG. 13C shows a western blot cell lysate from cervical cancer cell lines using the monoclonal antibody as shown in FIG. 13A, confirming its binding to the HPV16 E6, E7 and L1 proteins as well as HPV18 E6, E7 and L1 viral proteins present in these cervical cancer cell lines.

FIG. 13C shows the results of a Western blot using cell lysate from various cervical cancer cell lines to react with the same monoclonal antibody tested in FIG. 13B binding with recombinant HPV E6, HPV E7 and HPV L1 proteins. Both the cell lyate and the recombinant proteins in their dentured forms were tested and shown here (the same monoclonal antibodies as shown in FIG. 13B). The double bands as detected by the monoclonal antibody around the standard molecular weight marker of 17 kDa demonstrate the detection of HPV E6 protein (about 18 kDa) and HPV E7 (about 15 kDa) protein from cervical cancer cell line in HeLa (HPV18) and SiHa (HPV16) cell lines, but not C33A (non-HPV infection) cell line. The bands on the recombinant protein lanes shown with expected molecular weight indicate that the monoclonal antibody reacts strongly to denatured HPV16 E6, HPV18 E6, HPV18 E7 recombinant proteins but weakly to denatured HPV L1 recombinant proteins, and there is no detectable binding to HPV16E7 recombinant proteins on the Western blot.

Figure 14A:
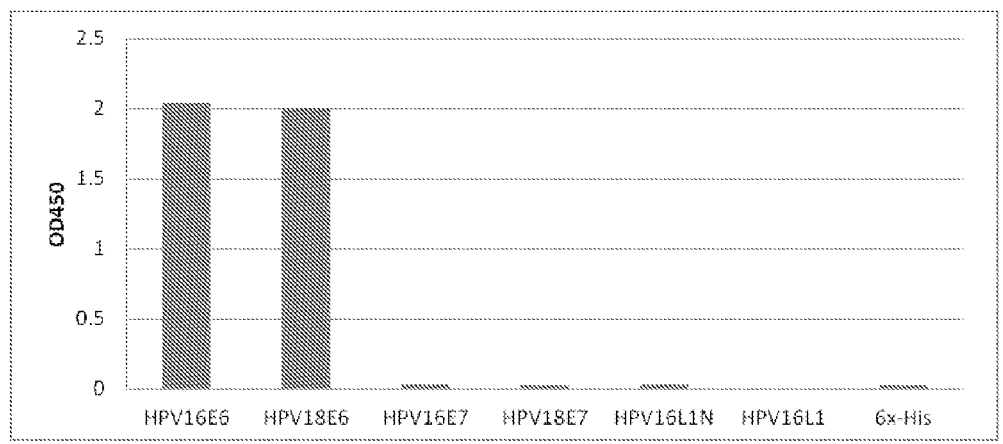
FIG. 14A shows the specificity of a monoclonal antibody capable of binding to two E6 recombinant proteins (HPV16 E6 and HPV18 E6, E6 proteins from different HPV types) and recognizing a common epitope on the two E6 proteins from different HPV types as assayed on EIA according to another embodiment of the invention.

To demonstrate a monoclonal antibody capable of binding to two or more HPV viral proteins from different HPV types as described in this invention, a monoclonal antibody capable of reacting with recombinant E6 proteins of HPV 16 and HPV18 was also the obtained. FIG. 14A shows the specificity of a monoclonal antibody that recognizes the common epitope and is capable of binding to recombinant HPV16 E6 and HPV18E6 proteins on EIA. The recombinant protein coated on microtiter plate to be detected by the antibody described herein is in its native form. These data demonstrate that the monoclonal antibody reacts strongly to the native form of recombinant HPV16 E6 and HPV18E6 proteins, but does not react with the native form of either recombinant HPV E7 or recombinant HPV L1 proteins. These data indicate that this antibody recognizes an HPV E6 common epitope and is capable of binding to the native form of recombinant HPV16 E6, and HPV18 E6 proteins.

Figure 14B:
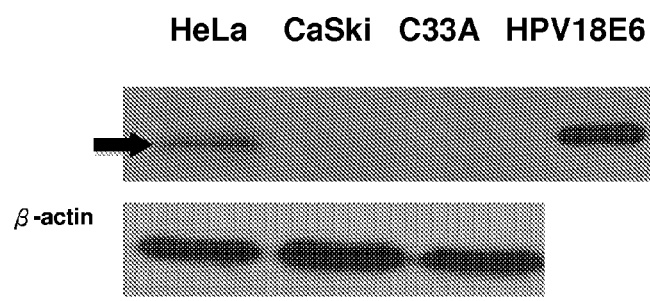
FIG. 14B shows the results of a western blot analyzing the cell lysate from cervical cancer cell lines us ing the monoclonal antibody as shown in FIG. 14A, confirming its binding to HPV16 E6 as well as HPV18 E6 viral proteins present in these cervical cancer cell lines.

FIG. 14B shows the results of a Western blot using cell lysate from various cervical cancer cell lines to react with the same monoclonal antibody tested in FIG. 14A binding with recombinant E6 proteins of HPV 16 and HPV18. Both the cell lyate and the recombinant proteins in their dentured forms were tested and shown here (the same monoclonal antibodies as shown in FIG. 14A). The single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that the monoclonal antibody reacts strongly to denatured HPV18E6 recombinant proteins.

Figure 15:
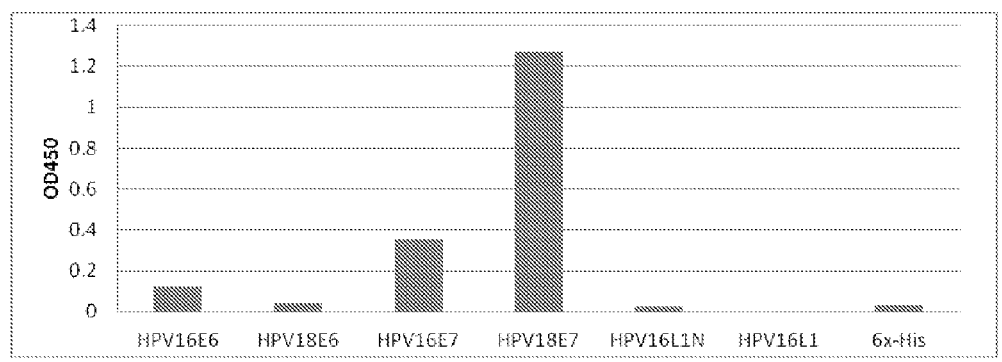
FIG. 15 shows the specificity of a monoclonal antibody capable of reacting with two recombinant HPV16 E7 and HPV18 E7 proteins (E7 proteins from different HPV types) and recognizing a common epitope on the two E7 proteins from different HPV types as assayed on EIA.

As another example to demonstrate a monoclonal antibody capable of binding to two or more HPV viral proteins from different HPV types as described in this invention, FIG. 15 shows the specificity of a monoclonal antibody capable of reacting with both recombinant HPV16 E7 and HPV18E7 protein on EIA. The recombinant protein coated on microtiter plate detected by the antibody described herein is in its native form. These data demonstrate the monoclonal antibody described herein reacts strongly to native form of recombinant HPV16 E7 and HPV18 E7 proteins, but non-reactive to native form of recombinant HPV E6 nor HPV L1 proteins. These data indicate that this antibody recognizes an HPV E7 common epitope and is capable of binding to the native form of HPV16 E7 and HPV18 E7 proteins.

Figure 16:
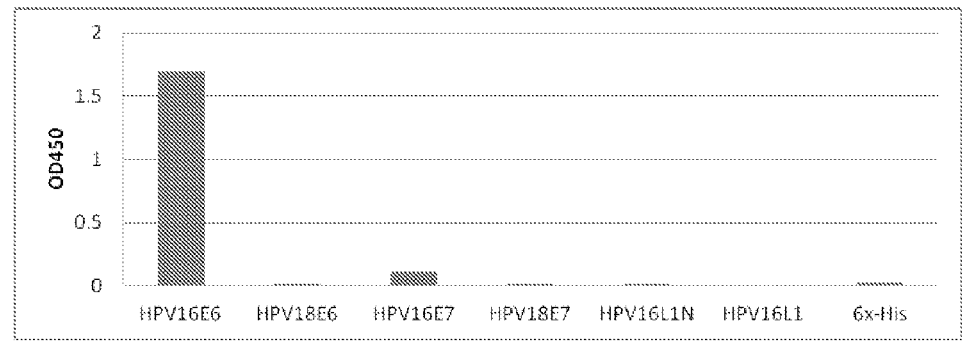
FIG. 16 shows the specificity of a monoclonal antibody capable of reacting with only HPV16 E6 recombinant protein but not with any other HPV recombinant proteins on EIA according to one embodiment of the invention.

To demonstrate a monoclonal antibody capable of binding to only a first HPV viral protein, but not a second HPV viral protein different from the first HPV viral protein, FIG. 16 shows the specificity of a monoclonal antibody capable of reacting with recombinant HPV16 E6 but not with other recombinant HPV proteins on EIA. Data indicate the specificity of this monoclonal antibody that recognizes a specific epitope and is capable of binding to HPV16 E6 only, and not to HPV18 E6 or other recombinant HPV proteins on EIA. The recombinant protein coated on microtiter plate detected by the antibody described herein is in native form. These data demonstrate the monoclonal antibody described herein reacts strongly to the native form of recombinant HPV16 E6 proteins but is non-reactive to the native form of recombinant HPV E7 or L1 proteins. These data also indicate that this antibody recognizes an HPV16 E6-specific epitope and is capable of binding to HPV16 E6 protein only.

As an another example, FIG. 17 shows the specificity of a monoclonal antibody capable of reacting with recombinant HPV18 E6 protein but not with other recombinant HPV proteins on EIA. Data indicate the specificity of this monoclonal antibody that recognizes a specific epitope and is capable of binding to HPV18 E6 only, but not to HPV16 E6 or other recombinant HPV proteins. The recombinant protein coated on microtiter plate detected by the antibody described herein is in native form. These data demonstrate the monoclonal antibody described herein reacts strongly to the native form of recombinant HPV18 E6 proteins but is non-reactive to the native form of recombinant HPV E7 or HPV L1 proteins. These data indicate that this antibody recognizes an HPV18 E6-specific epitope and is capable of binding to HPV18 E6 protein only.

Figure 17A:
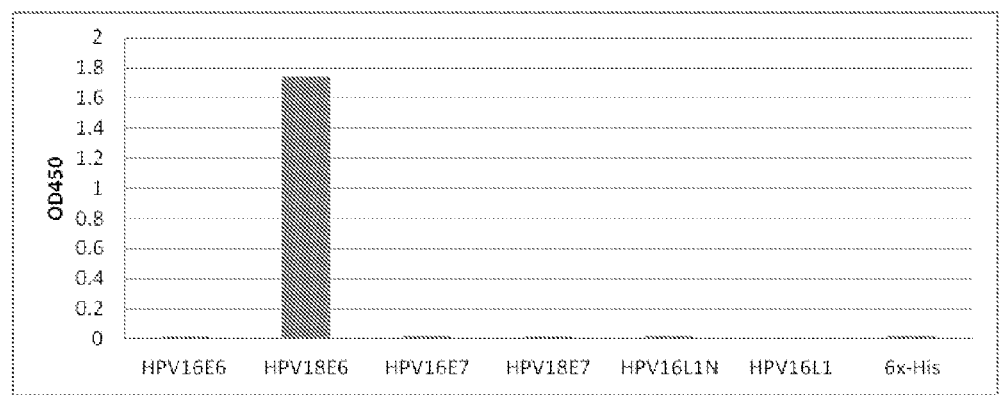
FIG. 17A shows the specificity of a monoclonal antibody capable of reacting specifically with only HPV18 E6 recombinant protein, but not with any other HPV16 or HPV18 recombinant proteins as assayed on EIA according to another embodiment of the invention.
Figure 17B:
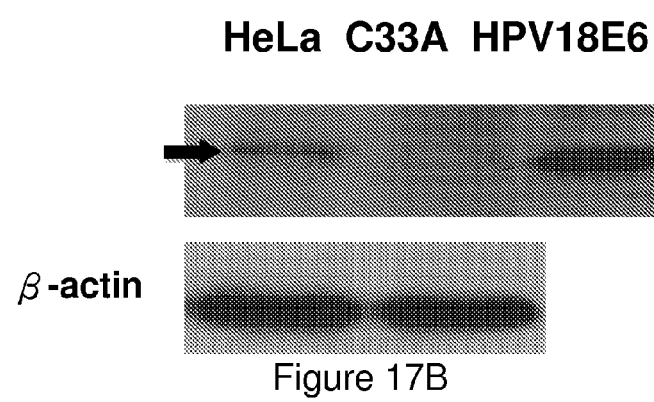
FIG. 17B shows the results of a western blot analyzing the cell lysate from different cervical cancer cell lines using the monoclonal antibody as shown in FIG. 17A, confirming its binding to the-HPV18 E6 viral protein but not HPV E7 viral protein that are present in Hela cell line.

FIG. 17B shows the results of a Western blot using cell lysate from various cervical cancer cell lines to react with the same monoclonal antibody tested in FIG. 17A binding with recombinant HPV 18 E6 proteins. Both the cell lyate and the recombinant proteins in their dentured forms were tested and shown here (the same monoclonal antibodies as shown in FIG. 17A). The single band as detected by the monoclonal antibody around the standard molecular weight marker of 17 kDa demonstrate the detection of HPV E6 protein (about 18 kDa) from cervical cancer cell line in HeLa (HPV18), but not C33A (non-HPV infection) cell line. The bands on the recombinant protein lanes shown with expected molecular weight indicate that this monoclonal antibody reacts strongly to denatured HPV18E6 recombinant proteins only.

Figure 18:
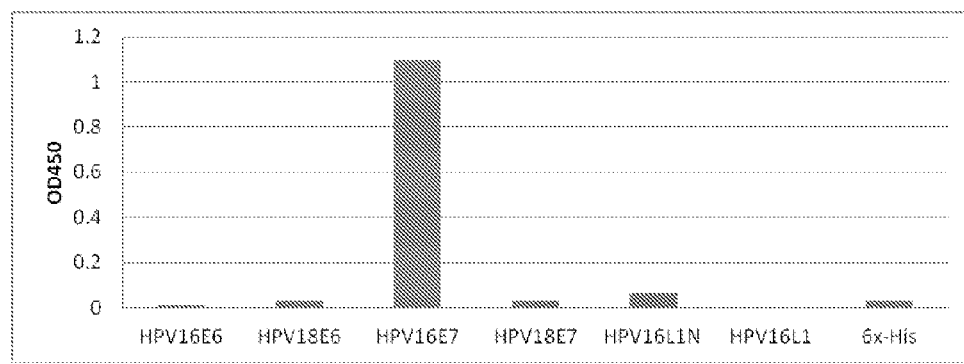
FIG. 18 shows the specificity of a monoclonal antibody capable of reacting specifically with an HPV16 E7 recombinant protein, but not with any other HPV recombinant proteins as assayed on EIA according to another embodiment of the invention.

As another example, FIG. 18 shows the specificity of a monoclonal antibody capable of reacting with recombinant HPV16 E7 but not with other recombinant HPV proteins on EIA. Data indicate the specificity of the monoclonal antibody that recognizes specific epitope and is capable of binding to HPV16 E7 only, but not to HPV18 E7 or other recombinant HPV proteins on EIA. The recombinant protein coated on microtiter plate detected by the antibody described herein is in its native form. These data demonstrate the monoclonal antibody described herein reacts strongly to the native form of recombinant HPV16 E7 proteins, but no detectable binding to the native form of recombinant HPV E6 or L1 proteins. These data indicate that this antibody recognizes an HPV16 E7-specific epitope and is capable of binding to HPV16 E7 protein only.

Figure 19:
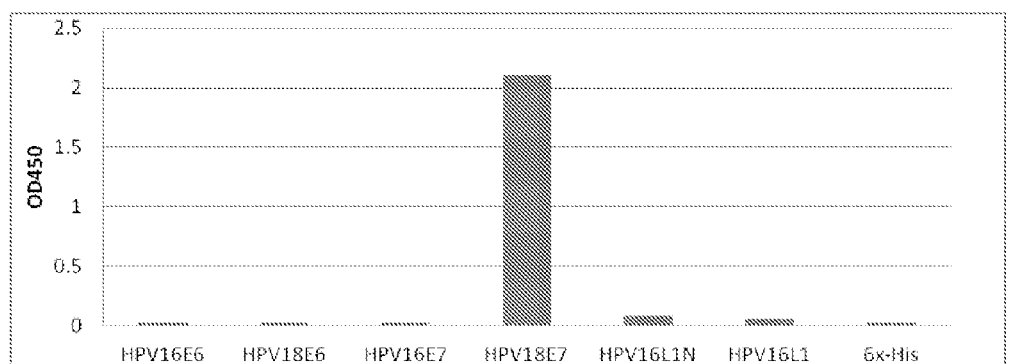
FIG. 19 shows the specificity of a monoclonal antibody capable of reacting specifically with a recombinant HPV18 E7 recombinant protein, but not with any other HPV recombinant proteins as assayed on EIA according to another embodiment of the invention.

As an another example to demonstrate a monoclonal antibody capable of binding to only a first HPV viral protein, but not a second HPV viral protein different from the first HPV viral protein, FIG. 19 shows the specificity of a monoclonal antibody capable of reacting with recombinant HPV18 E7 but not with other recombinant HPV proteins on EIA. Data indicate the specificity of the monoclonal antibody that recognizes a specific epitope and is capable of binding to HPV18 E7 only, and not to HPV16 E7 or other recombinant HPV proteins. The recombinant protein coated on microtiter plate detected by the antibody described herein is in native form. These data demonstrate the monoclonal antibody described herein reacts strongly to the native form of recombinant HPV18 E7 proteins but is non-reactive to native form of recombinant HPV E6 or HPV L1 proteins. These data indicate that this antibody recognizes an HPV18 E7-specific epitope and is capable of binding to HPV18 E7 protein only.

Figure 20A:
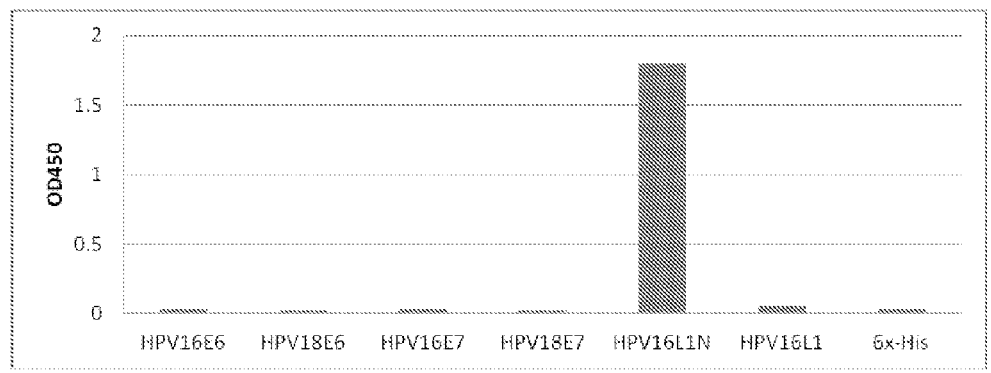
FIG. 20A shows the specificity of a monoclonal antibody capable of reacting specifically with an HPV16 L1 N-terminal recombinant protein, but not with any other HPV recombinant proteins as assayed on EIA according to another embodiment of the invention.
Figure 20B:
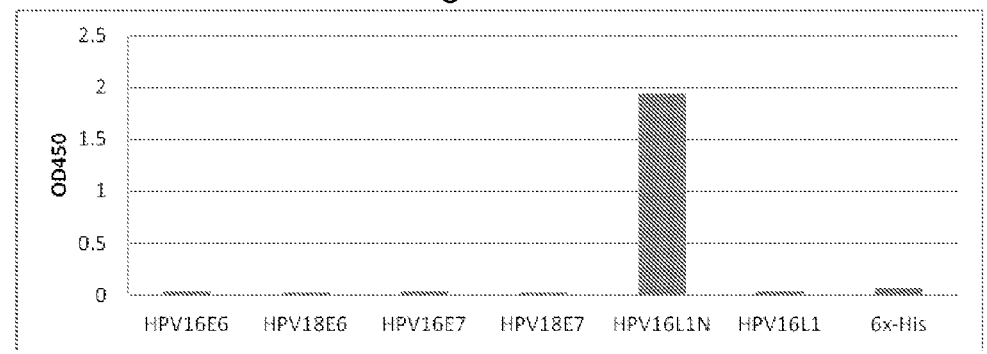
FIG. 20B shows the specificity of another monoclonal antibody capable of reacting specifically with an HPV16 L1 N-terminal recombinant protein, but not with any other HPV recombinant proteins as assayed on EIA.

As an another example to demonstrate a monoclonal antibody capable of binding to only a first HPV viral protein, but not a second HPV viral protein different from the first HPV viral protein, FIG. 20 shows the specificity of a monoclonal antibody capable of reacting with recombinant HPV16 L1-N terminal but not with other recombinant HPV proteins on EIA. Data indicate the specificity of the monoclonal antibody that recognizes a specific epitope and is capable of binding to HPV16 L1 N-terminal only, but does not crossed react with HPV16 L1 or other recombinant HPV proteins on EIA. The recombinant protein coated on microtiter plate detected by the antibody described herein is in its native form. These data demonstrate the monoclonal antibody described herein reacts strongly to the native form of recombinant HPV16 L1-N terminal proteins but is non-reactive to the native form of recombinant HPV E6 or HPV E7 proteins. These data indicate that this antibody recognizes an HPV16 L1 N-terminal specific epitope and is capable of binding to HPV16 L1 N-terminal protein only. FIG. 20A and FIG. 20B represent two different hybridoma clones of cell line producing antibody specific to HPV L1 proteins.

Figure 21:
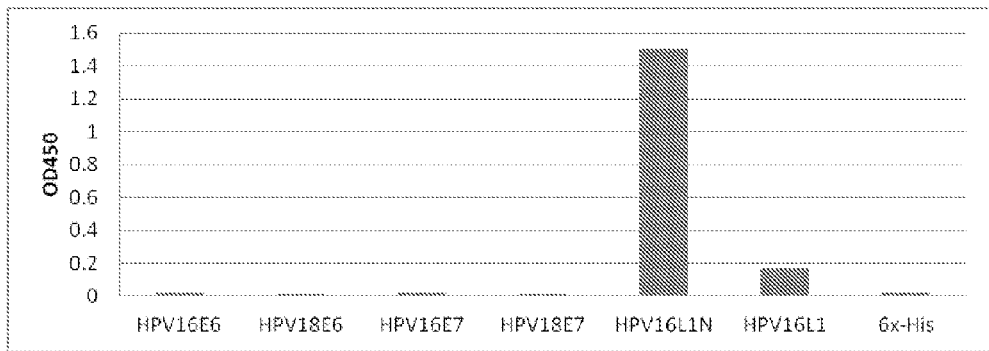
FIG. 21 shows the specificity of a monoclonal antibody capable of reacting specifically with only the HPV16 L1 & L1 N-terminal recombinant proteins, but not with any other HPV recombinant proteins as assayed on EIA according to another embodiment of the invention.

As an another example, FIG. 21 shows the specificity of a monoclonal antibody capable of reacting with recombinant HPV16L1 and HPV16 L1-N terminal but not with other recombinant HPV proteins on EIA. Data indicate the specificity of the monoclonal antibody that recognizes a specific epitope and is capable of binding to HPV16 L1 and HPV16 L1 N-terminal only, and not to other recombinant HPV proteins on EIA. The recombinant protein coated on microtiter plate detected by the antibody described herein is in native form. These data demonstrate the monoclonal antibody described herein reacts strongly to the native form of recombinant HPV 16 L1 and HPV16 L1-N terminal proteins, but is non-reactive to the native form of recombinant HPV E6 or HPV E7 proteins. These data indicate that this antibody recognizes an HPV16 L1 N-terminal-specific epitope and is capable of binding to HPV16 L1 and HPV16 L1 N-terminal protein.

As an example, various cervical tissues from various stages of CIN were prepared to perform IHC assay using rabbit polyclonal anti-HPV E7 antibodies described herein. As another examples, a number of cervical biopsy samples were tested in an immunohistohistochemistry (IHC) assay concurrently as a tissue microarray format using a monoclonal antibody to detect HPV proteins from a variety of HPV types (as confirmed by HPV DNA genotyping). Using a monoclonal antibody against HPV viral proteins and/or oncoproteins, this invention provides antibodies to detect the presence of HPV L1 viral proteins and E6, E7 oncoproteins in clinical samples having either single HPV infection or multiple HPV infections. A single anti-HPV monoclonal antibody as described herein can detect single HPV infection by at least HPV-6, HPV-16, HPV-18, HPV-31, HPV-33, HPV-52, etc, which are cancer-related HPV types (either high risk HPV types or low risk HPV types). A single anti-HPV monoclonal antibody can detect HPV infection by two or more HPV types, such as the combination of HPV-16, HPV-18, HPV-52, HPV-58, HPV-44, HPV-51, HPV-39, HPV-59, etc., which include high risk, low risk, and non-oncogenic α-papillomaviruses.

As an example, the HPV antibodies described in this invention can be applied in clinical utility. The results of the IHC assay demonstrate detection of the HPV E7 protein present in situ from various stages of cervical tissues using a mouse monoclonal anti-HPV E7 antibody. As another example, the antibodies described herein were also used in ICC assay using various cervical tissues from various stages of CIN. As another examples, results of IHC staining using a mouse monoclonal anti-HPV E6 antibody demonstrate detecting the HPV E6 protein present in situ from various stages of CIN tissues. These results indicate that HPV E6 and HPV E7 oncoproteins overexpressed in the dysplasia cells can be specifically detected by the IHC staining using the specific HPV antibodies.

As an example, FIGS. 22A-22D show IHC staining of CIN tissue demonstrated by a mouse monoclonal anti-HPV E6 antibody. Results indicate expression of E6 oncoprotein can be detected early in the precancerous stage of CIN2. Solid Black arrows indicate the specific staining of E6 protein in dysplasia cells, while empty clear arrows indicate the normal cells with no stain. Highly magnified images indicate localization of the E6 proteins expressed early in the nuclear of dysplasia cells.

Figure 22B:
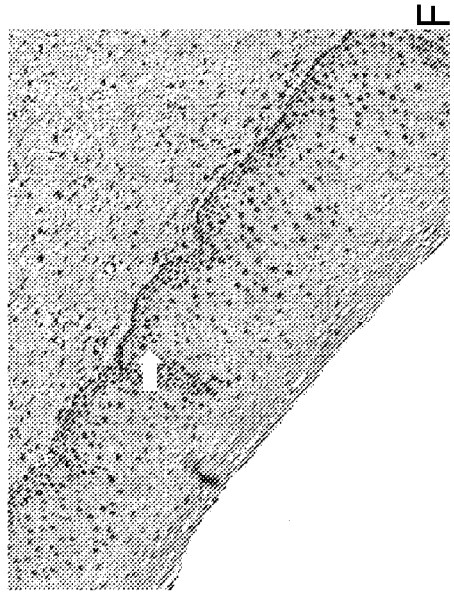
FIG. 22B shows the representative staining image of the normal epithelium adjacent to the dysplasia tissue of the CIN2 sample in FIG. 22A.
Figure 22A:
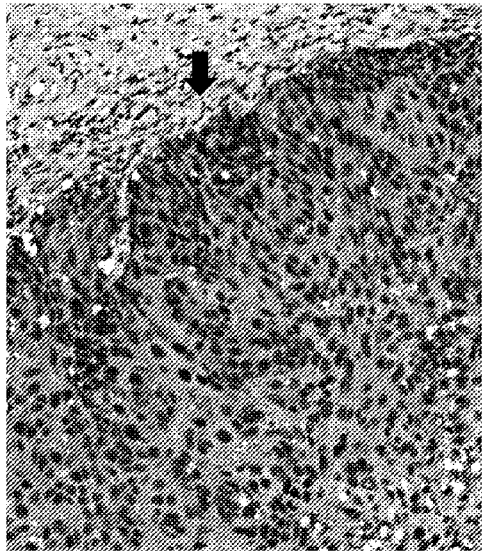
FIG. 22A shows the representative staining image of the dysplasia cells of CIN2 tissues using an anti-E6 monolonal antibody in an immunohistocytostaining (IHC) assay.
Figure 22D:
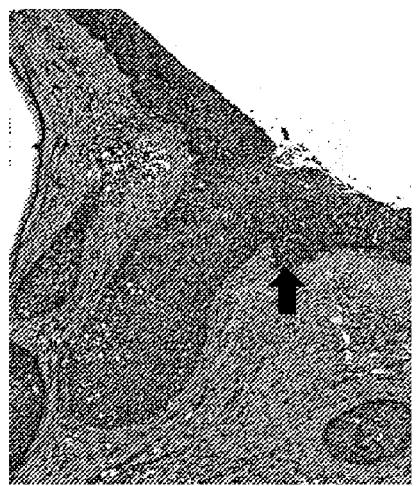
FIG. 22D shows the representative staining image of the dysplasia epithelium of another CIN3 sample stained by the same anti-E6 monolonal antibody as used in FIG. 22A in an IHC assay.
Figure 22C:
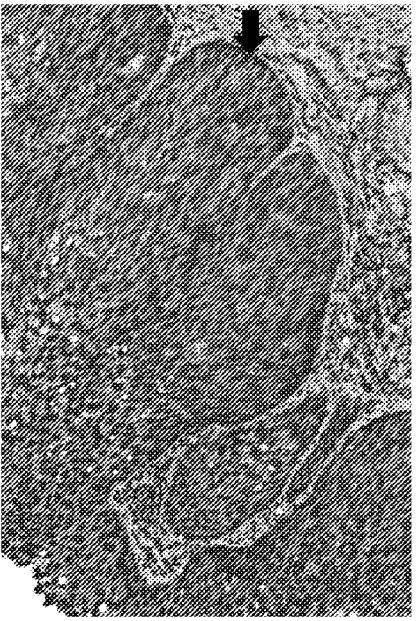
FIG. 22C shows the representative staining image of the dysplasia epithelium of a CIN3 sample stained by the same anti-E6 monolonal antibody as used in FIG. 22A in an IHC assay, demonstrating specific IHC staining in the nuclear and cytoplasm of dysplasia cells by the anti-E6 monoclonal antibody.

FIG. 22A shows the representative image of the dysplasia cells of CIN2 tissues stained by immunohistocytostaining (IHC) using an anti-E6 monolonal antibody. FIG. 22B shows the representative image of the adjacent normal epithelium from the dysplasia tissue of the CIN2 sample of FIG. 22A. FIG. 22C-22D shows the representative image of the dysplasia epithelium of two CIN3 samples stained by IHC using the same anti-E6 monolonal antibody. These data suggest the IHC staining by E6 monoclonal antibody is specific in the nuclear and cytoplasm of dysplasia cells.

Figure 23A:
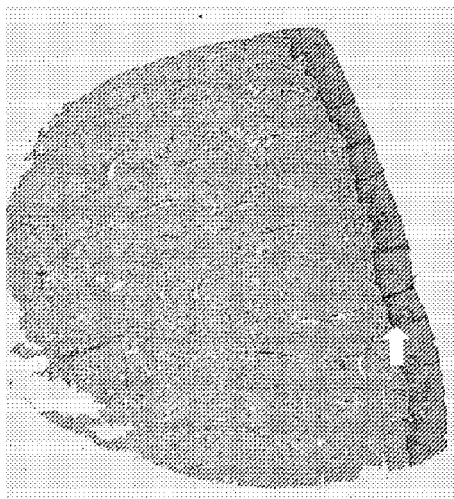
FIG. 23A shows the representative staining image of the squamocarcinoma (SCC) tissue from tissue microarray using an anti-E7 monolonal antibody in an immunohistocytostaining (IHC) assay.
Figure 23B:
FIG. 23B shows the representative staining image of the normal epithelium (about 15 mm away from the tumor tissue) adjacent the SCC tissue of FIG. 23A.
Figure 23C:
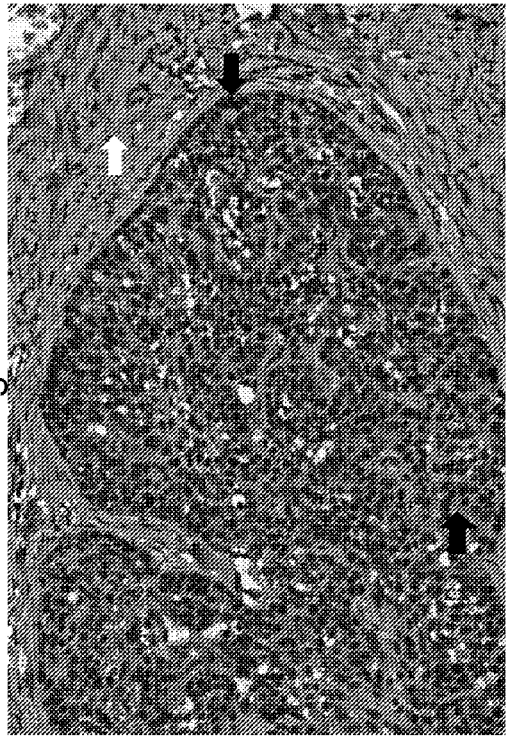
FIG. 23C shows the representative staining image of another SCC sample stained by the same anti-E7 monolonal antibody as used in FIG. 23A in an IHC assay, demonstrating specific IHC staining in the tumor cells by the anti-E7 monoclonal antibody.
Figure 23D:
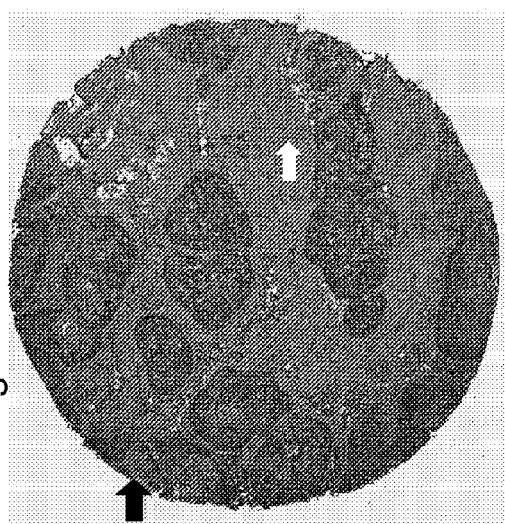
FIG. 23D shows the magnified representative image of the tumor cells from FIG. 23C to view the staining of the cytoplasm of the tumor cells.

As an another example, FIGS. 23A-23D show IHC staining of squamous cell carcinoma demonstrated by mouse monoclonal HPV E7 antibody. Results indicate expression of E7 oncoprotein can be detected in the tumor cells of SCC tissue. Solid Black arrows indicate the specific staining of E7 protein in dysplasia cells, while empty clear arrows indicate the normal cells with no stain. Highly magnified images indicate localization of the E7 proteins expressed in the cytoplasm of tumor cells, but not in the normal epithelium, or stroma cells. These data suggest the IHC staining by E7 monoclonal antibody is specific in the cytoplasm of tumor cells. FIG. 23A shows the representative image of the squamocarcinoma (SCC) tissue from tissue microarray stained by IHC using an anti-E7 monoclonal antibody. FIG. 23B shows the representative image of the normal epithelium (15 mm away from the tumor tissue) of the SCC subject from FIG. 23A. FIG. 23C shows the representative image of another SCC sample from tissue microarray stained by IHC using the same anti-E7 monoclonal antibody. FIG. 23D shows the magnified representative image of the tumor cells stained in cytoplasm from FIG. 23C.

4). The reactivity of the purified anti-HPV Antibodies with HPV Proteins in situ by Immunocytochemistry (ICC):

Cervical scrapes collected by Liquid based solution were processed according to the manufacture instruction. The cell preparation was divided into two parts, one for conventional papsmear, the other one for immunostaining. Monolayer of cervical cells on slide was processed by cytospin or thin prep techniques. The cells were then fixed and stained followed by immunostaining protocol. Stained cells are visualized under microscope.

As an example, FIG. 24A-24C demonstrate immunocytochemistry assay using anti-HPV antibody. FIG. 24A shows the representative image of cervical cells from a CIN2 cervical scrape sample prepared by thin prep and stained by ICC using a mouse monoclonal anti-HPV E7 antibody. FIG. 14B shows the representative image of cervical cells from a CIN3 cervical scrape sample prepared by thin prep and stained by ICC using a mouse monoclonal anti-E6 antibody. FIG. 24C shows the representative image of cervical cells from an adenocarcinoma (ADC) cervical scrape sample prepared by thin prep and stained by ICC using the same anti-E6 antibody shown in FIG. 24B.

TABLE 17

IHC staining results (stained %) and HPV DNA typing for 12 SCC biopsy samples and 12 ADC biopsy samples (C: Cytoplasmic; N: Nucleus; Dys: dysplasia or tumor cells).

| Sample # | HPV type | Anti-E7 Dys (% stained) C | Anti-E7 Dys (% stained) N | Anti-E7 Normal epith. (% stained) C | Anti-E7 Normal epith. (% stained) N | Another anti-E7 Dys (%) C | Anti-E6 Dys (%) C | Another anti-E6 Dys. (%) C | L1 Dys. (%) C |
|---|---|---|---|---|---|---|---|---|---|
| SCC-1 | 18 | 85 | 85 | 0 | 20 | 12.5 | 10 | 70 | 55 |
| SCC-2 | 16, 52 | 90 | 85 | 0 | 25 | 15 | 15 | 10 | 55 |
| SCC-3 | 16 | 60 | 65 | 0 | 40 | 5 | 0 | 10 | 20 |
| SCC-4 | 16 | 92 | 50 | 0 | 40 | 5 | 0 | 10 | 85 |
| SCC-5 | 16, 52, 58 | 92 | 55 | 0 | 50 | 20 | 5 | 15 | 88 |
| SCC-6 | 18, 52, 58 | 90 | 60 | | | 25 | 18 | 10 | 70 |
| SCC-7 | 16, 52 | 92 | 75 | 0 | 30 | 30 | 5 | 10 | 20 |
| SCC-8 | 16, 58 | 10 | 10 | 0 | 5 | 0 | 0 | 10 | 50 |
| SCC-9 | no DNA | 95 | 60 | 0 | 40 | 25 | 8 | 15 | 8 |
| SCC-10 | 18 | 92 | 65 | 0 | 60 | 45 | 25 | 20 | 65 |
| SCC-11 | 16, 58 | | | 0 | 80 | 5 | | 0 | 0 |
| SCC-12 | 33 | 95 | 90 | 0 | 0 | 30 | 1 | 20 | 55 |
| ADE-1 | 16, 18 | 30 | 20 | 0 | 50 | 15 | 25 | 20 | 82 |
| ADE-2 | no DNA | 62 | 40 | 0 | 30 | 35 | 70 | 35 | 78 |
| ADE-3 | 16 | 20 | 30 | 0 | 20 | 35 | 55 | | 60 |
| ADE-4 | 16, 18 | 80 | 80 | 0 | 0 | 10 | 5 | 0 | 90 |
| ADE-5 | 51, 52 | 95 | 80 | 0 | 50 | 10 | 70 | 15 | 92 |
| ADE-6 | 11, 16, 52 | | | 0 | 40 | 5 | 0 | 0 | 15 |
| ADE-7 | 18 | 50 | 40 | 0 | 60 | 25 | 20 | 20 | 75 |
| ADE-8 | 18 | 85 | 60 | 0 | 40 | 15 | 50 | 15 | 82 |
| ADE-9 | 45 | 82 | 55 | 0 | 30 | 30 | 2 | 20 | 40 |
| ADE-10 | 18 | 15 | 10 | 0 | 40 | 15 | 15 | 5 | 70 |
| ADE-11 | 18, 59 | 70 | 0 | 0 | 50 | 15 | 8 | 5 | 65 |
| ADE-12 | 18 | | | | | | | | 30 |

To analyze the HPV IHC results from each subject of invasive cancer, Table 17 shows data from 24 cases of invasive cancer samples with IHC score for staining of cytoplasm (C), and nucleus (N) using C, or N followed by the % of staining using the anti-HPV E7 antibody. Additional anti-HPV antibodies including another anti-E7 antibody, Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies is also shown in Table 17. Results of HPV DNA typing is also shown on the table for its corresponding case.

As shown in Table 17, both nucleus and cytoplasmic staining are found in all the subjects of tumor cells from SCC and ADE stained by the anti-E7 antibody. However, there is more staining (percentage stained) found in the cytoplasm of tumor cells compared to the staining of nuclear of tumor cells. The detection of HPV E7 protein in its adjacent normal epithelium cells was only found in the nucleus, but not found in the cytoplasm of the epithelial cells. The staining of cytoplasm appears most distinguishable in tumor cells compared to its corresponding normal adjacent cells. These data demonstrate expression of HPV E7 proteins was detected in the cytoplasm and nuclear of tumor cells of SCC and ADE tissues. The localization of the E7 proteins expressed in the cytoplasm of tumor cells, but not in the normal epithelium or stroma cells, appears to be tumor specific. HPV E7 proteins present in the nucleus of normal adjacent epithelium and tumor cells detected by the anti-HPV E7 antibody indicate HPV infection with oncoprotein expression. A similar staining pattern was also found when other anti-HPV antibodies were used as shown in Table 17. Data indicate that the HPV IHC assay as described herein can detect HPV early gene such as E6, E7, and late gene such as L1 proteins present in the tumor cells of cervical cancer tissues.

Comparing the results of HPV IHC to the HPV DNA typing, the anti-E7 antibody reacts positively with all the HPV types present in the samples tested. For example, the anti-E7 monoclonal antibody as described herein can detect single HPV infection by at least HPV-16, HPV-18, HPV-33, HPV-45, etc., which are cancer-related HPV types (high risk HPV types). The single anti-E7 monoclonal antibody can also detect HPV infection by two or more HPV types, such as the combination of HPV 11, HPV-16, HPV-18, HPV-52, HPV-58, HPV-51, HPV-59, etc., which include high risk, low risk, and non-oncogenic α-papillomaviruses. However, infection by multiple HPV types contains at least one type that is a high-risk HPV type. These data indicate that the anti-E7 antibody described in this invention is non-type specific, and thus provides a powerful tool to detect HPV E7 proteins from most common high-risk HPV types in the cervical cancer.

The antibody-producing hybridoma cells were also screened with a first purified recombinant human papillomavirus protein from a first HPV type and a second purified recombinant human papillomavirus protein from a second HPV type such that the monoclonal antibody is capable of reacting with a common epitope on human papillomavirus proteins from two or more different HPV types. The first and the second HPV types can be HPV 16, HPV 18, and other HPV types. The two or more different HPV types can be, for example, high risk HPV types, low risk HPV types, HPV-16, HPV-18, HPV-31, HPV-33, HPV-35, HPV-39, HPV-45, HPV-51, HPV-52, HPV-56, HPV-58, HPV-59, and HPV-68, HPV-6, HPV-11, HPV-42, HPV-43, HPV-44, HPV-53, HPV-54, HPV-55, and HPV-56. As an example, the first and the second purified recombinant human papillomavirus proteins may be recombinant HPV 16 E6 protein, recombinant HPV 16 E7 protein, recombinant HPV 16 L1 protein, recombinant HPV 18 E6 protein, recombinant HPV18 E7 protein, and recombinant HPV 18 L1 protein.

As an example of an ICC immunoassay, cells from cervical scrapes were directly smeared on the slides for immunostaining. As another example, cervical cells are collected into a liquid-based solution, centrifuged, washed, followed by immunostained with anti-HPV antibody. Cervical scrapes collected by liquid-based solution were processed according to the manufacture's instruction. The cervical cells were then processed by cytospin or thin prep techniques into a monolayer on a slide.

The thin layer of cells on the slide were then fixed and stained by the various anti-HPV antibodies of the invention. The anti-HPV antibodies may be tagged directly with a detection agent or may be detected by a secondary antibody tagged with a detection agent. Cells stained by the anti-HPV antibody were visualized under microscope.

To demonstrate the HPV ICC assay can be applied to different stages of dysplasia cells, samples from early, intermediate, or late stage of neoplasia are all tested. These samples include, but are not limited to, early stages like LSIL, or CIN1, or ASCUS, or intermediate stages like CIN2, CIN3, or HSIL, or late stages like SCC or ADE or others. To demonstrate the ICC assay described herein can be used to stain for various stages in samples from various sources, different stage of samples in different liquid based solutions were also prepared to perform ICC assay in this invention.

Figure 25A:
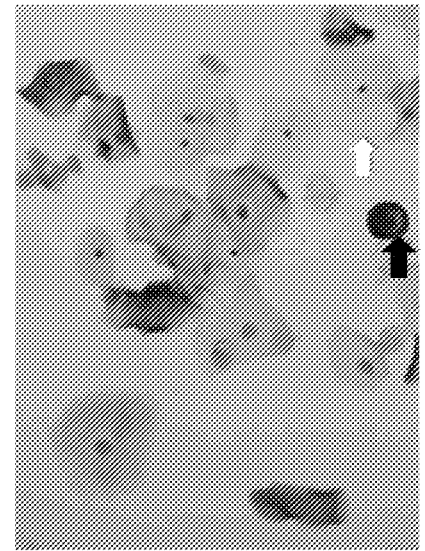
FIG. 25A shows the staining results of a clinical sample, diagnosed as ASCUS, in a liquid based solution using an anti-HPV E6 mouse monoclonal antibody in an ICC assay according to one embodiment of the invention.
Figure 25B:
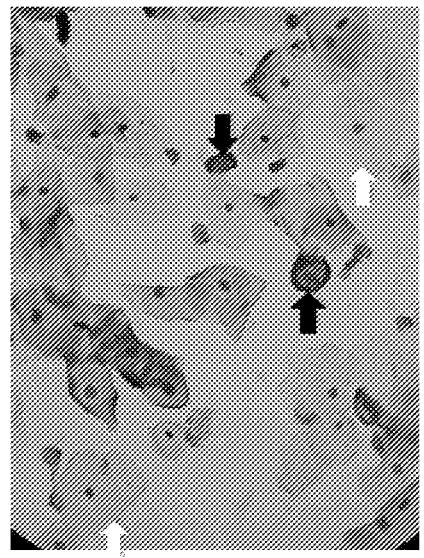
FIG. 25B shows the staining results of the same clinical sample as shown in FIG. 11A using an anti-HPV E7 mouse monoclonal antibody in an ICC assay according to another embodiment of the invention.

To demonstrate HPV ICC assays are useful to identify abnormal cells underdetermined by standard cytological papanicolaou staining, for example, ASCUS (Atypical Squamous Cells of Undetermined Significance, atypical squamous cells of undetermined significance (ASCUS), unusual or atypical cells in pap smear that may be inconsequential or atypical glands of undetermined significance (AGUS), the HPV ICC assays are performed to test for ASCUS and AGUS samples. As shown in FIG. 25A, the results of ICC assay demonstrate that certain cervical scrape cells diagnosed as ASCUS by papanicolaou staining can be ICC stained positively using an anti-E6 monoclonal antibody. FIG. 25B shows the results of ICC assay from the same sample shown in FIG. 15A to demonstrate certain cervical scrape cells (diagnosed as ASCUS by papanicolaou staining) can be ICC stained positively using an anti-E7 monoclonal antibody. As shown in FIG. 25A and FIG. 25B, the abnormal cell with high N/C (nuclear/cytoplasm) ratio (indicated by black arrow) was stained positively while the normal cells (big, irregular cell shape with small nuclear) stain negatively as indicated by the white arrow. Both FIG. 25A and FIG. 25B demonstrate HPV E6 and HPV E7 proteins can be detected in the abnormal cells from samples with pap smear ASCUS. These results indicate that this ASCUS sample containing HPV infected cells with E6 and E7 oncogenic proteins expressed, thus can be detected in situ using the mouse monoclonal anti-HPV E6 and the mouse anti-HPV E7 monoclonal antibody respectively, by the ICC assay described in this invention.

Figure 26B:
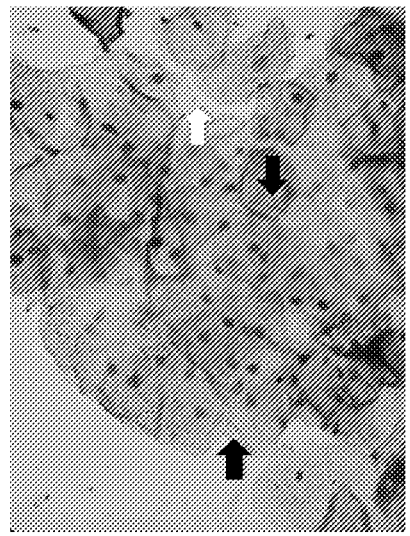
FIG. 26B shows the staining results of another clinical sample, diagnosed as CIN2, in a liquid based solution using an anti-HPV E6 mouse monoclonal antibody in an ICC assay according to another embodiment of the invention.
Figure 26A:
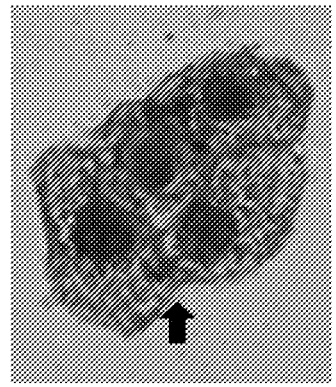
FIG. 26A shows the staining results of a clinical sample, diagnosed as CIN2, in a liquid based solution using an anti-HPV E7 mouse monoclonal antibody in an ICC assay according to one embodiment of the invention.
Figure 27C:
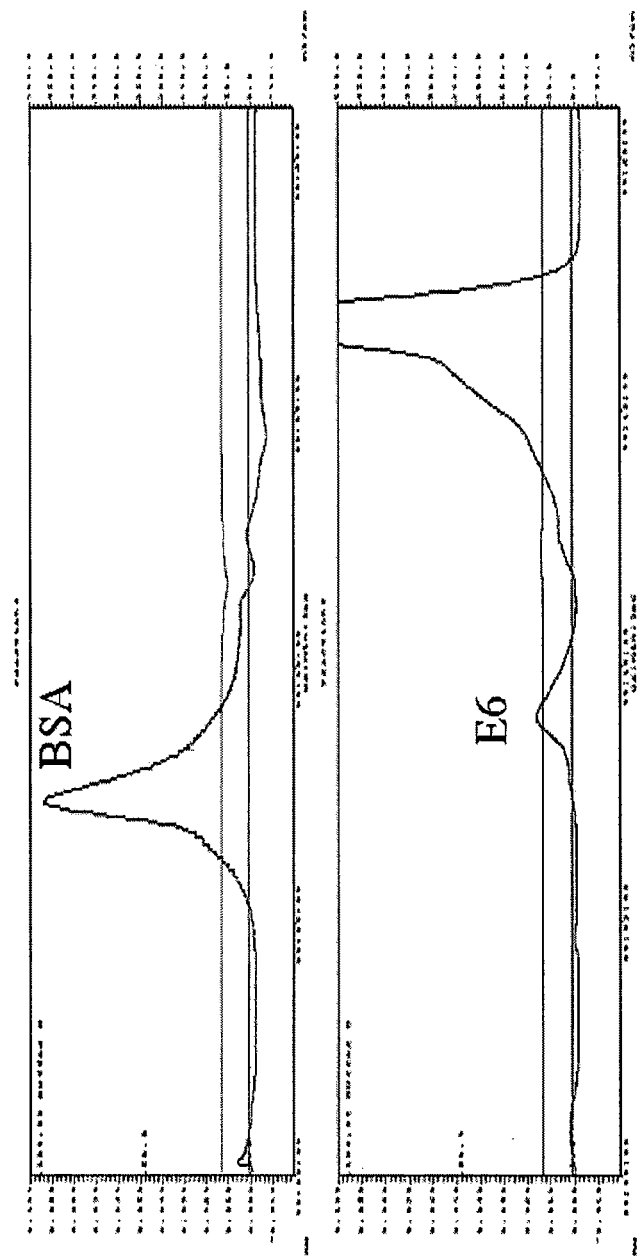
FIG. 27C demonstrates the result of gel filtration column chromatography of the purified recombinant E6 protein, demonstrating that the purified recombinant proteins HPV-16-E6 is a monomeric soluble protein. The purified recombinant E6 protein is eluted later than BSA.
Figure 28:
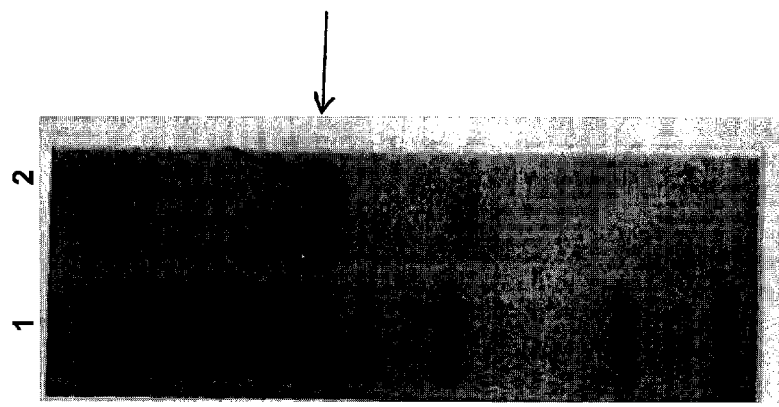
FIG. 28 is a SDS-PAGE gel, showing one exemplary purified recombinant HPV-16-E7 proteins according to one or more embodiments of the invention.
Figure 29:
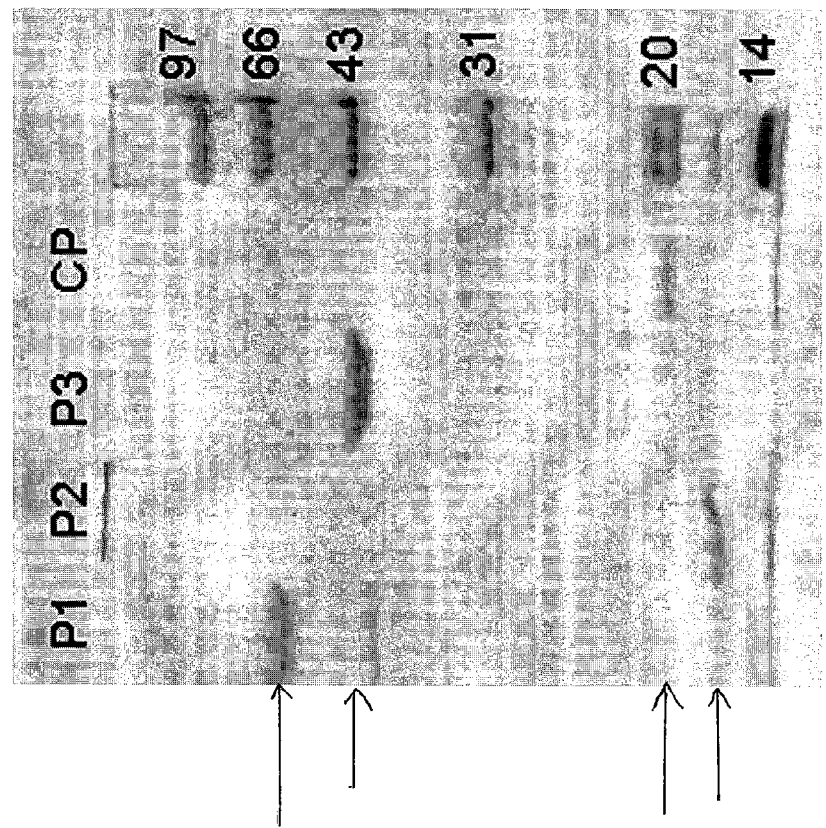
FIG. 29 demonstrates SDS-PAGE of three exemplary purified HPV early gene recombinant proteins by commassie blue staining according to one or more embodiments of the invention. P1: HPV-58-E6-MBP fusion protein; P3: MBP protein; P2: HPV-16-E7-His fusion protein; CP: HPV-16-E6-His fusion protein.

To demonstrate the HPV ICC assay can detect HSIL cells, FIG. 26A shows cervical scrape cells diagnosed as CIN2 by papanicolaou staining. These cells were prepared in another liquid-based solution and are ICC-stained positively using an anti-E7 monoclonal antibody. As shown in FIG. 26A, the CIN2, HSIL abnormal cells are stained positively to the nucleus and cytoplasm. These cells are in the form of connecting each other with high nuclear to cytoplasm (N/C) ratio as indicated by the black arrow. These results demonstrate that HPV E7 protein present in situ can be detected in the abnormal cells from an intermediate stage of neoplasm, in various liquid-based solutions using the mouse monoclonal anti-HPV E7 described herein.

As an another example, FIG. 26B shows another CIN2 sample of cervical scrape cells prepared in another liquid-based solution that are ICC stained positively using an anti-E6 monoclonal antibody. As shown in FIG. 26B, the CIN2, HSIL abnormal cells was ICC-stained positively to the nucleus and cytoplasm. These cells are in the form of connecting each other with high N/C (nuclear/cytoplasm) ratio (indicated as black arrow) These results demonstrate that HPV E6 protein present in situ can be detected in the abnormal cells from an intermediate stage of neoplasm, in various liquid based solution using the mouse monoclonal anti-HPV E6 described herein.

An immunocytochemical (ICC) assay not only detects HPV infection, but also detects HPV oncogenic proteins in situ. Therefore, ICC assay alone, or in combination with various specific and common anti-HPV antibodies can be a powerful tool for HPV detection in situ, as compared to a standard HPV DNA test or pap smear assay.

TABLE 18

ICC staining results using a mouse anti-HPVE6 monoclonal antibody on various cervical scrape samples in a liquid-based solution.

| Pap smear | normal | ASCUS | ASC-H | CIN1 | CIN2/3 | SCC |
|---|---|---|---|---|---|---|
| ICC positive, using an anti-HPV E6 antibody | 4 | 3 | 4 | 11 | 17 | 4 |
| ICC negative, using an anti-HPV E6 antibody | 25 | 6 | 4 | 6 | 0 | 1 |
| total | 29 | 9 | 8 | 17 | 17 | 5 |
| positive rate | 14% | 33% | 38% | 65% | 100% | 80% |

Table 18 shows the results of an ICC assay using a mouse anti-HPVE6 monoclonal antibody on various cervical scrape samples in a liquid-based solution. The results in Table 18 demonstrate that HPV E6 protein can be detected in situ in single cells fixed on a slide by immunocytochemical (ICC) assay using a mouse monoclonal anti-HPV E6 antibody. The in situ presence of HPV E6 proteins can be detected in various stages of cervical scrape samples in various liquid-based solutions. The same cervical scrape samples were also processed by standard papinouli staining to compare the ICC staining results with the pap smear results. As shown in Table 18, HPV E6 proteins are present in the cervical scrape normal, ASCUS, ASC-H, CIN1, CIN2/3 samples with increasing positivity rate, respectively.

TABLE 19

ICC staining results using a mouse monoclonal anti-HPVE7 antibody on various cervical scrape samples in a liquid-based solution.

| Pap smear | normal | ASCUS | ASC-H | CIN1 | CIN2/3 | SCC |
|---|---|---|---|---|---|---|
| ICC positive, using an anti-HPV E7 antibody | 3 | 4 | 3 | 11 | 16 | 4 |
| ICC negative, using an anti-HPV E7 antibody | 25 | 6 | 5 | 6 | 1 | 1 |
| total | 28 | 10 | 8 | 17 | 17 | 5 |
| positive rate | 11% | 40% | 38% | 65% | 94% | 80% |

As another example of the HPV detecting ICC assay, Table 19 show results of ICC staining using anti-HPV E7 antibody. HPV anti-E7 gives comparable ICC results as what is shown for HPV anti-E6. HPV E7 proteins are present in the cervical scrape normal, ASCUS, ASC-H, CIN1, CIN2/3 samples with increasing positivity rate, respectively. There is about 94% positive rate for samples diagnosed with pap smear CIN2/3, while only 11% of samples diagnosed with pap smear normal stained positively by ICC using the same anti-HPVE7 antibody. For ASCUS or ASC-H samples, about 40% of these samples are stained positively by the same anti-HPV E7 antibody as used for the CIN1, CIN2/3 samples shown in Table 3, indicating expression of oncogenic proteins in these ASCUS or ASC-H sample subjects to be followed up for further cancer progression. For samples with pap smear diagnosed as ASCUS and ICC staining (anti-HPV E7) as negative, there may be a lower risk to develop a progressive lesion.

An object of the invention is to develop immune-responsive or antibody-reactive recombinant proteins derived from early genes and/or late genes of various HPV types and strains. It is a further object to provide these recombinant proteins in a chemically pure form. It is a still further object to provide simple, rapid, less expensive and more sensitive assays/tests for diagnosing not only HPV infection, but also most, if not all, HPV-associated neoplasm.

Cloning and production of recombinant proteins encoded by HPV genes: Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6:

GI:9627356; HPV51-E6: GI:9627155; HPV52-E6: GI:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Cloning and production of various recombinant proteins encoded by HPV-16, early E6 gene: Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcaccaaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was subcloned into a histidine tag expression vector, pQE30, in order to express a his-tagged recombinant HPV-16 E6 protein. The resulting plasmid DNA is designated, pQE30/HPV16-E6 for the expression of His-tagged-HPV16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Cloning and production of recombinant proteins encoded by HPV-16 early E7 gene: Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatggagatacacctacattgg 3' (SEQ ID NO. 9) and 5' ccgGAATTCttatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was subcloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

To analyze the HPV IHC results from each subject of CIN3, Table 20 shows data from 30 cases of CIN 3 samples with IHC score for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of tumor cells using other anti-HPV antibodies was also shown in Table 17. Results of HPV DNA typing were also shown on the table for its corresponding case.

As shown in Table 20, nucleus staining is found in the dysplasia cells of all the CIN3 samples tested while only a certain proportion of cases found staining of cytoplasm by the anti-E7 antibody. The results indicate that there is more staining found in the cytoplasm than in the nucleus of dysplasia cells. As shown previously in invasive cancer tissues, HPV E7 protein in its adjacent normal epithelium cells was only found in the nucleus, but not found in the cytoplasm of the epithelial cells. The staining of cytoplasm appears most distinguishable in dysplasia cells compared to its corresponding normal adjacent cells. The localization of the E7 proteins expressed in the cytoplasm of dysplasia cells, but not in the normal epithelium or stroma cells appears HSIL specific. These data demonstrate expression of HPV E7 proteins can be detected in the cytoplasm and nucleus of dysplasia cells of CIN3 tissues. HPV E7 proteins present in the nucleus of normal adjacent epithelium and dysplasia cells detected by the anti-HPV E7 antibody indicate HPV infection with oncoproteins expression. For the cases with high level expression of HPV E7 proteins detected in the cytoplasm of dysplasia cells, it may suggest specific indication of dysplasia progression. A similar staining pattern was also found when other anti-HPV antibodies were used as shown in Table 20. Data indicate that the HPV IHC assay as described herein can detect HPV early genes such as E6, E7, and late genes such as L1 proteins present in the dysplasia cells of CIN3.

Comparing the results of HPV IHC to the HPV DNA typing, the anti-E7 antibody reacts positively with all the HPV types present in the samples tested. For example, the anti-E7 monoclonal antibody as described herein can detect a single HPV infection by at least HPV-16, HPV-18, HPV-31, HPV-33, HPV-39, HPV-58, etc, which are cancer-related HPV types (high risk HPV types). The single anti-E7 monoclonal antibody can also detect HPV infection by two or more HPV types, such as the combination of HPV-16, HPV-18, HPV-33, HPV-39, HPV-52, HPV-58, etc., which include most common high-risk HPV. These data indicate that the anti-E7 antibody described in this invention is non-type specific, and thus provides a powerful tool to detect HPV E7 proteins from most common high-risk HPV types in the CIN3 tissues.

TABLE 20

IHC staining results (stained % and score; 0-3) and HPV DNA typing of 30 CIN 3 samples (M: Membrane; C: Cytoplasmic; N: Nucleus; Dys: Dysplasia).

| | | anti-E7 | | | | | | Anti-E6 Dys. (%) | Another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 31 | 33 | 0 | 80 | 80 | 0 | 0 | 50 | 70 | 40 | 80 |
| 32 | 16 | 0 | 80 | 80 | | | 60 | 0 | 0 | 5 |
| 33 | 16, 58 | | | | 0 | 0 | 60 | | | |
| 34 | 31 | 0 | 50 | 70 | 0 | 0 | 50 | 0 | 0 | 10 |
| 35 | 16, 39 | 0 | 70 | 90 | 0 | 0 | 40 | 0 | 10 | 30 |

TABLE 20-continued

IHC staining results (stained % and score; 0-3) and HPV DNA typing of 30 CIN 3 samples (M: Membrane; C: Cytoplasmic; N: Nucleus; Dys: Dysplasia).

| | | anti-E7 | | | | | | Anti-E6 Dys. (%) | Another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 36 | 31 | 0 | 70 | 60 | 0 | 0 | 50 | 0 | 20 | 20 |
| 37 | 39 | 0 | 0 | 40 | 0 | 0 | 0 | 0 | 0 | 0 |
| 38 | 16 | | | | 0 | 0 | 40 | | | |
| 39 | 16 | 0 | 60 | 70 | 0 | 0 | 40 | 0 | | 0 |
| 40 | 58 | 0 | 90 | 90 | 0 | 0 | 50 | 50 | 0 | 30 |
| 41 | 16 | 0 | 0 | 50 | 0 | 0 | 50 | 0 | 20 | 20 |
| 42 | 16 | 0 | 70 | 70 | 0 | 0 | 30 | 0 | 0 | |
| 43 | 33 | 0 | 0 | 90 | 0 | 0 | 50 | 0 | 0 | 5 |
| 44 | 52 | 0 | 70 | 80 | 0 | 0 | 50 | 70 | 10 | 50 |
| 45 | 51, 52 | 0 | 90 | 90 | 0 | 0 | 30 | 80 | 50 | 10 |
| 46 | 16 | 0 | 0 | 80 | 0 | 0 | 50 | 0 | 0 | 5 |
| 47 | 16 | 0 | 60 | 80 | 0 | 0 | 50 | 30 | 10 | 20 |
| 48 | 16, 58 | 0 | 0 | 80 | 0 | 0 | 50 | 0 | 0 | 10 |
| 49 | 31 | 0 | 80 | 60 | | | 50 | 70 | 40 | 40 |
| 50 | 16 | 0 | 0 | 60 | 0 | 0 | 30 | 0 | 20 | 20 |
| 51 | 6 | | | | 0 | 0 | 20 | | 0 | |
| 52 | 16, 18, 33, 39 | 0 | 0 | 20 | 0 | 0 | 30 | 0 | 0 | 0 |
| 53 | 51, 52, 58 | 0 | 70 | 60 | 0 | 0 | | 60 | 60 | 40 |
| 54 | 16, 45 | 0 | 0 | 70 | 0 | 0 | 50 | 0 | 20 | 20 |
| 55 | 16 | 0 | 0 | 75 | 0 | 0 | 50 | 0 | 0 | 0 |
| 56 | 33, 52 | 0 | 0 | 80 | 0 | 0 | 50 | 0 | 0 | 10 |
| 57 | 16 | 0 | 0 | 50 | 0 | 0 | 40 | 0 | 0 | 0 |
| 58 | 33 | 0 | 0 | 80 | 0 | 0 | | 0 | 20 | 10 |
| 59 | 16 | 0 | 0 | 60 | 0 | 0 | 20 | 0 | 10 | 5 |
| 60 | 16, 52, 58 | 0 | 70 | 80 | 0 | 0 | 50 | 70 | 0 | 20 |

The antibodies as developed herein lend themselves to the high quality and properly purified recombinant proteins encoded by HPV early and late genes, useful in immunological assays to generate very high sensitivity and specificity for screening HPV infection and cervical cancer detection. The monoclonal antibody can be used for one or more immunological assays selected from the group consisting of ELISA (enzyme linked immunoabsorbant assays), antigen assays for papillomavirus proteins, antibody assays for antibodies against papillomavirus proteins, assays for papillomavirus immunocomplexes, protein chip assays, radioimmunoprecipitation assays, rapid membrane immunochromatographic assays, rapid stick immunochromatographic assays, immunohistochemistry for tissues and/or cervical cells, and immunocytological assays followed by flow cytometry, among others. In one embodiment, the one or more immunological assays may be non-invasive with minimal or no additional instrument required.

The clinical utility of the antibodies described herein was validated by Immunoassays like ELISA, Immunohistochemistry, or Immunocytochemistry assay using appropriate clinical samples. The novel monoclonal antibodies and antiserum, obtained from methods of this invention are able to interact and bind HPV viral proteins present in clinical samples, which have been confirmed to contain early stage cell lesions such as cervical intraepithelial neoplasia (CIN) as well as late stage HPV associated cervical cancer. The monoclonal antibodies and antiserum as described herein provide powerful tools to detect and screen HPV related pathogenesis and cervical cancer development in both early stages and late stages; thus provide an avenue to intervene disease progression and a chance to provide early treatment.

The HPV antibodies described in this invention can be used in various immunoassays for detecting general HPV infection as well as infection by various specific HPV genotypes, high risk HPVs and low risk HPVs. The samples to be used in detecting the presence of HPV proteins can be obtained from, but are not limited to, cervical tissues, cervical cells, cervical scrapes, serum, and body fluids. The immunoassays useful for screening or diagnosing cervical cancer or HPV infection include IHC assays, ICC assays, flow cytometry assays, assays using antibodies coupled to beads, rapid tests, protein chip assays, immunoassays with dot blots, immunoassays with slots, as well a conventional ELISA assay. As a screening test, the HPV antibodies can be used to detect HPV proteins in situ present in epithelium cells of cervical scrape from general population in cervical cancer screening as evidenced by ICC staining scored by certified cytologists. As a confirming test, the HPV antibodies can also be used to detect HPV proteins in situ present in epithelium tissue as evidenced by IHC staining scored by certified pathologists.

To analyze the HPV IHC results from each subject of CIN2, Table 21 shows data from 30 cases of CIN 2 samples with IHC scores for staining of cell membrane (M), cytoplasm (C), and nucleus (N) using M, C, or N followed by the % of staining with the anti-E7 antibody. Additional anti-HPV antibodies including Anti-HPV E6 antibody like MAb1 and MAb 7 and anti-HPV L1 antibody were also tested on the same tissue microarray. To demonstrate the IHC staining by various anti-HPV antibodies, IHC score from cytoplasm staining of dysplasia cells using other anti-HPV antibodies is also shown in Table 21. Results of HPV DNA typing are also shown in the table for its corresponding case.

TABLE 21

IHC staining results (stained % and score; 0-3) and HPV DNA typing for 30 biopsy samples (CIN2). (M: membrane; C: cytoplasmic; N: nucleus; Dys: dysplasia)

| | | Anti-E7 | | | | | | Anti-E6 Dys. (%) | another anti-E7 Dys. (%) | Anti-L1 Dys. (%) |
|---|---|---|---|---|---|---|---|---|---|---|
| | | Dysplasia (% stained) | | | Normal epithelium (% stained) | | | | | |
| ID # | HPV type | M | C | N | M | C | N | Cyto | Cyto | Cyto |
| 1 | 6 | 0 | 80 | 80 | 0 | 0 | 30 | 70 | 40 | 80 |
| 2 | 31 | 0 | 0 | 90 | | | | 0 | 40 | 0 |
| 3 | 52 | 0 | 25 | 50 | 0 | 0 | 70 | 0 | 20 | 20 |
| 4 | 16 | 0 | 0 | 40 | 0 | 0 | 30 | 0 | 5 | 0 |
| 5 | 58 | 0 | 0 | 50 | 0 | 0 | 10 | 0 | 0 | 0 |
| 6 | 52 | 0 | 80 | 70 | 0 | 0 | 50 | 0 | 5 | 0 |
| 7 | 53 | 0 | 0 | 80 | 0 | 0 | 30 | 0 | 10 | 10 |
| 8 | 52 | 0 | 50 | 90 | 0 | 0 | 20 | 60 | 10 | 20 |
| 9 | 31 | 0 | 80 | 80 | 0 | 0 | 50 | 70 | 20 | 40 |
| 10 | 16 | 0 | 50 | 80 | 0 | 0 | 50 | 60 | 20 | 10 |
| 11 | no DNA | 0 | 0 | 50 | 0 | 0 | 70 | 0 | 0 | 10 |
| 12 | 33 | 0 | 60 | 60 | 0 | 0 | 50 | 0 | 10 | 30 |
| 13 | no DNA | 0 | 70 | 80 | 0 | 0 | 70 | 0 | 20 | 10 |
| 14 | 52 | 0 | 0 | 70 | 0 | 0 | 70 | 0 | 30 | 20 |
| 15 | no DNA | 0 | 0 | 70 | 0 | 0 | 50 | 0 | 20 | 5 |
| 16 | 52 | 0 | 0 | 10 | 0 | 0 | 30 | 0 | 0 | 5 |
| 17 | 52 | 0 | 0 | 60 | 0 | 0 | 80 | 0 | 0 | 5 |
| 18 | 16 | 0 | 50 | 60 | 0 | 0 | 30 | 50 | 10 | 20 |
| 19 | 16 | 0 | 50 | 70 | | | | 0 | 10 | 20 |
| 20 | 52, 44 | 0 | 50 | 80 | 0 | 0 | 40 | 0 | 30 | 30 |
| 21 | 16 | 0 | 0 | 50 | 0 | 0 | 50 | 0 | 20 | 20 |
| 22 | 16, 18, 6 | 0 | 0 | 40 | 0 | 0 | 0 | 0 | 10 | 0 |
| 23 | 16, 31 | 0 | 0 | 30 | 0 | 0 | 60 | 0 | 0 | |
| 24 | 6 | 0 | 0 | 80 | 0 | 0 | 50 | 0 | 10 | 5 |
| 25 | 16 | 0 | 0 | 10 | 0 | 0 | 60 | 0 | 0 | 0 |
| 26 | 58 | 0 | 0 | 40 | 0 | 0 | 40 | 0 | 10 | 5 |
| 27 | 16, 39, 52 | | | | 0 | 0 | 70 | 0 | | 0 |
| 28 | 6 | 0 | 0 | 50 | 0 | 0 | 70 | 0 | 10 | 5 |

TABLE 21-continued

IHC staining results (stained % and score; 0-3) and HPV DNA typing for 30 biopsy samples (CIN2). (M: membrane; C: cytoplasmic; N: nucleus; Dys: dysplasia)

| ID | | Anti-E7 | | | | | | Anti-E6 Dys. (%) | another anti- E7 Dys. (%) | Anti-L1 Dys. (%) |
| | | Dysplasia (% stained) | | | Normal epithelium (% stained) | | | | | |
| # | HPV type | M | C | N | M | C | N | Cyto | Cyto | Cyto |
|---|---|---|---|---|---|---|---|---|---|---|
| 29 | 16 | 0 | 0 | 70 | 0 | 0 | 5 | 0 | 10 | 20 |
| 30 | 66, 68, | 0 | 0 | 30 | 0 | 0 | 60 | 0 | 10 | 0 |

As shown in Table 21, nucleus staining is found in the dysplasia cells of all the CIN2 samples tested while only a certain proportion of cases found staining of cytoplasm by the anti-E6 or anti-E7 antibody. The results indicate there is more staining of nucleus than cytoplasm of dysplasia cells found in CIN2 samples. As shown previously in SCC, ADC, and CIN3, HPV E7 protein in its adjacent normal epithelium cells was only found in the nucleus, but not found in the cytoplasm of the epithelial cells. The staining of cytoplasm in CIN2 using anti-E6 antibody appears most distinguishable in dysplasia cells compared to its corresponding normal adjacent cells. The localization of the E6 proteins expressed in the cytoplasm of dysplasia cells, but not in the normal epithelium or stroma cells appears HSIL specific. These data demonstrate expression of HPV E6 proteins can be detected in the cytoplasm and nucleus of dysplasia cells of CIN2 tissues. For the cases with high level expression of HPV E6 proteins detected in the cytoplasm of dysplasia cells, it may suggest dysplasia progression. A similar staining pattern was also found when other anti-HPV antibodies were used as shown in Table 21. The HPV IHC assay as described herein can be used to detect HPV early genes such as E6, E7, and late genes such as L1 proteins present in the dysplasia cells of CIN2.

Comparing the results of HPV IHC to the HPV DNA typing, the anti-E7 antibody reacts positively with all the HPV types present in the samples tested. For example, the anti-E7 monoclonal antibody as described herein can detect a single HPV infection by at least, HPV-16, HPV-18, HPV-31, HPV-52, HPV-58, etc, which are cancer-related HPV types (high risk HPV types) and HPV6, HPV 53 which are not high-risk HPV types. The single anti-E7 monoclonal antibody can also detect HPV infection by two or more HPV types, such as the combination of HPV6, HPV-16, HPV-18, HPV-31, HPV-39, HPV-44, HPV-52, HPV-58, HPV-66, HPV-68, etc., which include most common high-risk HPV as well as low risk HPV types. These data indicate that the anti-E7 antibody described in this invention is non-type specific, able to detect HPV E7 proteins from common high-risk HPV types as well as low risk types in the CIN2 tissues. It is possible that formation of dysplasia cells is resulted from expression of oncoproteins, rather than genotyping of HPV types. It shows regression may occur for those infections by high-risk types with no detection of oncoproteins in cytoplasm. Thus, the HPV IHC assay described herein provides additional clinical information, not only for detection of HPV infection, but also for indication of dysplasia progression.

Cloning and production of recombinant proteins encoded by HPV genes. Recombinant proteins encoded by early HPV genes and late HPV genes are obtained. Recombinant proteins can be obtained by itself or as hybrid proteins fused transcriptionally or translational to a portion of a full length DNA fragment for a HPV gene of interest. The DNA sequence of the HPV gene of interest may be derived from high risk HPV types, low risk HPV types, oncogenic HPV strains within a HPV type, etc. An oncogenic HPV strain is an HPV strain that is known to cause cervical cancer as determined by the National Cancer Institute (NCI, 2001). Oncogenic HPV proteins are early viral proteins encoded by an oncogenic HPV type or strain. The sequences of various HPV viral genes and proteins are also found as database entries at NCBI's Gene Bank database, as follows: HPV16-E6: GI:9627100; HPV18-E6: GI:9626069; HPV31-E6: GI:9627109; HPV35-E6: GI:9627127; HPV30-E6: GI:9627320; HPV39-E6: GI:9627165; HPV45-E6: GI:9627356; HPV51-E6: GI:9627155; HPV52-E6: GI:9627370; HPV56-E6: GI:9627383; HPV59-E6: GI:9627962; HPV58-E6: GI:9626489; HPV33-E6: GI:9627118; HPV66-E6: GI:9628582; HPV68b-E6: GI:184383; HPV69-E6: GI:9634605; HPV26-E6: GI:396956; HPV53-E6: GI:9627377; HPV73: GI:1491692; HPV82: GI:9634614, HPV34 GI:396989; HPV67 GI:3228267; and HPV70 GI:1173493.

Example 1

Cloning and Production of Various Recombinant Proteins Encoded by HPV-16, Early E6 Gene Cloning of an exemplary oncogenic E6 early gene from an exemplary HPV type, HPV-16, is described herein. A 474 base pair (b.p.) DNA fragment (SEQ ID NO. 1) containing the 157 amino acid coding region (SEQ ID NO. 2) of the HPV-16 E6 gene was obtained by polymerase chain reaction (PCR) amplification. Primers were used for cloning, for example, a pair of forward and reverse primers, 5' cgcGGATCCcaccaaaagagaactgcaatgtttc 3' (SEQ ID NO. 3) and 5' cccAAGCTTttacagctgggtttctctacgtg 3' (SEQ ID NO. 4), respectively. The DNA sequence of the isolated DNA fragment was confirmed by comparing with the sequence from Gene Bank database. All cloning procedures are carried out according to the protocols described in "Molecular Cloning", A Laboratory Manual, eds. Sambrook, Fritsch and Maniatis, Cold Spring Harbor Laboratory Press, 1989. In addition, E6 DNA fragments from different strains of HPV-16 can also be cloned from different clinical samples or sources.

The obtained 474 base pair (b.p.) DNA fragment was sub-cloned into a histidine tag expression vector, pQE30, in order to express a his-tagged recombinant HPV-16 E6 protein. The resulting plasmid DNA is designated, pQE30/HPV16-E6 for the expression of His-tagged-HPV16-E6 recombinant protein. The DNA sequence and the amino acid sequences of the resulting his-tagged recombinant HPV-16 E6 protein are shown as SEQ ID NO. 5 (a 510 base pair (b.p.) DNA fragment) and SEQ ID NO. 6 (a 169 amino acid fusion protein), respectively.

Other expression vectors which are used as recombinant protein overexpression systems with histidine tag (e.g., $His_6$, $His_8$, etc.), glutathione-S-transferas (GST) fusion, maltose-binding-protein (MBP), among others, can also be used. In addition, the obtained HPV-16 E6 DNA fragment can be sub-cloned into other expression systems, including maltose-binding-protein and glutathione-S-transferase-E6 fusion protein expression systems. Various expression systems can also be used to express E6 recombinant proteins from various HPV types and strains. For example, E6 recombinant protein from HPV-58 was obtained and designated as HPV-16-MBP-E6.

His tagged-HPV16-E6 and MBP-HPV-E6 recombinant proteins were expressed in E. coli BL21(DE3) using IPTG driven induction. After two hour induction of protein expression at 37° C., GST-E6 or MBP-E6 recombinant proteins using standard protocols recommended by the suppliers (Amersham and New England Biolabs, respectively) were obtained and purified to a final concentration of about 1 mg/L. Longer induction time and re-flow though on protein purification column were found to generate higher protein yield, resulting in highly concentrated purified recombinant proteins at a yield of about 2-10 mg/L). The purity of the recombinant GST-E6 proteins was estimated to be >90% based on PAGE analysis. Recombinant E6 fusion proteins was used to detect the presence of E6 antibody on clinical samples and was also be used as immunogens for production of polyclonal antiserum and monoclonal antibodies.

FIGS. 15A and 15B demonstrate the expression of full-length HPV-16 E6 recombinant protein induced by IPTG analyzed by SDS-PAGE and western blot, respectively, using anti-E6 monoclonal antibody (MAb1-1). The molecular weight of the resulting His-tagged-HPV16-E6 recombinant protein is about 20.5 KD. The western blot was performed on a PVDF membrane using an anti-E6 monoclonal antibody, which is a mouse antibody, followed by a secondary antibody, an alkaline peroxidase (AP)-goat-anti-mouse IgG1, and visualized by the reaction of NBT and BCIP substrate mixture. The results showed that a single major protein band and thus pure recombinant E6 protein was purified. The purity of the recombinant E6 proteins was estimated to be about 90% or more based on PAGE analysis.

The purified recombinant E6 proteins as shown in FIG. 15 were used in one or more immunological assays, for example, to be used as a detecting antibody in antibody assays, etc. The purified recombinant E6 proteins were also used to as immunogens for generating antiserum, polyclonal antibody, and monoclonal antibodies specific against HPV-16 E6 protein.

FIG. 15C demonstrates the result of gel filtration column chromatography of the purified recombinant E6 protein, demonstrating that the purified recombinant protein HPV-16-E6 is a monomeric soluble protein with molecular size about 20.5 kDa. The purified recombinant E6 protein is eluted later than BSA.

Example 2

Cloning and Production of Recombinant Proteins Encoded by HPV-16 Early E7 Gene

Cloning of an exemplary oncogenic E7 early gene from an exemplary HPV type, HPV-16, is described herein. A 294 base pair (b.p.) DNA fragment (SEQ ID NO. 7) containing the 99 amino acid coding region (SEQ ID NO. 8) of the HPV-16 E7 gene was obtained by polymerase chain reaction (PCR) amplification. Primers were used for cloning, for example, a pair of forward and reverse primers, 5' cgcGGATCCcatggagatacacctacattgc 3' (SEQ ID NO. 9) and 5' ccgGAATTCtatggtttctgagaacagatgg 3' (SEQ ID NO. 10), respectively. The DNA sequence of the isolated DNA fragment was confirmed by comparing with the sequence from Gene Bank database. In addition, E7 DNA fragments from different strains of HPV-16 can also be cloned from different clinical samples or sources.

The obtained 294 base pair (b.p.) DNA fragment was subcloned into a GST expression vector in order to express a recombinant HPV-16 E7 GST fusion protein. The DNA sequence and the amino acid sequences of the resulting recombinant HPV-16 E7 GST protein are shown as SEQ ID NO. 11 (a 972 base pair (b.p.) DNA fragment) and SEQ ID NO. 6 (a 323 amino acid fusion protein), respectively. The molecular weight of the resulting recombinant HPV-16 E7 GST protein is about 37.2 KD. The recombinant HPV-16 E7 GST proteins were obtained and purified to a final concentration of about 1 mg/L. Other expression systems can also be used to express E7 recombinant proteins from various HPV types and strains. Recombinant E7 fusion proteins or recombinant E7 baculovirus proteins were used to detect the presence of E7 antibody on clinical samples and were also be used as immunogens for production of polyclonal antiserum and monoclonal antibodies.

FIG. 16 is a SDS-PAGE gel, showing one exemplary purified recombinant HPV-16-E7 proteins. As shown in FIG. 3, the HPV-16-E7 recombinant proteins is purified to homogeneity as a major single band with a molecular weight of 37.2 KDa as indicated by an arrow.

FIG. 17 demonstrates SDS-PAGE of three exemplary purified HPV recombinant proteins by commassie blue staining according to one or more embodiments of the invention. Recombinant fusion proteins were obtained for different HPV types, such as different high risk HPV types, e.g., HPV-16, HPV-18, HPV-58, etc. P1 indicates a purified recombinant HPV-58-E6-MBP fusion protein as compared to P3 for a MBP protein alone. P2 indicates a purified recombinant HPV-16-E7-His fusion protein and CP indicates a purified recombinant HPV-16-E6-His fusion protein.

What is claimed:

1. A method of assessing the correlation of HPV infection to a variety of cancers and carcinomas in a clinical sample from a human subject, comprising:
   obtaining a clinical sample from a source sample other than cervical sample;
   conducting one or more detection assays on the clinical sample from the human subject using a monoclonal antibody that specifically binds to two or more native HPV proteins from different HPV types, wherein
   the two or more native HPV proteins are native E7 proteins from different HPV types and/or native E6 proteins from different HPV types, and
   the monoclonal antibody is capable of binding in situ to the native HPV proteins in the clinical sample;
   detecting a presence of an HPV protein in the clinical sample based at least in part upon a result of conducting the one or more detection assays on the clinical sample;
   assigning a score based on the level of the presence of the HPV protein in the clinical sample; and
   determining the correlation of HPV infection to a variety of cancers and carcinomas in the human subject based at least in part upon a result of detecting the presence of the HPV protein in the clinical sample.

2. The method of claim 1, wherein the source sample comprises one or more samples of a bladder sample, a head and neck sample, an ovarian sample, a bladder cancer sample, a head and neck cancer sample, an ovarian cancer sample, a bladder transitional cell carcinoma (TCC) sample, an endometrioid adenocarcinoma sample, a serous papillary cystadenocarcinoma (SPC) sample, an urothelial carcinoma sample, a squamous cell carcinomas of cheeks sample, a tonsillar carcinoma sample, a squamous cell carcinoma of larynx sample, a squamous cell carcinoma of nose sample, a squamous cell carcinoma of upper jaw sample, a low grade squamous cell carcinoma of nasal cavity sample, a clear cell carcinoma sample, a carcinoma sarcomatoid of left ethmoid sinus sample, a low grade endometrioid adenocarcinoma sample, and a normal sample.

3. The method of claim 1, wherein the detection assay is immunohistochemistry (IHC) assay.

4. The method of claim 1, wherein the monoclonal antibody specifically binds to the two or more native HPV proteins from HPV types comprising HPV-16, HPV-18, HPV-31, HPV-33, HPV-39, HPV-45, HPV-51, HPV-52, HPV-58, HPV-59, HPV-6, HPV-11, HPV-44, HPV-53, and HPV-68.

5. The method of claim 1, wherein the detection assay is an assay selected from the group consisting of an ELISA (enzyme linked immunoabsorbent assay), an antigen assay for papillomavirus proteins, an antibody assay for antibodies against papillomavirus proteins, an assay for papillomavirus immunocomplexes, a protein chip assay, a radioimmunoprecipitation assay, a rapid membrane immunochromatographic assay, a rapid stick immunochromatographic assay, an immunohistochemistry assay for tissues or cells, and an immunocytochemistry assay followed by flow cytometry.

\* \* \* \* \*

SEQUENCE LISTING

```
<160> NUMBER OF SEQ ID NOS: 27

<210> SEQ ID NO 1
<211> LENGTH: 474
<212> TYPE: DNA
<213> ORGANISM: pappilomavirus

<400> SEQUENCE: 1
caccaaaaga gaactgcaat gtttcaggac ccacaggagc gacccagaaa gttaccacag      60
ttatgcacag agctgcaaac aactatacat gatataatat tagaatgtgt gtactgcaag     120
caacagttac tgcgacgtga ggtatatgac tttgcttttc gggatttatg catagtatat     180
agagatggga atccatatgc tgtatgtgat aaatgtttaa agttttattc taaaattagt     240
gagtatagac attattgtta tagtttgtat ggaacaacat tagaacagca atacaacaaa     300
ccgttgtgtg atttgttaat taggtgtatt aactgtcaaa agccactgtg tcctgaagaa     360
```

```
aagcaaagac atctggacaa aaagcaaaga ttccataata taaggggtcg gtggaccggt      420
cgatgtatgt cttgttgcag atcatcaaga acacgtagag aaacccagct gtaa            474

<210> SEQ ID NO 2
<211> LENGTH: 157
<212> TYPE: PRT
<213> ORGANISM: pappilomavirus

<400> SEQUENCE: 2

His Gln Lys Arg Thr Ala Met Phe Gln Asp Pro Gln Glu Arg Pro Arg
1               5                   10                  15

Lys Leu Pro Gln Leu Cys Thr Glu Leu Gln Thr Thr Ile His Asp Ile
            20                  25                  30

Ile Leu Glu Cys Val Tyr Cys Lys Gln Gln Leu Leu Arg Arg Glu Val
        35                  40                  45

Tyr Asp Phe Ala Phe Arg Asp Leu Cys Ile Val Tyr Arg Asp Gly Asn
    50                  55                  60

Pro Tyr Ala Val Cys Asp Lys Cys Leu Lys Phe Tyr Ser Lys Ile Ser
65                  70                  75                  80

Glu Tyr Arg His Tyr Cys Tyr Ser Leu Tyr Gly Thr Thr Leu Glu Gln
                85                  90                  95

Gln Tyr Asn Lys Pro Leu Cys Asp Leu Leu Ile Arg Cys Ile Asn Cys
            100                 105                 110

Gln Lys Pro Leu Cys Pro Glu Glu Lys Gln Arg His Leu Asp Lys Lys
        115                 120                 125

Gln Arg Phe His Asn Ile Arg Gly Arg Trp Thr Gly Arg Cys Met Ser
    130                 135                 140

Cys Cys Arg Ser Ser Arg Thr Arg Arg Glu Thr Gln Leu
145                 150                 155

<210> SEQ ID NO 3
<211> LENGTH: 34
<212> TYPE: DNA
<213> ORGANISM: pappilomavirus

<400> SEQUENCE: 3
cgcggatccc accaaaagag aactgcaatg tttc                                  34

<210> SEQ ID NO 4
<211> LENGTH: 32
<212> TYPE: DNA
<213> ORGANISM: pappilomavirus

<400> SEQUENCE: 4
cccaagcttt tacagctggg tttctctacg tg                                    32

<210> SEQ ID NO 5
<211> LENGTH: 510
<212> TYPE: DNA
<213> ORGANISM: pappilomavirus

<400> SEQUENCE: 5
atgagaggat cgcatcacca tcaccatcac ggatcccacc aaaagagaac tgcaatgttt      60
caggacccac aggagcgacc cagaaagtta ccacagttat gcacagagct gcaaacaact     120
atacatgata taatattaga atgtgtgtac tgcaagcaac agttactgcg acgtgaggta     180
tatgactttg cttttcggga tttatgcata gtatatagag atgggaatcc atatgctgta     240
tgtgataaat gtttaaagtt ttattctaaa attagtgagt atagacatta ttgttatagt     300
```

```
ttgtatggaa caacattaga acagcaatac aacaaaccgt tgtgtgattt gttaattagg    360
tgtattaact gtcaaaagcc actgtgtcct gaagaaaagc aaagacatct ggacaaaaag    420
caaagattcc ataatataag gggtcggtgg accggtcgat gtatgtcttg ttgcagatca    480
tcaagaacac gtagagaaac ccagctgtaa                                     510
```

<210> SEQ ID NO 6
<211> LENGTH: 169
<212> TYPE: PRT
<213> ORGANISM: pappilomavirus

<400> SEQUENCE: 6

```
Met Arg Gly Ser His His His His His Gly Ser His Gln Lys Arg
1               5                  10                  15

Thr Ala Met Phe Gln Asp Pro Gln Glu Arg Pro Arg Lys Leu Pro Gln
            20                  25                  30

Leu Cys Thr Glu Leu Gln Thr Thr Ile His Asp Ile Ile Leu Glu Cys
        35                  40                  45

Val Tyr Cys Lys Gln Gln Leu Leu Arg Arg Glu Val Tyr Asp Phe Ala
    50                  55                  60

Phe Arg Asp Leu Cys Ile Val Tyr Arg Asp Gly Asn Pro Tyr Ala Val
65                  70                  75                  80

Cys Asp Lys Cys Leu Lys Phe Tyr Ser Lys Ile Ser Glu Tyr Arg His
                85                  90                  95

Tyr Cys Tyr Ser Leu Tyr Gly Thr Thr Leu Glu Gln Gln Tyr Asn Lys
            100                 105                 110

Pro Leu Cys Asp Leu Leu Ile Arg Cys Ile Asn Cys Gln Lys Pro Leu
        115                 120                 125

Cys Pro Glu Glu Lys Gln Arg His Leu Asp Lys Lys Gln Arg Phe His
    130                 135                 140

Asn Ile Arg Gly Arg Trp Thr Gly Arg Cys Met Ser Cys Cys Arg Ser
145                 150                 155                 160

Ser Arg Thr Arg Arg Glu Thr Gln Leu
                165
```

<210> SEQ ID NO 7
<211> LENGTH: 300
<212> TYPE: DNA
<213> ORGANISM: Papillomavirus sylvilagi

<400> SEQUENCE: 7

```
gatcccatgg agatacacct acattgcatg aatatatgtt agatttgcaa ccagagacaa    60
ctgatctcta ctgttatgag caattaaatg acagctcaga ggaggaggat gaaatagatg   120
gtccagctgg acaagcagaa ccggacagag cccattacaa tattgtaacc ttttgttgca   180
agtgtgactc tacgcttcgg ttgtgcgtac aaagcacaca cgtagacatt cgtactttgg   240
aagacctgtt aatgggcaca ctaggaattg tgtgccccat ctgttctcag aaaccataag   300
```

<210> SEQ ID NO 8
<211> LENGTH: 97
<212> TYPE: PRT
<213> ORGANISM: pappilomavirus -continued

<400> SEQUENCE: 8

His Gly Asp Thr Pro Thr Leu His Glu Tyr Met Leu Asp Leu Gln Pro
1               5                   10                  15

Glu Thr Thr Asp Leu Tyr Cys Tyr Glu Gln Leu Asn Asp Ser Ser Glu
            20                  25                  30

Glu Glu Asp Glu Ile Asp Gly Pro Ala Gly Gln Ala Glu Pro Asp Arg
        35                  40                  45

Ala His Tyr Asn Ile Val Thr Phe Cys Cys Lys Cys Asp Ser Thr Leu
    50                  55                  60

Arg Leu Cys Val Gln Ser Thr His Val Asp Ile Arg Thr Leu Glu Asp
65                  70                  75                  80

Leu Leu Met Gly Thr Leu Gly Ile Val Cys Pro Ile Cys Ser Gln Lys
                85                  90                  95

Pro

<210> SEQ ID NO 9
<211> LENGTH: 31
<212> TYPE: DNA
<213> ORGANISM: pappilomavirus

<400> SEQUENCE: 9
cgcggatccc atggagatac acctacattg c                              31

<210> SEQ ID NO 10
<211> LENGTH: 32
<212> TYPE: DNA
<213> ORGANISM: pappilomavirus

<400> SEQUENCE: 10
ccggaattct tatggtttct gagaacagat gg                             32

<210> SEQ ID NO 11
<211> LENGTH: 972
<212> TYPE: DNA
<213> ORGANISM: pappilomavirus

<400> SEQUENCE: 11 atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acgtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ctggttccgc gtggatccca tggagataca cctacattgc atgaatatat gttagatttg    720
caaccagaga caactgatct ctactgttat gagcaattaa atgacagctc agaggaggag    780
gatgaaatag atggtccagc tggacaagca gaaccggaca gagcccatta caatattgta    840
accttttgtt gcaagtgtga ctctacgctt cggttgtgcg tacaaagcac acacgtagac    900
attcgtactt tggaagacct gttaatgggc acactaggaa ttgtgtgccc catctgttct     960
cagaaaccat aa                                                         972

<210> SEQ ID NO 12
<211> LENGTH: 323
<212> TYPE: PRT
<213> ORGANISM: pappilomavirus

<400> SEQUENCE: 12

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Val Pro Arg
    210                 215                 220

Gly Ser His Gly Asp Thr Pro Thr Leu His Glu Tyr Met Leu Asp Leu
225                 230                 235                 240

Gln Pro Glu Thr Thr Asp Leu Tyr Cys Tyr Glu Gln Leu Asn Asp Ser
                245                 250                 255

Ser Glu Glu Glu Asp Glu Ile Asp Gly Pro Ala Gly Gln Ala Glu Pro
            260                 265                 270

Asp Arg Ala His Tyr Asn Ile Val Thr Phe Cys Cys Lys Cys Asp Ser
        275                 280                 285

Thr Leu Arg Leu Cys Val Gln Ser Thr His Val Asp Ile Arg Thr Leu
    290                 295                 300

Glu Asp Leu Leu Met Gly Thr Leu Gly Ile Val Cys Pro Ile Cys Ser
305                 310                 315                 320

Gln Lys Pro

<210> SEQ ID NO 13
<211> LENGTH: 1602
<212> TYPE: DNA
<213> ORGANISM: pappilomavirus

<400> SEQUENCE: 13

```
tcgagatgca ggtgactttt atttacatcc tagttattac atgttacgaa aacgacgtaa      60
acgtttacca tattttttt cagatgtctc tttggctgcc tagtgaggcc actgtctact     120
tgcctcctgt cccagtatct aaggttgtaa gcacggatga atatgttgca cgcacaaaca     180
tatattatca tgcaggaaca tccagactac ttgcagttgg acatccctat tttcctatta     240
aaaaacctaa caataacaaa atattagttc ctaaagtatc aggattacaa tacagggtat     300
ttagaataca tttacctgac cccaataagt ttggttttcc tgacacctca ttttataatc     360
cagatacaca gcggctggtt tgggcctgtg taggtgttga ggtaggtcgt ggtcagccat     420
taggtgtggg cattagtggc catcctttat taaataaatt ggatgacaca gaaaatgcta     480
gtgcttatgc agcaaatgca ggtgtggata atagagaatg tatatctatg gattacaaac     540
aaacacaatt gtgtttaatt ggttgcaaac cacctatagg ggaacactgg ggcaaaggat     600
ccccatgtac caatgttgca gtaaatccag gtgattgtcc accattagag ttaataaaca     660
cagttattca ggatggtgat atggttcata ctggctttgg tgctatggac tttactacat     720
tacaggctaa caaagtgaa gttccactgg atatttgtac atctatttgc aaatatccag     780
attatattaa aatggtgtca gaaccatatg gcgacagctt attttttttat ttacgaaggg     840
aacaaatgtt tgttagacat ttatttaata gggctggtac tgttggtgaa atgtaccag     900
acgatttata cattaaaggc tctgggtcta ctgcaaattt agccagttca aattattttc    960
ctacacctag tggttctatg gttacctctg atgcccaaat attcaataaa ccttattggt   1020
tacaacgagc acagggccac aataatggca tttgttgggg taaccaacta tttgttactg   1080
ttgttgatac tacacgcagt acaaatatgt cattatgtgc tgccatatct acttcagaaa   1140
ctacatataa aaatactaac tttaaggagt acctacgaca tggggaggaa tatgatttac   1200
agttttatttt tcaactgtgc aaaataacct taactgcaga cgttatgaca tacatacatt   1260
ctatgaattc cactattttg gaggactgga attttggtct acaacctccc ccaggaggca   1320
cactagaaga tacttatagg tttgtaaccc aggcaattgc ttgtcaaaaa catacacctc   1380
cagcacctaa agaagatgat ccccttaaaa aatacacttt tgggaagta aatttaaagg   1440
aaaagttttc tgcagaccta gatcagtttc ctttaggacg caaattttta ctacaagcag   1500
gattgaaggc caaaccaaaa tttacattag aaaacgaaa agctacaccc accacctcat   1560
ctacctctac aactgctaaa cgcaaaaaac gtaagctgta aa                      1602
```

<210> SEQ ID NO 14
<211> LENGTH: 531
<212> TYPE: PRT
<213> ORGANISM: pappilomavirus

<400> SEQUENCE: 14

```
Met Gln Val Thr Phe Ile Tyr Ile Leu Val Ile Thr Cys Tyr Glu Asn
1               5                   10                  15

Asp Val Asn Val Tyr His Ile Phe Phe Gln Met Ser Leu Trp Leu Pro
            20                  25                  30

Ser Glu Ala Thr Val Tyr Leu Pro Pro Val Pro Val Ser Lys Val Val
        35                  40                  45

Ser Thr Asp Glu Tyr Val Ala Arg Thr Asn Ile Tyr Tyr His Ala Gly
    50                  55                  60

Thr Ser Arg Leu Leu Ala Val Gly His Pro Tyr Phe Pro Ile Lys Lys
65                  70                  75                  80
```

```
Pro Asn Asn Asn Lys Ile Leu Val Pro Lys Val Ser Gly Leu Gln Tyr
                85                  90                  95
Arg Val Phe Arg Ile His Leu Pro Asp Pro Asn Lys Phe Gly Phe Pro
            100                 105                 110
Asp Thr Ser Phe Tyr Asn Pro Asp Thr Gln Arg Leu Val Trp Ala Cys
            115                 120                 125
Val Gly Val Glu Val Gly Arg Gly Gln Pro Leu Gly Val Gly Ile Ser
130                 135                 140
Gly His Pro Leu Leu Asn Lys Leu Asp Asp Thr Glu Asn Ala Ser Ala
145                 150                 155                 160
Tyr Ala Ala Asn Ala Gly Val Asp Asn Arg Glu Cys Ile Ser Met Asp
                165                 170                 175
Tyr Lys Gln Thr Gln Leu Cys Leu Ile Gly Cys Lys Pro Pro Ile Gly
            180                 185                 190
Glu His Trp Gly Lys Gly Ser Pro Cys Thr Asn Val Ala Val Asn Pro
            195                 200                 205
Gly Asp Cys Pro Pro Leu Glu Leu Ile Asn Thr Val Ile Gln Asp Gly
210                 215                 220
Asp Met Val His Thr Gly Phe Gly Ala Met Asp Phe Thr Thr Leu Gln
225                 230                 235                 240
Ala Asn Lys Ser Glu Val Pro Leu Asp Ile Cys Thr Ser Ile Cys Lys
                245                 250                 255
Tyr Pro Asp Tyr Ile Lys Met Val Ser Glu Pro Tyr Gly Asp Ser Leu
            260                 265                 270
Phe Phe Tyr Leu Arg Arg Glu Gln Met Phe Val Arg His Leu Phe Asn
            275                 280                 285
Arg Ala Gly Thr Val Gly Glu Asn Val Pro Asp Asp Leu Tyr Ile Lys
290                 295                 300
Gly Ser Gly Ser Thr Ala Asn Leu Ala Ser Ser Asn Tyr Phe Pro Thr
305                 310                 315                 320
Pro Ser Gly Ser Met Val Thr Ser Asp Ala Gln Ile Phe Asn Lys Pro
                325                 330                 335
Tyr Trp Leu Gln Arg Ala Gln Gly His Asn Asn Gly Ile Cys Trp Gly
            340                 345                 350
Asn Gln Leu Phe Val Thr Val Val Asp Thr Thr Arg Ser Thr Asn Met
            355                 360                 365
Ser Leu Cys Ala Ala Ile Ser Thr Ser Glu Thr Thr Tyr Lys Asn Thr
370                 375                 380
Asn Phe Lys Glu Tyr Leu Arg His Gly Glu Glu Tyr Asp Leu Gln Phe
385                 390                 395                 400
Ile Phe Gln Leu Cys Lys Ile Thr Leu Thr Ala Asp Val Met Thr Tyr
                405                 410                 415
Ile His Ser Met Asn Ser Thr Ile Leu Glu Asp Trp Asn Phe Gly Leu
            420                 425                 430
Gln Pro Pro Pro Gly Gly Thr Leu Glu Asp Thr Tyr Arg Phe Val Thr
            435                 440                 445
Gln Ala Ile Ala Cys Gln Lys His Thr Pro Pro Ala Pro Lys Glu Asp
450                 455                 460
Asp Pro Leu Lys Lys Tyr Thr Phe Trp Glu Val Asn Leu Lys Glu Lys
465                 470                 475                 480
Phe Ser Ala Asp Leu Asp Gln Phe Pro Leu Gly Arg Lys Phe Leu Leu
                485                 490                 495
```

Gln Ala Gly Leu Lys Ala Lys Pro Lys Phe Thr Leu Gly Lys Arg Lys
          500                 505                 510

Ala Thr Pro Thr Thr Ser Ser Ser Thr Thr Ala Lys Arg Lys Lys
          515                 520                 525

Arg Lys Leu
   530

<210> SEQ ID NO 15
<211> LENGTH: 34
<212> TYPE: DNA
<213> ORGANISM: pappilomavirus

<400> SEQUENCE: 15
ccgctcgaga tgcaggtgac ttttatttac atcc                                   34

<210> SEQ ID NO 16
<211> LENGTH: 34
<212> TYPE: DNA
<213> ORGANISM: pappilomavirus

<400> SEQUENCE: 16
cccaagcttt tacagcttac gttttttgcg ttta                                   34

<210> SEQ ID NO 17
<211> LENGTH: 1716
<212> TYPE: DNA
<213> ORGANISM: pappilomavirus

<400> SEQUENCE: 17

| | |
|---|---|
| atgccgcggg gttctcatca tcatcatcat catggtatgg ctagcatgac tggtggacag | 60 |
| caaatgggtc gggatctgta cgacgatgac gataaggatc gatggggatc cgagctcgag | 120 |
| atgcaggtga cttttatttta catcctagtt attacatgtt acgaaaacga cgtaaacgtt | 180 |
| taccatattt tttttcagat gtctctttgg ctgcctagtg aggccactgt ctacttgcct | 240 |
| cctgtcccag tatctaaggt tgtaagcacg gatgaatatg ttgcacgcac aaacatatat | 300 |
| tatcatgcag gaacatccag actacttgca gttggacatc cctatttttcc tattaaaaaa | 360 |
| cctaacaata caaaatatt agttcctaaa gtatcaggat acaatacag ggtatttaga | 420 |
| atacatttac ctgaccccaa taagtttggt tttcctgaca cctcattta taatccagat | 480 |
| acacagcggc tggtttgggc ctgtgtaggt gttgaggtag tcgtggtca gccattaggt | 540 |
| gtgggcatta gtggccatcc tttattaaat aaattggatg acacagaaaa tgctagtgct | 600 |
| tatgcagcaa atgcaggtgt ggataataga gaatgtatat ctatggatta caaacaaaca | 660 |
| caattgtgtt taattggttg caaaccacct ataggggaac actggggcaa aggatcccca | 720 |
| tgtaccaatg ttgcagtaaa tccaggtgat tgtccaccat tagagttaat aaacacagtt | 780 |
| attcaggatg gtgatatggt tcatactggc tttggtgcta tggactttac tacattacag | 840 |
| gctaacaaaa gtgaagttcc actggatatt tgtacatcta tttgcaaata tccagattat | 900 |
| attaaaatgg tgtcagaacc atatggcgac agcttatttt tttatttacg aagggaacaa | 960 |
| atgtttgtta gacattttat taataggct ggtactgttg gtgaaaatgt accagacgat | 1020 |
| ttatacatta aaggctctgg gtctactgca aatttagcca gttcaaatta ttttcctaca | 1080 |
| cctagtggtt ctatggttac ctctgatgcc caaatattca ataaaccttat tggttacaa | 1140 |
| cgagcacagg gccacaataa tgcattgt tgggtaacc aactatttgt tactgttgtt | 1200 |
| gatactacac gcagtacaaa tatgtcatta tgtgctgcca tatctactc agaaactaca | 1260 |

-continued

```
tataaaaata ctaactttaa ggagtaccta cgacatgggg aggaatatga tttacagttt    1320
atttttcaac tgtgcaaaat aaccttaact gcagacgtta tgacatacat acattctatg    1380
aattccacta ttttggagga ctggaatttt ggtctacaac ctcccccagg aggcacacta    1440
gaagatactt ataggtttgt aacccaggca attgcttgtc aaaacatac acctccagca     1500 cctaagaag atgatcccct aaaaaatac acttttggg aagtaaattt aaaggaaaag      1560
ttttctgcag acctagatca gtttccttta ggacgcaaat ttttactaca agcaggattg    1620
aaggccaaac caaaatttac attaggaaaa cgaaaagcta cacccaccac ctcatctacc    1680
tctacaactg ctaaacgcaa aaacgtaag ctgtaa                               1716
```

<210> SEQ ID NO 18
<211> LENGTH: 571
<212> TYPE: PRT
<213> ORGANISM: pappilomavirus

<400> SEQUENCE: 18

```
Met Pro Arg Gly Ser His His His His His Gly Met Ala Ser Met
1               5                   10                  15

Thr Gly Gly Gln Gln Met Gly Arg Asp Leu Tyr Asp Asp Asp Lys
            20                  25                  30

Asp Arg Trp Gly Ser Glu Leu Glu Met Gln Val Thr Phe Ile Tyr Ile
        35                  40                  45

Leu Val Ile Thr Cys Tyr Glu Asn Asp Val Asn Val Tyr His Ile Phe
    50                  55                  60

Phe Gln Met Ser Leu Trp Leu Pro Ser Glu Ala Thr Val Tyr Leu Pro
65                  70                  75                  80

Pro Val Pro Val Ser Lys Val Val Ser Thr Asp Glu Tyr Val Ala Arg
                85                  90                  95

Thr Asn Ile Tyr Tyr His Ala Gly Thr Ser Arg Leu Leu Ala Val Gly
            100                 105                 110

His Pro Tyr Phe Pro Ile Lys Lys Pro Asn Asn Asn Lys Ile Leu Val
        115                 120                 125

Pro Lys Val Ser Gly Leu Gln Tyr Arg Val Phe Arg Ile His Leu Pro
    130                 135                 140

Asp Pro Asn Lys Phe Gly Phe Pro Asp Thr Ser Phe Tyr Asn Pro Asp
145                 150                 155                 160

Thr Gln Arg Leu Val Trp Ala Cys Val Gly Val Glu Val Gly Arg Gly
                165                 170                 175

Gln Pro Leu Gly Val Gly Ile Ser Gly His Pro Leu Leu Asn Lys Leu
            180                 185                 190

Asp Asp Thr Glu Asn Ala Ser Ala Tyr Ala Ala Asn Ala Gly Val Asp
        195                 200                 205

Asn Arg Glu Cys Ile Ser Met Asp Tyr Lys Gln Thr Gln Leu Cys Leu
    210                 215                 220

Ile Gly Cys Lys Pro Pro Ile Gly Glu His Trp Gly Lys Gly Ser Pro
225                 230                 235                 240

Cys Thr Asn Val Ala Val Asn Pro Gly Asp Cys Pro Pro Leu Glu Leu
                245                 250                 255

Ile Asn Thr Val Ile Gln Asp Gly Asp Met Val His Thr Gly Phe Gly
            260                 265                 270

Ala Met Asp Phe Thr Thr Leu Gln Ala Asn Lys Ser Glu Val Pro Leu
        275                 280                 285
```

```
Asp Ile Cys Thr Ser Ile Cys Lys Tyr Pro Asp Tyr Ile Lys Met Val
    290                 295                 300

Ser Glu Pro Tyr Gly Asp Ser Leu Phe Phe Tyr Leu Arg Arg Glu Gln
305                 310                 315                 320

Met Phe Val Arg His Leu Phe Asn Arg Ala Gly Thr Val Gly Glu Asn
                325                 330                 335

Val Pro Asp Asp Leu Tyr Ile Lys Gly Ser Gly Ser Thr Ala Asn Leu
            340                 345                 350

Ala Ser Ser Asn Tyr Phe Pro Thr Pro Ser Gly Ser Met Val Thr Ser
        355                 360                 365

Asp Ala Gln Ile Phe Asn Lys Pro Tyr Trp Leu Gln Arg Ala Gln Gly
    370                 375                 380

His Asn Asn Gly Ile Cys Trp Gly Asn Gln Leu Phe Val Thr Val Val
385                 390                 395                 400

Asp Thr Thr Arg Ser Thr Asn Met Ser Leu Cys Ala Ala Ile Ser Thr
                405                 410                 415

Ser Glu Thr Thr Tyr Lys Asn Thr Asn Phe Lys Glu Tyr Leu Arg His
            420                 425                 430

Gly Glu Glu Tyr Asp Leu Gln Phe Ile Phe Gln Leu Cys Lys Ile Thr
        435                 440                 445

Leu Thr Ala Asp Val Met Thr Tyr Ile His Ser Met Asn Ser Thr Ile
    450                 455                 460

Leu Glu Asp Trp Asn Phe Gly Leu Gln Pro Pro Pro Gly Gly Thr Leu
465                 470                 475                 480

Glu Asp Thr Tyr Arg Phe Val Thr Gln Ala Ile Ala Cys Gln Lys His
                485                 490                 495

Thr Pro Pro Ala Pro Lys Glu Asp Pro Leu Lys Lys Tyr Thr Phe
            500                 505                 510

Trp Glu Val Asn Leu Lys Glu Lys Phe Ser Ala Asp Leu Asp Gln Phe
        515                 520                 525

Pro Leu Gly Arg Lys Phe Leu Leu Gln Ala Gly Leu Lys Ala Lys Pro
    530                 535                 540

Lys Phe Thr Leu Gly Lys Arg Lys Ala Thr Pro Thr Thr Ser Ser Thr
545                 550                 555                 560

Ser Thr Thr Ala Lys Arg Lys Arg Lys Leu
                565                 570

<210> SEQ ID NO 19
<211> LENGTH: 322
<212> TYPE: PRT
<213> ORGANISM: pappilomavirus

<400> SEQUENCE: 19

Met Ala Ser Met Thr Gly Gly Gln Gln Met Gly Arg Gly Ser Gln Val
1               5                   10                  15

Thr Phe Ile Tyr Ile Leu Val Ile Thr Cys Tyr Glu Asn Asp Val Asn
            20                  25                  30

Val Tyr His Ile Phe Phe Gln Met Ser Leu Trp Leu Pro Ser Glu Ala
        35                  40                  45

Thr Val Tyr Leu Pro Pro Val Pro Val Ser Lys Val Ser Thr Asp
    50                  55                  60

Glu Tyr Val Ala Arg Thr Asn Ile Tyr Tyr His Ala Gly Thr Ser Arg
65                  70                  75                  80

Leu Leu Ala Val Gly His Pro Tyr Phe Pro Ile Lys Lys Pro Asn Asn
                85                  90                  95
```

-continued

```
Asn Lys Ile Leu Val Pro Lys Val Ser Gly Leu Gln Tyr Arg Val Phe
            100                 105                 110

Arg Ile His Leu Pro Asp Pro Asn Lys Phe Gly Phe Pro Asp Thr Ser
        115                 120                 125

Phe Tyr Asn Pro Asp Thr Gln Arg Leu Val Trp Ala Cys Val Gly Val
130                 135                 140

Glu Val Gly Arg Gly Gln Pro Leu Gly Val Gly Ile Ser Gly His Pro
145                 150                 155                 160

Leu Leu Asn Lys Leu Asp Asp Thr Glu Asn Ala Ser Ala Tyr Ala Ala
                165                 170                 175

Asn Ala Gly Val Asp Asn Arg Glu Cys Ile Ser Met Asp Tyr Lys Gln
            180                 185                 190

Thr Gln Leu Cys Leu Ile Gly Cys Lys Pro Pro Ile Gly Glu His Trp
        195                 200                 205

Gly Lys Gly Ser Pro Cys Thr Asn Val Ala Val Asn Pro Gly Asp Cys
210                 215                 220

Pro Pro Leu Glu Leu Ile Asn Thr Val Ile Gln Asp Gly Asp Met Val
225                 230                 235                 240

His Thr Gly Phe Gly Ala Met Asp Phe Thr Thr Leu Gln Ala Asn Lys
                245                 250                 255

Ser Glu Val Pro Leu Asp Ile Cys Thr Ser Ile Cys Lys Tyr Pro Asp
            260                 265                 270

Tyr Ile Lys Met Val Ser Glu Pro Tyr Gly Asp Ser Leu Phe Phe Tyr
        275                 280                 285

Leu Arg Arg Glu Gln Met Phe Val Arg His Leu Phe Asn Arg Ala Gly
290                 295                 300

Thr Val Gly Glu Asn Val Pro Asp Asp Leu Val Glu His His His His
305                 310                 315                 320

His His

<210> SEQ ID NO 20
<211> LENGTH: 20
<212> TYPE: DNA
<213> ORGANISM: pappilomavirus
<220> FEATURE:
<221> NAME/KEY: misc_feature
<222> LOCATION: (3)..(3)
<223> OTHER INFORMATION: n is a, c, g, or t

<400> SEQUENCE: 20 gncargghc ayaayaatgg                                                  20

<210> SEQ ID NO 21
<211> LENGTH: 23
<212> TYPE: DNA
<213> ORGANISM: pappilomavirus

<400> SEQUENCE: 21
gtdgtatcha cmhcagtaac aaa                                             23

<210> SEQ ID NO 22
<211> LENGTH: 64
<212> TYPE: DNA
<213> ORGANISM: pappilomavirus

<400> SEQUENCE: 22
cvcaggghca yaayaatggc atttgttggg gtaaccaact atttgttact gttgtdgaya    60 cyac                                                                  64
```

<210> SEQ ID NO 23
<211> LENGTH: 20
<212> TYPE: DNA
<213> ORGANISM: pappilomavirus

<400> SEQUENCE: 23
gttactgcga cgtgaggtat                                              20

<210> SEQ ID NO 24
<211> LENGTH: 20
<212> TYPE: DNA
<213> ORGANISM: pappilomavirus

<400> SEQUENCE: 24
gtttcaggac ccacaggagc                                              20

<210> SEQ ID NO 25
<211> LENGTH: 20
<212> TYPE: DNA
<213> ORGANISM: pappilomavirus

<400> SEQUENCE: 25
caacggtttg ttgtattgct                                              20

<210> SEQ ID NO 26
<211> LENGTH: 181
<212> TYPE: DNA
<213> ORGANISM: pappilomavirus

<400> SEQUENCE: 26
gttactgcga cgtgaggtat atgactttgc ttttcgggat ttatgcatag tatatagaga      60
tgggaatcca tatgctgtat gtgataaatg tttaaagttt tattctaaaa ttagtgagta     120
tagacattat tgttatagtt tgtatggaac aacattagaa cagcaataca acaaaccgtt     180
g                                                                    181

<210> SEQ ID NO 27
<211> LENGTH: 286
<212> TYPE: DNA
<213> ORGANISM: pappilomavirus

<400> SEQUENCE: 27
gtttcaggac ccacaggagc gacccagaaa gttaccacag ttatgcacag agctgcaaac      60
aactatacat gatataatat tagaatgtgt gtactgcaag caacagttac tgcgacgtga     120
ggtatatgac tttgcttttc gggatttatg catagtatat agagatggga atccatatgc     180
tgtatgtgat aaatgtttaa agttttattc taaaattagt gagtatagac attattgtta     240
tagtttgtat ggaacaacat tagaacagca atacaacaaa ccgttg                   286